(12) United States Patent
Bassaganya-Riera et al.

(10) Patent No.: US 9,101,573 B2
(45) Date of Patent: Aug. 11, 2015

(54) LANTHIONINE SYNTHETASE COMPONENT C-LIKE PROTEINS AS MOLECULAR TARGETS FOR PREVENTING AND TREATING DISEASES AND DISORDERS

(75) Inventors: Josep Bassaganya-Riera, Blacksburg, VA (US); Pinyi Lu, Blacksburg, VA (US); Raquel Hontecillas, Blacksburg, VA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 693 days.

(21) Appl. No.: 13/100,795

(22) Filed: May 4, 2011

(65) Prior Publication Data

US 2011/0275558 A1    Nov. 10, 2011

Related U.S. Application Data

(60) Provisional application No. 61/331,086, filed on May 4, 2010.

(51) Int. Cl.
*A61K 31/4184* (2006.01)
*A61K 31/13* (2006.01)
(Continued)

(52) U.S. Cl.
CPC ............... *A61K 31/13* (2013.01); *A61K 31/135* (2013.01); *A61K 31/35* (2013.01); *A61K 31/352* (2013.01);
(Continued)

(58) Field of Classification Search
None
See application file for complete search history.

(56) References Cited

U.S. PATENT DOCUMENTS 6,977,141 B2  12/2005  Yuan et al.
7,285,411 B1  10/2007  Parce et al.
(Continued)

FOREIGN PATENT DOCUMENTS

WO    2010-015646 A1    2/2010
WO    WO-2010/088375 A2    8/2010

OTHER PUBLICATIONS

Arnold et al (Peroxisome proliferator-activated receptor-γ agonists inhibit the release of proinflammatory cytokines from RSV-infected epithelial cells. Virology, 2006; 346:427-439).*

(Continued)

*Primary Examiner* — Marcos Sznaidman
*Assistant Examiner* — Rayna B Rodriguez
(74) *Attorney, Agent, or Firm* — Blank Rome LLP

(57) ABSTRACT

The present invention relates to the field of medical treatments for diseases and disorders. More specifically, the present invention relates to the use of the lanthionine synthetase component C-like (LANCL) proteins as therapeutic targets for novel classes of anti-inflammatory, immune regulatory and antidiabetic drugs. This includes but it is not limited to abscisic acid (ABA), ABA analogs, benzimidazophenyls, repurposed drugs or drug combinations, including thiazolidinediones (TZDs); naturally occurring compounds such as conjugated diene fatty acids, conjugated triene fatty acids, isoprenoids, and natural and synthetic agonists of peroxisome proliferator-activated receptors that activate this receptor through an alternative mechanism of action involving LANCL2 or other membrane proteins to treat or prevent the common inflammatory pathogenesis underlying type 2 diabetes, atherosclerosis, cancer, some inflammatory infectious diseases such as influenza and autoimmune diseases including but not limited to inflammatory bowel disease (Crohn's disease and Ulcerative colitis), rheumatoid arthritis, multiple sclerosis and type 1 diabetes and other chronic inflammatory conditions.

10 Claims, 30 Drawing Sheets

(51) Int. Cl.

| | |
|---|---|
| A61K 31/135 | (2006.01) |
| A61K 31/35 | (2006.01) |
| A61K 31/352 | (2006.01) |
| A61K 31/40 | (2006.01) |
| A61K 31/405 | (2006.01) |
| A61K 31/427 | (2006.01) |
| A61K 31/431 | (2006.01) |
| A61K 31/495 | (2006.01) |
| A61K 31/496 | (2006.01) |
| A61K 31/4985 | (2006.01) |
| A61K 31/517 | (2006.01) |
| A61K 31/545 | (2006.01) |
| A61K 31/55 | (2006.01) |
| A61K 31/56 | (2006.01) |
| A61K 31/57 | (2006.01) |
| A61K 31/65 | (2006.01) |
| A61K 31/655 | (2006.01) |
| A61K 31/704 | (2006.01) |
| A61K 31/7048 | (2006.01) |
| G01N 33/573 | (2006.01) |
| G06F 19/16 | (2011.01) |

(52) U.S. Cl.
CPC ............... *A61K 31/40* (2013.01); *A61K 31/405* (2013.01); *A61K 31/4184* (2013.01); *A61K 31/427* (2013.01); *A61K 31/431* (2013.01); *A61K 31/495* (2013.01); *A61K 31/496* (2013.01); *A61K 31/4985* (2013.01); *A61K 31/517* (2013.01); *A61K 31/545* (2013.01); *A61K 31/55* (2013.01); *A61K 31/56* (2013.01); *A61K 31/57* (2013.01); *A61K 31/65* (2013.01); *A61K 31/655* (2013.01); *A61K 31/704* (2013.01); *A61K 31/7048* (2013.01); *G01N 33/573* (2013.01); *G01N 2500/04* (2013.01); *G06F 19/16* (2013.01); *Y10T 436/143333* (2015.01); *Y10T 436/145555* (2015.01); *Y10T 436/147777* (2015.01)

(56) References Cited

U.S. PATENT DOCUMENTS

| | | | |
|---|---|---|---|
| 7,482,425 | B2 | 1/2009 | Kochendoerfer et al. |
| 7,683,055 | B2 | 3/2010 | Hensley |
| 7,887,753 | B2 | 2/2011 | Quake et al. |
| 2005/0020654 | A1* | 1/2005 | Pershadsingh et al. ....... 514/394 |
| 2007/0184060 | A1 | 8/2007 | Bassaganya-Riera et al. |

OTHER PUBLICATIONS

Carpenter et al "Predisposition of infants with chronic lung disease to respiratory syncytial virus-induced respiratory failure: a vascular hypothesis." Pediatr Infect Dis J, 2004; 23(1):S33-40).*
Kumar, V., et al., "Robbins and Cotran Pathologic Basis of Disease", 2005, pp. 1525, 7th ed., Philadelphia: Elsevier Saunders.
Inzuchhi, S. et al., "The Prevention of Type 2 Diabetes Mellitus", 2005, pp. 199-219, Endocrinology and Metabolism Clinics of North America, vol. 34.
Defronzo, R.A., "Pharmacologic Therapy for Type 2 Diabetes Mellitus", Annals of Internal Medicine, 1999, pp. 281-303, vol. 131, No. 4.
Defronzo, R., et al., "Effects of Exenatide (Exendin-4) on Glycemic Control and Weight over 30 Weeks in Metformin-Treated Patients with Type 2 Diabetes", Diabetes Care, 2005, pp. 1092-1100, vol. 28.
Rang, H., et al., "Pharmacology, 5th edition", 2003, pp. 388-389.
Nesto, R.W., et al., "Thiazolidinedione Use, Fluid Retention, and Congestive Heart Failure", A Consensus Statement from the American Heart Association and American Diabetes Association. Diabetes Care, Jan. 2004, pp. 256-263, vol. 27.

Lewis, S.N., et al., "Virtual Screening as a Technique for PPAR Modulator Discovery". PPAR Research, 2010, pp. 1-10.
Bassaganya-Riera, J., et al., "Mechanisms of Action and Medicinal Applications of Abscisic Acid", Current Medicinal Chemistry, 2010, pp. 467-478, vol. 17.
Guri, A.J., et al., "Loss of PPAR Gamma in Immune Cells Impairs the Ability of Abscisic Acid to Improve Insulin Sensitivity by Suppressing Monocyte Chemoattractant Protein-1 Expression and Macrophage Infiltration into White Adipose Tissue", Journal of Nutritional Biochemistry, 2008, pp. 216-228, vol. 19, No. 4.
Sturla, L., et al., "LANCL2 is Necessary for Abscisic Acid Binding and Signaling in Human Granulocytes and in Rat Insulinoma Cells", The Journal of Biological Chemistry, 2009, pp. 28045-28057, vol. 284, No. 41.
Landlinger, C., et al., "Myristoylation of Human LanC-like Protein 2 (LANCL2) is Essential for the Interaction with the Plasma Membrane and the Increase in Cellular Sensitivity to Adriamycin," Biochimica et Biophysica Acta, 2006, pp. 1759-1767, vol. 1758.
Lu, P., et al., "Molecular Modeling of Lanthionine Synthetase Component C-like Protein 2: a Potential Target for the Discovery of Novel Type 2 Diabetes Prophylactics and Therapeutics", Journal of Molecular Modeling, 2011, pp. 543-553, vol. 17, No. 3.
Zhang, W., et al., "Structure of Human Lanthionine Synthetase C-like Protein 1 and its Interaction with Eps8 and Glutathione", Genes & Development, 2009, pp. 1387-1392, vol. 23.
Altschul, S.F., et al., "Basic Local Alignment Search Tool", Journal of Molecular Biology, 1990, pp. 403-410, vol. 215.
Thompson, J.D. et al., "CLUSTAL W: Improving the Sensitivity of Progressive Multiple Sequence Alignment through Sequence Weighting, Position-Specific Gap Penalties and Weight Matrix Choice", Nucleic Acids Research, 1994, pp. 4673-4680, vol. 22, No. 22.
Subramaniam, S., "The Biology Workbench—a Seamless Database and Analysis Environment for the Biologist", Proteins, 1998, pp. 1-2, vol. 32.
Arnold, K., et al., "The Swiss-Model Workspace: a Web-Based Environment for Protein Structure Homology Modelling", Bioinformatics, 2006, pp. 195-201, vol. 22, No. 2, Oxford, England.
Berman, H.M., et al., "The Protein Data Bank", Nucleic Acids Research, 2000, pp. 235-242, vol. 28, No. 1.
Melo, F. and E. Feytmans, "Assessing Protein Structures with a Non-Local Atomic Interaction Energy", Journal of Molecular Biology, 1998, pp. 1141-1152, vol. 277.
Laskowski, R., et al., "PROCHECK: A Program to Check the Stereochemical Quality of Protein Structures", Journal of Applied Crystallography, 1993, pp. 283-291, vol. 26.
Hess, B., et al., "GROMACS 4: Algorithms for Highly Efficient, Load-Balanced, and Scalable Molecular Simulation", Journal of Chemical Theory and Computation, 2008, pp. 435-447, vol. 4.
Jorgensen, W.L. and Tirado-Rives, J., "The OPLS Force Field for Proteins. Energy Minimizations for Crystals of Cyclic Peptides and Crambin", Journal of the American Chemical Society, 1988, pp. 1657-1666, vol. 110, No. 6.
Wiberg, K.B., "A Scheme for Strain Energy Minimization. Application to the Cycloalkanes", Journal of the American Chemical Society, 1965, p. 1070-1078, vol. 87, No. 5.
Mosca, R. and Schneider, T.R., "RAPIDO: A Web Server for the Alignment of Protein Structures in the Presence of Conformational Changes", Nucleic Acids Research, 2008, vol. 36, pp. W42-W46.
Wang, Y., et al., "PubChem: A Public Information System for Analyzing Bioactivities of Small Molecules", Nucleic Acids Research, 2009, pp. W623-W633, vol. 37.
Morris, G.M., et al., "Software News and Updates AutoDock4 and AutoDockTools4: Automated Docking with Selective Receptor Flexibility", Journal of Computational Chemistry, 2009, pp. 2785-2791, vol. 30, No. 16.
Morris, G.M., et al., "Automated Docking Using a Lamarckian Genetic Algorithm and an Empirical Binding Free Energy Function", Journal of Computational Chemistry, 1998, pp. 1639-1662, vol. 19.
Hetenyi, C. C and D. Van Der Spoel, "Efficient Docking of Peptides to Proteins without Prior Knowledge of the Binding Site", Protein Science: A Publication of the Protein Society, 2002, pp. 1729-1737, vol. 11.

(56) References Cited

OTHER PUBLICATIONS

Hetenyi, C. and D. Van Der Spoel, "Blind Docking of Drug-Sized Compounds to Proteins with up to a Thousand Residues", FEBS Letters, 2006, pp. 1447-1450, vol. 580.

Bikadi, Z., et al., "Molecular Modeling of Non-Covalent Binding of Homochiral (3S,3'S)-Astaxanthin to Matrix Metalloproteinase-13 (MMP-13)", Bioorganic & Medicinal Chemistry, 2006, pp. 5451-5458, vol. 14.

Iorga, B., et al., "Acetylcholine Nicotinic Receptors: Finding the Putative Binding Site of Allosteric Modulators using the "Blind Docking" Approach", Journal of Molecular Modeling, 2006, pp. 366-372, vol. 12.

Hazai, E., et al., "Molecular Modeling of the Non-Covalent Binding of the Dietary Tomato Carotenoids Lycopene and Lycophyll, and Selected Oxidative Metabolites with 5-Lipoxygenase", Bioorganic & Medicinal Chemistry, 2006, pp. 6859-6867, vol. 14.

Kovacs, M., et al., "Mechanism of Blebbistatin Inhibition of Myosin II", The Journal of Biological Chemistry, 2004, pp. 35557-35563, vol. 279, No. 34.

Trott, O. and Olson, A.J., "AutoDock Vina: Improving the Speed and Accuracy of Docking with a New Scoring Function, Efficient Optimization, and Multithreading", Journal of Computational Chemistry, 2010, pp. 455-461, vol. 31, No. 2.

Rost, B., "Twilight Zone of Protein Sequence Alignments", Protein Engineering, 1999, pp. 85-94, vol. 12, No. 2.

Gao, Z., et al., "PDTD: A Web-Accessible Protein Database for Drug Target Identification", BMC Bioinformatics, 2008. pp. 104, vol. 9, No. 2.

Li, H., et al., "TarFisDock: A Web Server for Identifying Drug Targets with Docking Approach", Nucleic Acids Research, 2006, pp. W219-W224, vol. 34, (Web Server issue).

Humphrey, W., et al., "VMD: Visual Molecular Dynamics", Journal of Molecular Graphics, 1996, pp. 33-38, vol. 14, No. 1.

Khan, W.I., et al., "Critical Role of MCP-1 in the Pathogenesis of Experimental Colitis in the Context of Immune and Enterochromaffin Cells," American Journal of Physiological Gastrointestinal and Liver Physiology, 2006, pp. G803-G811, vol. 291, No. 5.

Mudter, J. and Neurath, M.F., "Il-6 Signaling in Inflammatory Bowel Disease: Pathophysiological Role and Clinical Relevance", Inflammatory Bowel Disease, 2007, pp. 1016-1023, vol. 13, No. 8.

Van Heel, D.A., et al., "Inflammatory Bowel Disease is Associated with a TNF Polymorphism that Affects an Interaction between the OCT1 and NF(-kappa)B Transcription Factors", Human Molecular Genetics, 2002, pp. 1281-1289, vol. 11, No. 11.

Groux, H. and Powrie, F., Regulatory T Cells and Inflammatory Bowel Disease, Immunology Today, 1999, pp. 442-445, vol. 20, No. 10.

Boden, E.K. and Snapper, S.B., Regulatory T Cells in Inflammatory Bowel Disease, Current Opinion in Gastroenterology, 2008, vol. 24, No. 6.

Leach, M.W., et al., The Role of Il-10 in Inflammatory Bowel Disease: "Of Mice and Men", Toxicologic Pathology, 1999, p. 733-741, vol. 27, No. 1.

Li, M.G. and He, S.H., "Il-10 and its Related Cytokines for Treatment of Inflammatory Bowel Disease", World Journal of Gastroenterology, 2004, pp. 620-625, vol. 10, No. 5.

Guri, A.J., et al., "Abscisic Acid Ameliorates Atherosclerosis by Suppressing Macrophage and CD4+ T Cell Recruitment into the Aortic Wall", Journal of Nutritional Biochemistry, 2010, pp. 1178-1185, vol. 21, No. 12.

Bassaganya-Riera, J., et al., "PPAR-Gamma Activation as an Anti-Inflammatory Therapy for Respiratory Virus Infections", Viral Immunology, 2010, vol. 23, No. 4, pp. 343-352.

Bassaganya-Riera, J. et al.: "Abscisic Acid Regulates Inflammation via Ligand-binding Domain-independent Activation of Peroxisome Proliferator-activated Receptor", Journal of Biological Chemistry, vol. 286, No. 4; Jan. 28, 2011.

* cited by examiner

Fig. 2.

```
Score =  487 bits (1253),  Expect = 1e-135, Method: Compositional matrix adjust.
Identities = 231/426 (54%), Positives = 304/426 (71%), Gaps = 27/426 (6%)

Query  19   MEERAFVNPFPDYEAAAGALLASGAAEETGCVRPPATTDEPGLPFHQDGKIIHNFIRRIQ   78
            M +RAF NP+ DY +    LA G                    F   G++   F +R+
Sbjct  13   MAQRAFPNPYADYNKS----LAEGY------------------FDAAGRLTPEFSQRLT   49

Query  79   TKIRDLLQQMEEGLKTADPHDCSAYTGWTGIALLYLQLYRVTCDQTYLLRSLDYVKRTLR  138
              KI++LLQQME GLK+ADP D + YTGW GIA+LYL LY V  D YL  +   YVK++L
Sbjct  50   NKIRELLQQMERGLKSADPRDGTGYTGWAGIAVLYLHLYDVFGDPAYLQLAHGYVKQSLN  109

Query  139  NLNGRRVTFLCGDAGPLAVGAVIYHKLRSDCESQECVTKLLQLQRSVVCQESDLFDELLY  198
              L R +TFLCGDAGPLAV AV+YHK+ ++   +++C+T+L+ L +    +   P+E+LY
Sbjct  110  CLTKRSITFLCGDAGPLAVAVLYHKMNNEKQAEDCITRLIHLNKI----DPHAPNEMLY  165

Query  199  GRAGYLYALLYLNTEIGPGTVCESAIKEVVNAIIESGKTLSREERKTERCFLLYQWHRKQ  258
            GR GY+YALL++N  G   + +S I+++    I+ SG+ L+R+    F + PL+Y+W+++
Sbjct  166  GRIGYIYALLFVNKNFGVEKIPQSHIQQICETILTSGENLARKRNFTAKSPLMYEWYQEY  225

Query  259  YVGAAHGMAGIYYMLMQPAAKVDQETLTEMVKPSIDYVRHKKFRSGNYPSSLSNETDRLV  318
            YVGAAHG+AGIYY LMQP+ +V Q L  +VKPS+DYV   RF SGNYP  + +  D LV
Sbjct  226  YVGAAHGLAGIYYYLMQPSLQVSQGKLESLVKPSVDYVCQLRFPSGNYPPCIGDNRDLLY  285

Query  319  HWCHGAPGVIHMLMQAYRVFKEEKYLKEAMECSDVIKQRGLLRKGYGICHGTAGNGYSFL  378
            HWCHGAPGVI+ML+QAYRVF+EEKYL +A +C+DVI+Q GLL+KGYG+CHG+AGN Y+FL
Sbjct  286  HWCHGAPGVIYMLIQAYKVFREEKYLCDAYQCADVIWQYGLLKKGYGLCHGSAGNAYAFL  345

Query  379  SLYRLTQDKKYLRACKFAEWCLDYGAHGCRIPDRPYSLFEGMAGAIHFLSDVLGPETSR  438
            +LY LTQD KYLRACKFAEWCL+YG HGCR PD P+SLFEGMAG I+FL+D+L P  +R
Sbjct  346  TLYNLTQDMKYLRACKFAEWCLEYGEHGCRTPDTPFSLFEGMAGTIYFLADLLVPTKAR  405

Query  439  FPAFEL  444
            FPAFEL     (similar amino acids of SEQ ID NO: 1 and SEQ ID NO: 2)
Sbjct  406  FPAFEL  411
```

Query = amino acids 19 -444 of SEQ ID NO: 1
Sbjct = amino acids 13-411 of SEQ ID NO: 2

LanCL2_MM2 = SEQ ID NO.: 3
LanCL2_HS = SEQ ID NO.: 1
LanCL2_RN = SEQ ID NO.: 4
LanCL2_MM = SEQ ID NO.: 6
LanCL2_BT = SEQ ID NO.: 8
LanCL1_MM = SEQ ID NO.: 7
LanCL1_RN = SEQ ID NO.: 5
LanCL1_HS = SEQ ID NO.: 2
LanCL1_BT = SEQ ID NO.: 9
LanCL1_DR = SEQ ID NO.: 10

Fig. 16.
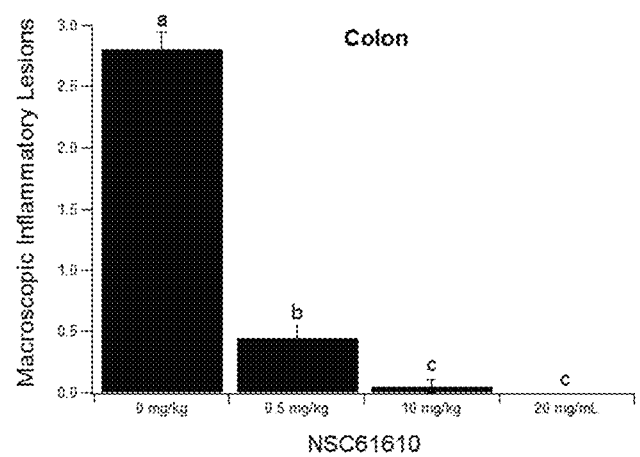
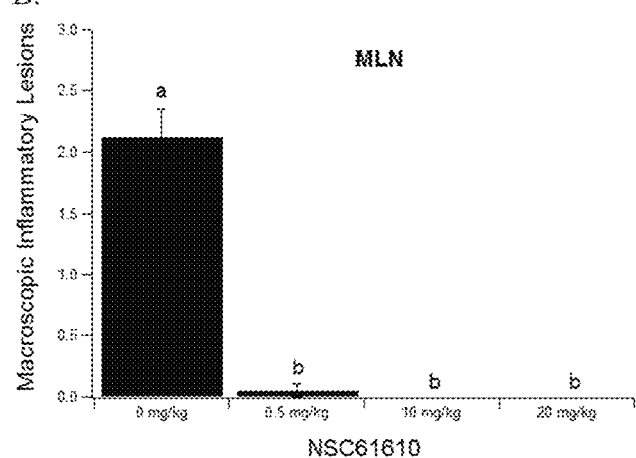
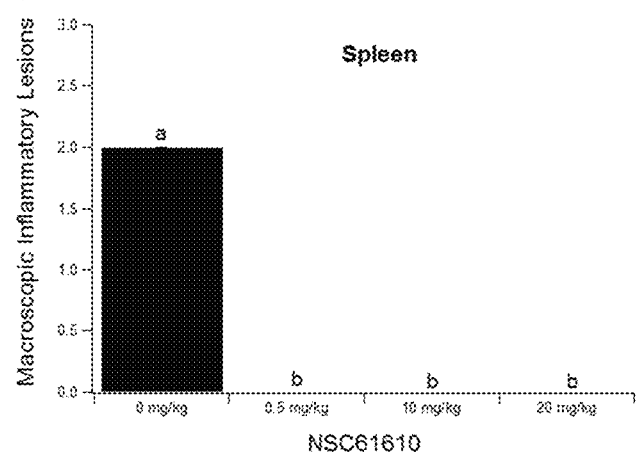

Fig. 17.
A.
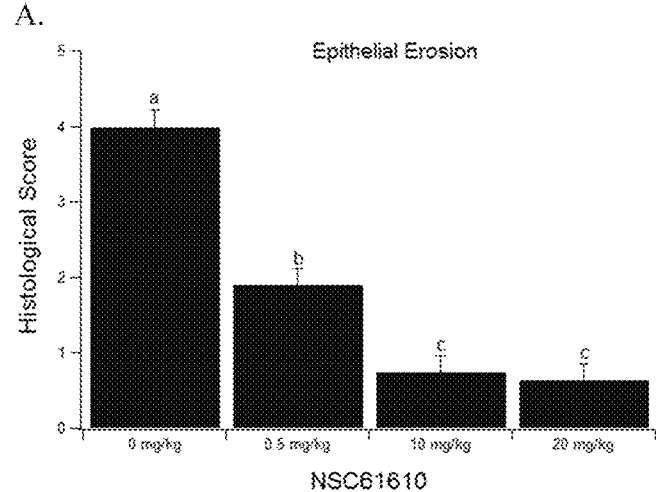
B.
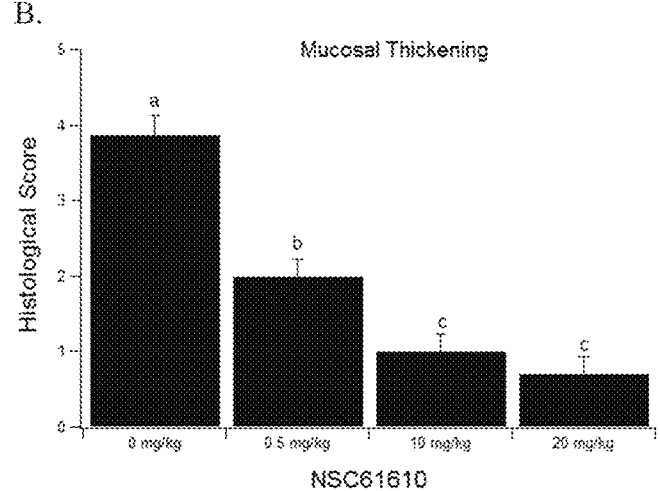
C.
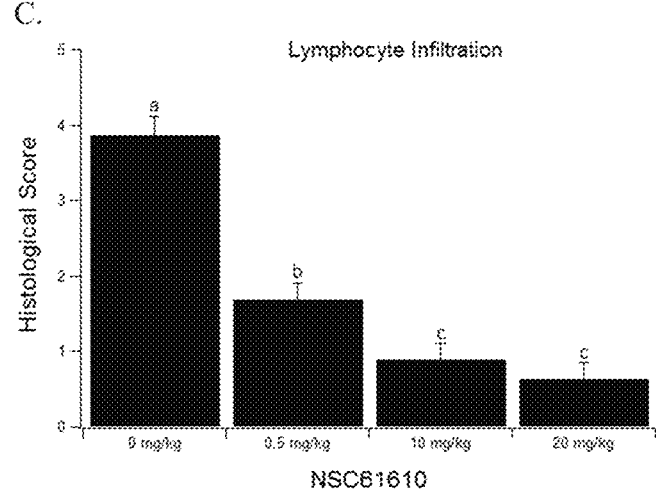

Fig. 19
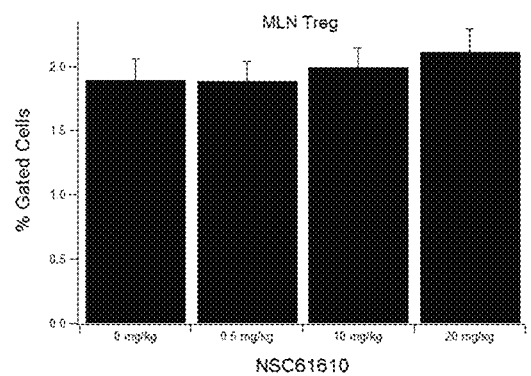
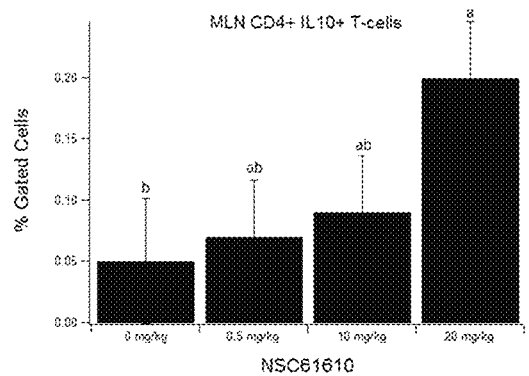
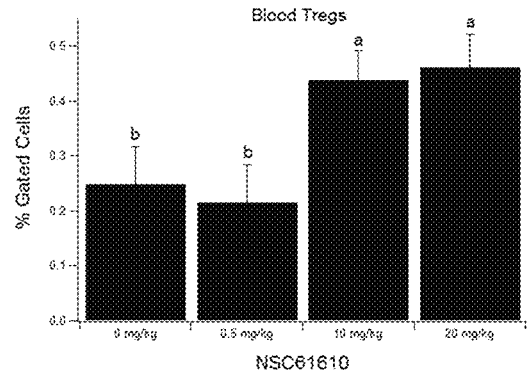
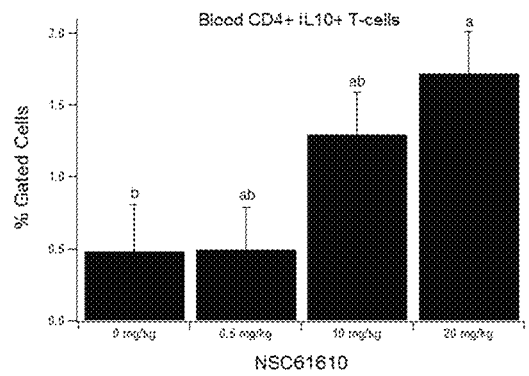

Fig. 24.
A.
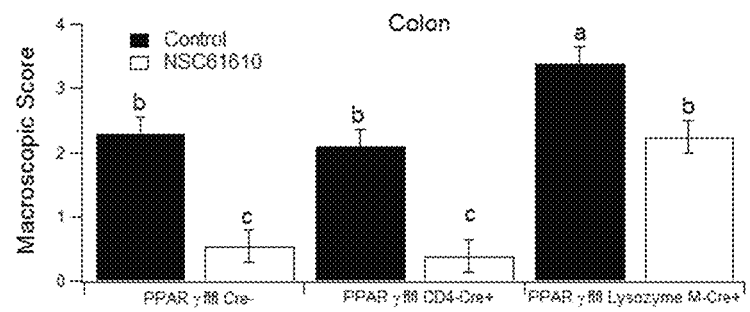
B.
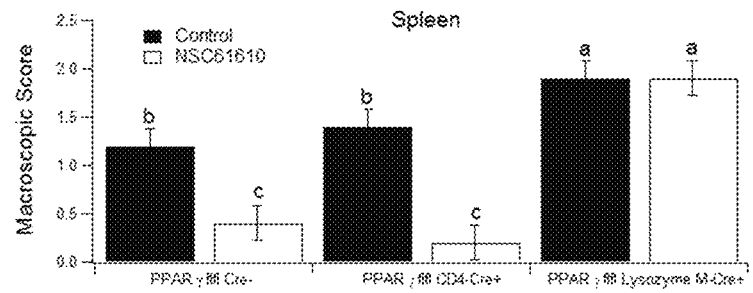
C.
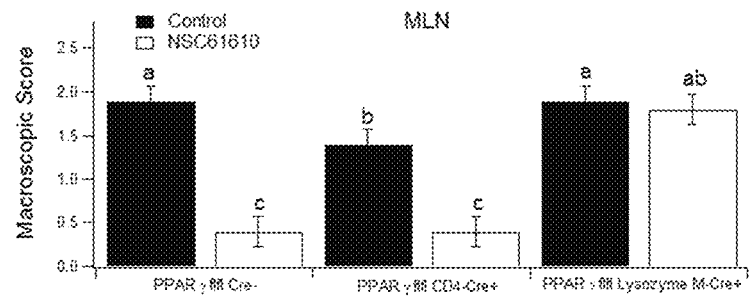

Fig. 27.
A.
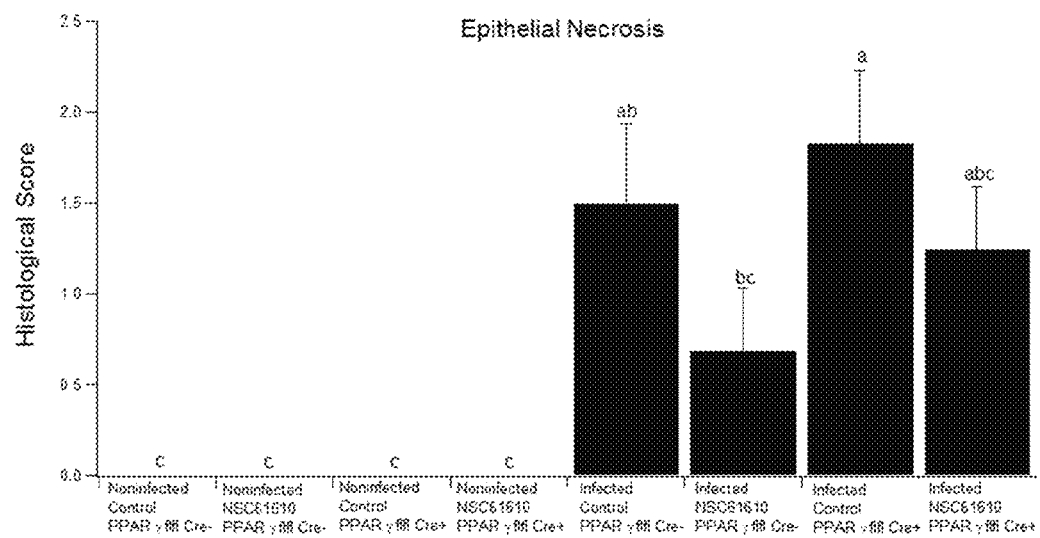
B.
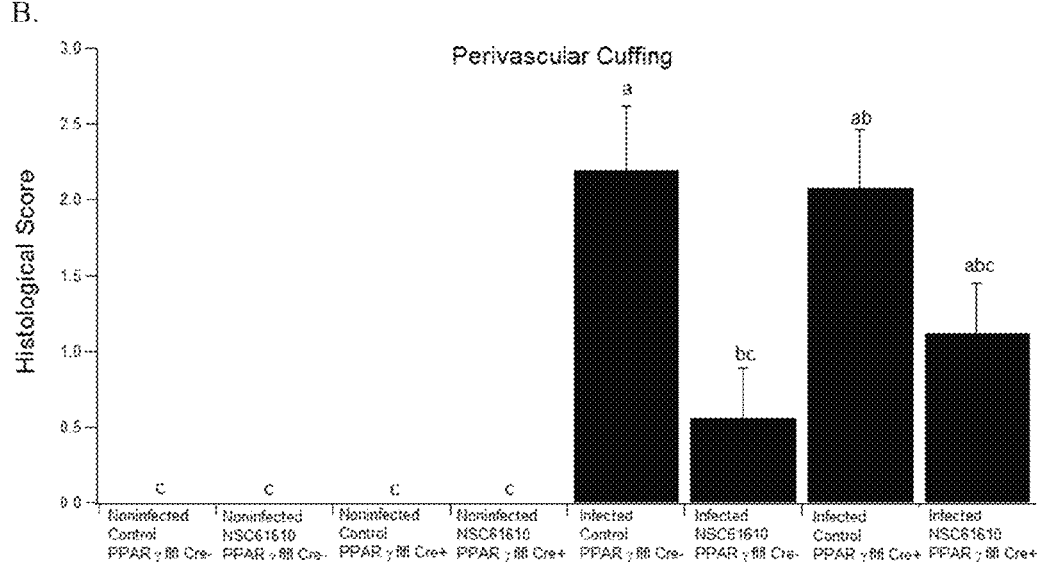

Fig. 27
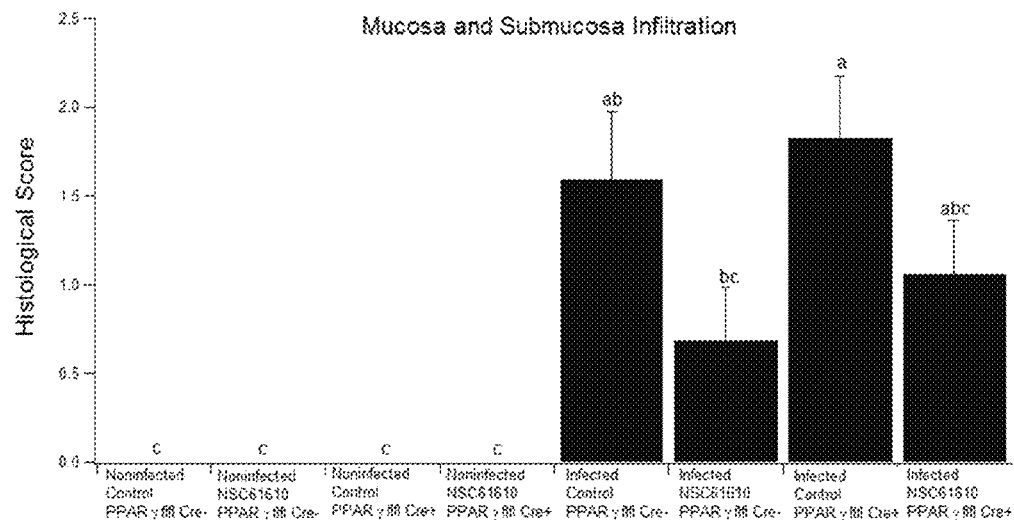
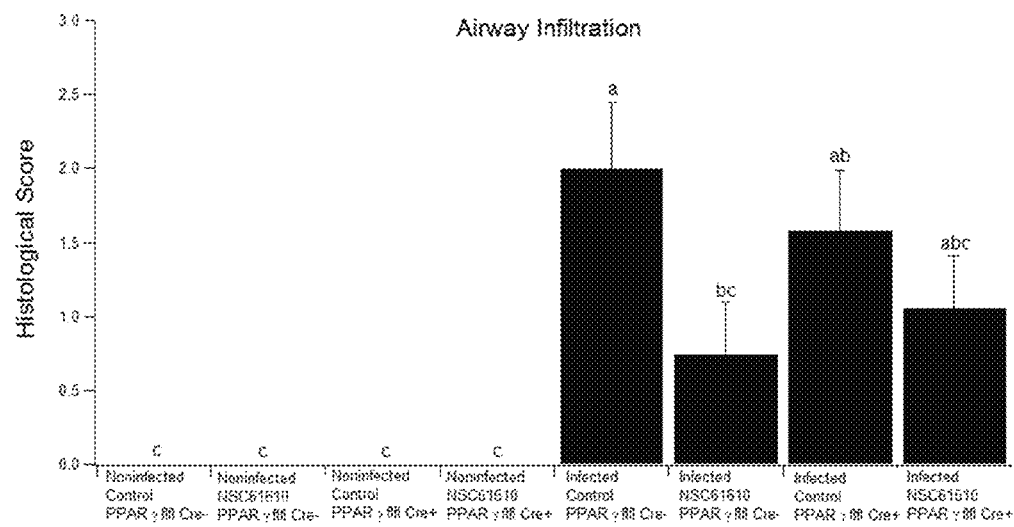

SEQUENCE LISTING

```
<160> NUMBER OF SEQ ID NOS: 10

<210> SEQ ID NO 1
<211> LENGTH: 450
<212> TYPE: PRT
<213> ORGANISM: Homo sapiens

<400> SEQUENCE: 1

Met Gly Glu Thr Met Ser Lys Arg Leu Lys Leu His Leu Gly Gly Glu
1               5                   10                  15

Ala Glu Met Glu Glu Arg Ala Phe Val Asn Pro Phe Pro Asp Tyr Glu
            20                  25                  30

Ala Ala Ala Gly Ala Leu Leu Ala Ser Gly Ala Ala Glu Glu Thr Gly
        35                  40                  45

Cys Val Arg Pro Pro Ala Thr Thr Asp Glu Pro Gly Leu Pro Phe His
    50                  55                  60

Gln Asp Gly Lys Ile Ile His Asn Phe Ile Arg Arg Ile Gln Thr Lys
65                  70                  75                  80

Ile Lys Asp Leu Leu Gln Gln Met Glu Glu Gly Leu Lys Thr Ala Asp
                85                  90                  95

Pro His Asp Cys Ser Ala Tyr Thr Gly Trp Thr Gly Ile Ala Leu Leu
            100                 105                 110

Tyr Leu Gln Leu Tyr Arg Val Thr Cys Asp Gln Thr Tyr Leu Leu Arg
        115                 120                 125

Ser Leu Asp Tyr Val Lys Arg Thr Leu Arg Asn Leu Asn Gly Arg Arg
    130                 135                 140

Val Thr Phe Leu Cys Gly Asp Ala Gly Pro Leu Ala Val Gly Ala Val
145                 150                 155                 160

Ile Tyr His Lys Leu Arg Ser Asp Cys Glu Ser Gln Glu Cys Val Thr
                165                 170                 175
```

```
Lys Leu Leu Gln Leu Gln Arg Ser Val Val Cys Gln Glu Ser Asp Leu
            180                 185                 190

Pro Asp Glu Leu Leu Tyr Gly Arg Ala Gly Tyr Leu Tyr Ala Leu Leu
            195                 200                 205

Tyr Leu Asn Thr Glu Ile Gly Pro Gly Thr Val Cys Glu Ser Ala Ile
210                 215                 220

Lys Glu Val Val Asn Ala Ile Ile Glu Ser Gly Lys Thr Leu Ser Arg
225                 230                 235                 240

Glu Glu Arg Lys Thr Glu Arg Cys Pro Leu Leu Tyr Gln Trp His Arg
                245                 250                 255

Lys Gln Tyr Val Gly Ala Ala His Gly Met Ala Gly Ile Tyr Tyr Met
            260                 265                 270

Leu Met Gln Pro Ala Ala Lys Val Asp Gln Glu Thr Leu Thr Glu Met
        275                 280                 285

Val Lys Pro Ser Ile Asp Tyr Val Arg His Lys Lys Phe Arg Ser Gly
    290                 295                 300

Asn Tyr Pro Ser Ser Leu Ser Asn Glu Thr Asp Arg Leu Val His Trp
305                 310                 315                 320

Cys His Gly Ala Pro Gly Val Ile His Met Leu Met Gln Ala Tyr Lys
                325                 330                 335

Val Phe Lys Glu Glu Lys Tyr Leu Lys Glu Ala Met Glu Cys Ser Asp
            340                 345                 350

Val Ile Trp Gln Arg Gly Leu Leu Arg Lys Gly Tyr Gly Ile Cys His
        355                 360                 365

Gly Thr Ala Gly Asn Gly Tyr Ser Phe Leu Ser Leu Tyr Arg Leu Thr
    370                 375                 380

Gln Asp Lys Lys Tyr Leu Tyr Arg Ala Cys Lys Phe Ala Glu Trp Cys
385                 390                 395                 400

Leu Asp Tyr Gly Ala His Gly Cys Arg Ile Pro Asp Arg Pro Tyr Ser
                405                 410                 415

Leu Phe Glu Gly Met Ala Gly Ala Ile His Phe Leu Ser Asp Val Leu
            420                 425                 430

Gly Pro Glu Thr Ser Arg Phe Pro Ala Phe Glu Leu Asp Ser Ser Lys
        435                 440                 445

Arg Asp
    450

<210> SEQ ID NO 2
<211> LENGTH: 411
<212> TYPE: PRT
<213> ORGANISM: Homo sapiens

<400> SEQUENCE: 2

His His His His His Ser Met Asp Ile Glu Phe Met Ala Gln Arg
1               5                   10                  15

Ala Phe Pro Asn Pro Tyr Ala Asp Tyr Asn Lys Ser Leu Ala Glu Gly
            20                  25                  30

Tyr Phe Asp Ala Ala Gly Arg Leu Thr Pro Glu Phe Ser Gln Arg Leu
        35                  40                  45

Thr Asn Lys Ile Arg Glu Leu Leu Gln Gln Met Glu Arg Gly Leu Lys
    50                  55                  60

Ser Ala Asp Pro Arg Asp Gly Thr Gly Tyr Thr Gly Trp Ala Gly Ile
65                  70                  75                  80

Ala Val Leu Tyr Leu His Leu Tyr Asp Val Phe Gly Asp Pro Ala Tyr
```

85                  90                  95
Leu Gln Leu Ala His Gly Tyr Val Lys Gln Ser Leu Asn Cys Leu Thr
            100                 105                 110

Lys Arg Ser Ile Thr Phe Leu Cys Gly Asp Ala Gly Pro Leu Ala Val
            115                 120                 125

Ala Ala Val Leu Tyr His Lys Met Asn Asn Glu Lys Gln Ala Glu Asp
            130                 135                 140

Cys Ile Thr Arg Leu Ile His Leu Asn Lys Ile Asp Pro His Ala Pro
145                 150                 155                 160

Asn Glu Met Leu Tyr Gly Arg Ile Gly Tyr Ile Tyr Ala Leu Leu Phe
                165                 170                 175

Val Asn Lys Asn Phe Gly Val Glu Lys Ile Pro Gln Ser His Ile Gln
            180                 185                 190

Gln Ile Cys Glu Thr Ile Leu Thr Ser Gly Glu Asn Leu Ala Arg Lys
            195                 200                 205

Arg Asn Phe Thr Ala Lys Ser Pro Leu Met Tyr Glu Trp Tyr Gln Glu
            210                 215                 220

Tyr Tyr Val Gly Ala Ala His Gly Leu Ala Gly Ile Tyr Tyr Tyr Leu
225                 230                 235                 240

Met Gln Pro Ser Leu Gln Val Ser Gln Gly Lys Leu His Ser Leu Val
                245                 250                 255

Lys Pro Ser Val Asp Tyr Val Cys Gln Leu Lys Phe Pro Ser Gly Asn
            260                 265                 270

Tyr Pro Pro Cys Ile Gly Asp Asn Arg Asp Leu Leu Val His Trp Cys
            275                 280                 285

His Gly Ala Pro Gly Val Ile Tyr Met Leu Ile Gln Ala Tyr Lys Val
            290                 295                 300

Phe Arg Glu Glu Lys Tyr Leu Cys Asp Ala Tyr Gln Cys Ala Asp Val
305                 310                 315                 320

Ile Trp Gln Tyr Gly Leu Leu Lys Lys Gly Tyr Gly Leu Cys His Gly
                325                 330                 335

Ser Ala Gly Asn Ala Tyr Ala Phe Leu Thr Leu Tyr Asn Leu Thr Gln
            340                 345                 350

Asp Met Lys Tyr Leu Tyr Arg Ala Cys Lys Phe Ala Glu Trp Cys Leu
            355                 360                 365

Glu Tyr Gly Glu His Gly Cys Arg Thr Pro Asp Thr Pro Phe Ser Leu
            370                 375                 380

Phe Glu Gly Met Ala Gly Thr Ile Tyr Phe Leu Ala Asp Leu Leu Val
385                 390                 395                 400

Pro Thr Lys Ala Arg Phe Pro Ala Phe Glu Leu
                405                 410

<210> SEQ ID NO 3
<211> LENGTH: 450
<212> TYPE: PRT
<213> ORGANISM: Macaca mulatta

<400> SEQUENCE: 3

Met Gly Glu Thr Met Ser Lys Arg Leu Lys Leu His Leu Gly Gly Glu
1               5                   10                  15

Ala Glu Met Glu Glu Arg Ala Phe Ala Asn Pro Phe Pro Asp Tyr Glu
            20                  25                  30

Ala Ala Thr Gly Ala Leu Leu Ala Gly Ala Ala Glu Glu Thr Gly
            35                  40                  45

-continued

```
Cys Val Arg Pro Pro Ala Thr Thr Asp Glu Pro Gly Leu Pro Phe His
    50              55                  60

Gln Asp Gly Lys Ile Ile His Asn Leu Ile Arg Arg Ile Gln Thr Lys
65              70                  75                  80

Ile Lys Asp Leu Leu Gln Gln Met Glu Glu Gly Leu Lys Thr Ala Asp
                85                  90                  95

Pro His Asp Cys Ser Ala Tyr Thr Gly Trp Thr Gly Ile Ala Leu Leu
                100                 105                 110

Tyr Leu Gln Leu Tyr Arg Val Thr Cys Asp Gln Thr Tyr Leu Leu Arg
            115                 120                 125

Ser Leu Asp Tyr Val Lys Arg Thr Leu Arg Asn Leu Asn Gly Arg Arg
130                 135                 140

Val Thr Phe Leu Cys Gly Asp Ala Gly Pro Leu Ala Val Gly Ala Val
145                 150                 155                 160

Ile Tyr His Lys Leu Arg Ser Asp Cys Glu Ser Gln Glu Cys Ile Thr
                165                 170                 175

Lys Leu Leu Gln Leu Gln Arg Ala Val Val Cys Gln Glu Ser Asp Leu
                180                 185                 190

Pro Asp Glu Leu Leu Tyr Gly Arg Ala Gly Tyr Leu Tyr Ala Leu Leu
                195                 200                 205

Tyr Leu Asn Thr Glu Ile Gly Pro Gly Thr Val Cys Glu Ser Ala Ile
210                 215                 220

Lys Glu Val Val Asn Ala Ile Ile Glu Ser Gly Lys Thr Leu Ser Arg
225                 230                 235                 240

Glu Glu Arg Lys Thr Glu Arg Cys Pro Leu Leu Tyr Gln Trp His Arg
                245                 250                 255

Lys Gln Tyr Val Gly Ala Ala His Gly Met Ala Gly Ile Tyr Tyr Met
                260                 265                 270

Leu Met Gln Pro Ala Ala Lys Val Asp Gln Glu Thr Leu Thr Glu Met
            275                 280                 285

Val Lys Pro Ser Ile Asp Tyr Val Arg His Lys Lys Phe Arg Ser Gly
290                 295                 300

Asn Tyr Pro Ser Ser Leu Ser Asn Glu Thr Asp Arg Leu Val His Trp
305                 310                 315                 320

Cys His Gly Ala Pro Gly Val Ile His Met Leu Met Gln Ala Tyr Lys
                325                 330                 335

Val Phe Lys Glu Glu Lys Tyr Leu Lys Glu Ala Met Glu Cys Ser Asp
                340                 345                 350

Val Ile Trp Gln Arg Gly Leu Leu Arg Lys Gly Tyr Gly Ile Cys His
            355                 360                 365

Gly Thr Ala Gly Asn Gly Tyr Ser Phe Leu Ser Leu Tyr Arg Leu Thr
370                 375                 380

Gln Asp Lys Lys Tyr Leu Tyr Arg Ala Cys Lys Phe Ala Glu Trp Cys
385                 390                 395                 400

Leu Asp Tyr Gly Ala His Gly Cys Arg Ile Pro Asp Arg Pro Tyr Ser
                405                 410                 415

Leu Phe Glu Gly Met Ala Gly Ala Ile His Phe Leu Ser Asp Val Leu
                420                 425                 430

Gly Pro Glu Thr Ser Arg Phe Pro Ala Phe Glu Leu Asp Ser Ser Lys
            435                 440                 445

Arg Asp
450
```

-continued

```
<210> SEQ ID NO 4
<211> LENGTH: 450
<212> TYPE: PRT
<213> ORGANISM: Rattus norvegicus

<400> SEQUENCE: 4

Met Gly Glu Thr Met Ser Lys Arg Leu Lys Phe His Leu Gly Glu Ala
1               5                   10                  15

Glu Met Glu Glu Arg Ser Phe Pro Asn Pro Phe Leu Asp Tyr Glu Val
            20                  25                  30

Ala Ala Ser Ala Thr Gly Phe Ala Ser Gly Thr Ala Glu Glu Thr Gly
        35                  40                  45

Arg Val Cys Pro Leu Pro Thr Thr Glu Asp Pro Gly Leu Pro Phe His
50                  55                  60

Pro Asn Gly Lys Ile Val Pro Asn Leu Ile Lys Arg Ile Gln Thr Lys
65                  70                  75                  80

Ile Lys Asp Leu Leu Gln Gln Met Glu Glu Gly Leu Lys Thr Ala Asp
                85                  90                  95

Pro His Asp Cys Ser Ala Tyr Thr Gly Trp Thr Gly Ile Ala Leu Leu
            100                 105                 110

Tyr Leu Gln Leu Tyr Arg Val Thr Gly Asp Gln Thr Tyr Leu Leu Arg
        115                 120                 125

Ser Leu Asp Tyr Val Lys Arg Thr Leu Arg Asn Leu Ser Gly Arg Arg
130                 135                 140

Val Thr Phe Leu Cys Gly Asp Ala Gly Pro Leu Ala Val Gly Ala Val
145                 150                 155                 160

Ile Tyr His Lys Leu Lys Ser Glu Cys Glu Ser Gln Glu Cys Ile Thr
                165                 170                 175

Lys Leu Leu Gln Met His Arg Thr Ile Val Cys Gln Glu Ser Glu Leu
            180                 185                 190

Pro Asp Glu Leu Leu Phe Gly Arg Ala Gly Tyr Leu Tyr Ala Leu Leu
        195                 200                 205

Tyr Leu Asn Thr Glu Ile Gly Pro Gly Thr Val Gly Glu Thr Ala Ile
210                 215                 220

Lys Glu Val Val Thr Ala Ile Ile Glu Ser Gly Lys Arg Leu Ser Arg
225                 230                 235                 240

Glu Glu Arg Lys Ser Glu Arg Cys Pro Leu Leu Tyr Gln Trp His Arg
                245                 250                 255

Lys Gln Tyr Val Gly Ala Ala His Gly Met Ala Gly Ile Tyr Tyr Met
            260                 265                 270

Leu Met Gln Pro Glu Ala Lys Val Asp Gln Glu Thr Leu Thr Glu Met
        275                 280                 285

Val Lys Pro Ser Ile Asp Tyr Val Arg His Lys Lys Phe Arg Ser Gly
290                 295                 300

Asn Tyr Pro Ser Ser Leu Ser Asn Glu Thr Asp Arg Leu Val His Trp
305                 310                 315                 320

Cys His Gly Ala Pro Gly Val Ile His Met Leu Leu Arg Ala Tyr Gln
                325                 330                 335

Val Phe Lys Glu Glu Lys Tyr Leu Lys Glu Ala Met Glu Cys Ser Asp
            340                 345                 350

Val Ile Trp Gln Arg Gly Leu Leu Arg Lys Gly Tyr Gly Ile Cys His
        355                 360                 365

Gly Thr Ala Gly Asn Gly Tyr Ser Phe Leu Ser Leu Tyr Gln Leu Thr
370                 375                 380
```

```
Gln Asp Lys Lys Tyr Leu Tyr Arg Ala Cys Lys Phe Ala Glu Trp Cys
385                 390                 395                 400

Leu Asp Tyr Gly Ala His Gly Cys Arg Ile Pro Asp Arg Pro Tyr Ser
            405                 410                 415

Leu Phe Glu Gly Met Ala Gly Ala Val His Phe Leu Ser Asp Met Leu
        420                 425                 430

Val Pro Glu Thr Ala Arg Phe Pro Ala Phe Glu Leu Gly Phe Val Gln
        435                 440                 445

Lys Asp
    450

<210> SEQ ID NO 5
<211> LENGTH: 399
<212> TYPE: PRT
<213> ORGANISM: Rattus norvegicus

<400> SEQUENCE: 5

Met Ala Gln Arg Ala Phe Pro Asn Pro Tyr Ala Asp Tyr Asn Lys Ser
1               5                   10                  15

Leu Ala Glu Asn Tyr Phe Asp Ser Thr Gly Arg Leu Thr Pro Glu Phe
            20                  25                  30

Ser His Arg Leu Thr Asn Lys Ile Arg Glu Leu Leu Gln Gln Met Glu
        35                  40                  45

Arg Gly Leu Lys Ser Ala Asp Pro Gln Asp Gly Thr Gly Tyr Thr Gly
    50                  55                  60

Trp Ala Gly Ile Ala Val Leu Tyr Leu His Leu His Asn Val Phe Gly
65                  70                  75                  80

Asp Pro Ala Tyr Leu Gln Met Ala His Ser Tyr Val Lys His Ser Leu
                85                  90                  95

Asn Cys Leu Ser Arg Arg Ser Ile Thr Phe Leu Cys Gly Asp Ala Gly
            100                 105                 110

Pro Leu Ala Val Ala Ala Val Leu Tyr His Lys Met Asn Ser Gly Lys
        115                 120                 125

Gln Ala Glu Asp Cys Ile Thr Arg Leu Ile His Leu Asn Lys Ile Asp
    130                 135                 140

Pro His Val Pro Asn Glu Met Leu Tyr Gly Arg Ile Gly Tyr Ile Phe
145                 150                 155                 160

Ala Leu Leu Phe Val Asn Lys Asn Phe Gly Glu Glu Lys Ile Pro Gln
                165                 170                 175

Ser His Ile Gln Gln Ile Cys Glu Thr Ile Leu Thr Ser Gly Glu Lys
            180                 185                 190

Leu Ser Arg Lys Arg Asn Phe Thr Thr Lys Ser Pro Leu Met Tyr Glu
        195                 200                 205

Trp Tyr Gln Glu Tyr Tyr Val Gly Ala Ala His Gly Leu Ala Gly Ile
    210                 215                 220

Tyr Tyr Tyr Leu Met Gln Pro Ser Leu His Val Ser Gln Gly Lys Leu
225                 230                 235                 240

His Ser Leu Val Lys Pro Ser Val Asp Phe Val Cys Gln Leu Lys Phe
                245                 250                 255

Pro Ser Gly Asn Tyr Pro Ser Cys Leu Asp Asp Thr Arg Asp Leu Leu
            260                 265                 270

Val His Trp Cys His Gly Ala Pro Gly Val Ile Tyr Met Leu Ile Gln
        275                 280                 285

Ala Tyr Lys Val Phe Lys Glu Glu His Tyr Leu Cys Asp Ala Gln Gln
    290                 295                 300
```

```
Cys Ala Asp Val Ile Trp Gln Tyr Gly Leu Leu Lys Lys Gly Tyr Gly
305                 310                 315                 320

Leu Cys His Gly Ala Ala Gly Asn Ala Tyr Ala Phe Leu Ala Leu Tyr
            325                 330                 335

Asn Leu Thr Gln Asp Ala Lys Tyr Leu Tyr Arg Ala Cys Lys Phe Ala
        340                 345                 350

Glu Trp Cys Leu Asp Tyr Gly Glu His Gly Cys Arg Thr Pro Asp Thr
    355                 360                 365

Pro Phe Ser Leu Phe Glu Gly Met Ala Gly Thr Ile Tyr Phe Leu Ala
370                 375                 380

Asp Leu Leu Val Pro Thr Lys Ala Lys Phe Pro Ala Phe Glu Leu
385                 390                 395

<210> SEQ ID NO 6
<211> LENGTH: 450
<212> TYPE: PRT
<213> ORGANISM: Mus musculus

<400> SEQUENCE: 6

Met Gly Glu Thr Met Ser Lys Arg Leu Lys Phe His Leu Gly Glu Ala
1               5                   10                  15

Glu Met Glu Glu Arg Ser Phe Pro Asn Pro Phe Pro Asp Tyr Glu Ala
            20                  25                  30

Ala Ala Ser Ala Ala Gly Leu Ala Gly Ser Ala Glu Glu Thr Gly
        35                  40                  45

Arg Val Cys Pro Leu Pro Thr Thr Glu Asp Pro Gly Leu Pro Phe His
    50                  55                  60

Pro Asn Gly Lys Ile Val Pro Asn Phe Ile Lys Arg Ile Gln Thr Lys
65                  70                  75                  80

Ile Lys Asp Leu Leu Gln Gln Met Glu Glu Gly Leu Lys Thr Ala Asp
                85                  90                  95

Pro His Asp Cys Ser Ala Tyr Thr Gly Trp Thr Gly Ile Ala Leu Leu
            100                 105                 110

Tyr Leu Gln Leu Tyr Arg Val Thr Gly Asp Gln Thr Tyr Leu Leu Arg
        115                 120                 125

Ser Leu Asp Tyr Val Lys Arg Thr Leu Arg Asn Leu Ser Gly Arg Arg
    130                 135                 140

Val Thr Phe Leu Cys Gly Asp Ala Gly Pro Leu Ala Val Gly Ala Val
145                 150                 155                 160

Ile Tyr His Lys Leu Lys Ser Glu Cys Glu Ser Gln Glu Cys Ile Thr
                165                 170                 175

Lys Leu Leu Gln Met His Arg Thr Ile Val Cys Gln Glu Ser Glu Leu
            180                 185                 190

Pro Asp Glu Leu Leu Tyr Gly Arg Ala Gly Tyr Leu Tyr Ala Leu Leu
        195                 200                 205

Tyr Leu Asn Thr Glu Ile Gly Pro Gly Thr Val Gly Glu Thr Ala Ile
    210                 215                 220

Lys Glu Val Val Ser Ala Ile Ile Glu Ser Gly Lys Ser Leu Ser Arg
225                 230                 235                 240

Glu Glu Arg Lys Ser Glu Arg Cys Pro Leu Leu Tyr Gln Trp His Arg
                245                 250                 255

Lys Gln Tyr Val Gly Ala Ala His Gly Met Ala Gly Ile Tyr Tyr Met
            260                 265                 270

Leu Met Gln Pro Glu Ala Lys Val Asp Gln Glu Thr Leu Thr Glu Met
```

```
            275                 280                 285
Val Lys Pro Ser Ile Asp Tyr Val Arg His Lys Phe Arg Ser Gly
    290                 295                 300

Asn Tyr Pro Ser Ser Leu Ser Asn Glu Thr Asp Arg Leu Val His Trp
305                 310                 315                 320

Cys His Gly Ala Pro Gly Val Ile His Val Leu Leu Gln Ala Tyr Gln
                325                 330                 335

Val Phe Lys Glu Glu Lys Tyr Leu Lys Glu Ala Met Glu Cys Ser Asp
            340                 345                 350

Val Ile Trp Gln Arg Gly Leu Leu Arg Lys Gly Tyr Gly Ile Cys His
            355                 360                 365

Gly Thr Ser Gly Asn Gly Tyr Ser Phe Leu Ser Leu Tyr Arg Leu Thr
            370                 375                 380

Gln Asp Lys Lys Tyr Leu Tyr Arg Ala Cys Lys Phe Ala Glu Trp Cys
385                 390                 395                 400

Leu Asp Tyr Gly Ala His Gly Cys Arg Ile Pro Asp Arg Pro Tyr Ser
                405                 410                 415

Leu Phe Glu Gly Met Ala Gly Ala Val His Phe Leu Ser Asp Ile Leu
            420                 425                 430

Val Pro Glu Thr Ala Arg Phe Pro Ala Phe Glu Leu Gly Phe Leu Gln
            435                 440                 445

Lys Asp
    450

<210> SEQ ID NO 7
<211> LENGTH: 399
<212> TYPE: PRT
<213> ORGANISM: Mus musculus

<400> SEQUENCE: 7

Met Ala Gln Arg Ala Phe Pro Asn Pro Tyr Ala Asp Tyr Asn Lys Ser
1               5                   10                  15

Leu Ala Glu Asn Tyr Phe Asp Ser Thr Gly Arg Leu Thr Pro Glu Phe
                20                  25                  30

Ser His Arg Leu Thr Asn Lys Ile Arg Glu Leu Leu Gln Gln Met Glu
            35                  40                  45

Arg Gly Leu Lys Ser Ala Asp Pro Arg Asp Gly Thr Gly Tyr Thr Gly
    50                  55                  60

Trp Ala Gly Ile Ala Val Leu Tyr Leu His Leu His Asn Val Phe Gly
65                  70                  75                  80

Asp Pro Ala Tyr Leu Gln Met Ala His Ser Tyr Val Lys Gln Ser Leu
                85                  90                  95

Asn Cys Leu Ser Arg Arg Ser Ile Thr Phe Leu Cys Gly Asp Ala Gly
                100                 105                 110

Pro Leu Ala Val Ala Ala Val Leu Tyr His Lys Met Asn Ser Glu Lys
            115                 120                 125

Gln Ala Glu Glu Cys Ile Thr Arg Leu Ile His Leu Asn Lys Ile Asp
    130                 135                 140

Pro His Val Pro Asn Glu Met Leu Tyr Gly Arg Ile Gly Tyr Ile Phe
145                 150                 155                 160

Ala Leu Leu Phe Val Asn Lys Asn Phe Gly Glu Lys Ile Pro Gln
                165                 170                 175

Ser His Ile Gln Gln Ile Cys Glu Asn Ile Leu Thr Ser Gly Glu Asn
            180                 185                 190
```

```
Leu Ser Arg Lys Arg Asn Phe Ala Ala Lys Ser Pro Leu Met Tyr Glu
            195                 200                 205

Trp Tyr Gln Glu Tyr Tyr Val Gly Ala Ala His Gly Leu Ala Gly Ile
210                 215                 220

Tyr Tyr Tyr Leu Met Gln Pro Ser Leu Gln Val Asn Gln Gly Lys Leu
225                 230                 235                 240

His Ser Leu Val Lys Pro Ser Val Asp Phe Val Cys Arg Leu Lys Phe
                245                 250                 255

Pro Ser Gly Asn Tyr Pro Pro Cys Leu Asp Asp Thr Arg Asp Leu Leu
                260                 265                 270

Val His Trp Cys His Gly Ala Pro Gly Val Ile Tyr Met Leu Ile Gln
275                 280                 285

Ala Tyr Lys Val Phe Lys Glu Glu Arg Tyr Leu Cys Asp Ala Gln Gln
290                 295                 300

Cys Ala Asp Val Ile Trp Gln Tyr Gly Leu Leu Lys Lys Gly Tyr Gly
305                 310                 315                 320

Leu Cys His Gly Ala Ala Gly Asn Ala Tyr Ala Phe Leu Ala Leu Tyr
                325                 330                 335

Asn Leu Thr Gln Asp Leu Lys Tyr Leu Tyr Arg Ala Cys Lys Phe Ala
                340                 345                 350

Glu Trp Cys Leu Asp Tyr Gly Glu His Gly Cys Arg Thr Ala Asp Thr
                355                 360                 365

Pro Phe Ser Leu Phe Glu Gly Met Ala Gly Thr Ile Tyr Phe Leu Ala
                370                 375                 380

Asp Leu Leu Val Pro Thr Lys Ala Lys Phe Pro Ala Phe Glu Leu
385                 390                 395

<210> SEQ ID NO 8
<211> LENGTH: 433
<212> TYPE: PRT
<213> ORGANISM: Bos taurus

<400> SEQUENCE: 8

Met Glu Asp Arg Ala Phe Pro Asn Pro Phe Pro Asp Tyr Glu Ala Ala
1               5                   10                  15

Ala Glu Arg Gln Ala Glu Glu Pro Pro Cys Ser Arg Thr Pro Leu Ser
                20                  25                  30

Pro Glu Glu Leu Gly Leu Pro Phe His Ser Asp Gly Lys Ile Ile Asn
            35                  40                  45

Asn Phe Thr Arg Arg Ile Gln Thr Lys Ile Lys Asp Leu Leu Gln Gln
        50                  55                  60

Met Glu Glu Gly Leu Lys Thr Ala Asp Pro His Asp Cys Ser Ala Tyr
65              70                  75                  80

Thr Gly Trp Thr Gly Ile Ala Leu Leu Tyr Leu Gln Leu Tyr Arg Val
                85                  90                  95

Thr Cys Asp Gln Ser Tyr Leu Leu Arg Ser Leu Asp Tyr Val Lys Arg
                100                 105                 110

Thr Leu Arg Asn Leu Asn Gly Arg Arg Val Thr Phe Leu Cys Gly Asp
            115                 120                 125

Ala Gly Pro Leu Ala Val Gly Ala Val Val Tyr His Lys Leu Lys Ser
130                 135                 140

Asp Cys Glu Ser Gln Glu Cys Ile Thr Lys Leu Leu Gln Leu Gln Arg
145                 150                 155                 160

Thr Ile Val Cys Arg Asp Ser Asp Leu Pro Asp Glu Leu Leu Tyr Gly
                165                 170                 175
```

```
Arg Ala Gly Tyr Leu Tyr Ala Leu Leu Tyr Val Asn Thr Glu Ile Gly
                180                 185                 190

Pro Gly Ala Val Cys Glu Ser Ala Ile Lys Glu Val Asn Ala Ile
            195                 200                 205

Ile Glu Ser Gly Lys Ala Leu Ser Lys Glu Lys Lys Val Glu Arg
210                 215                 220

Cys Pro Leu Leu Tyr Gln Trp His Arg Lys Gln Tyr Val Gly Ala Ala
225                 230                 235                 240

His Gly Met Ala Gly Ile Tyr Tyr Met Leu Met Gln Pro Ala Ala Lys
                245                 250                 255

Val Asp Gln Glu Thr Leu Thr Glu Met Val Lys Pro Ser Ile Asp Tyr
            260                 265                 270

Met Arg His Lys Arg Phe Arg Ser Gly Asn Tyr Pro Ser Ser Leu Ser
            275                 280                 285

Asn Glu Thr Asp Arg Leu Val His Trp Cys His Gly Ala Pro Gly Val
            290                 295                 300

Ile His Val Leu Met Gln Ala His Lys Val Phe Lys Glu Glu Lys Tyr
305                 310                 315                 320

Leu Lys Asp Ala Val Glu Cys Ser Asp Val Ile Trp Gln Arg Gly Leu
                325                 330                 335

Leu Arg Lys Gly Tyr Gly Ile Cys His Gly Thr Ala Gly Asn Gly Tyr
            340                 345                 350

Ser Phe Leu Ser Leu Tyr His Ile Thr Gln Asp Lys Lys Tyr Leu Tyr
            355                 360                 365

Arg Ala Cys Lys Phe Ala Glu Trp Cys Leu Glu Tyr Gly Ala His Gly
            370                 375                 380

Cys Arg Ile Pro Asp Arg Pro Tyr Ser Leu Phe Glu Gly Met Ala Gly
385                 390                 395                 400

Thr Ile His Phe Leu Ser Asp Ile Leu Ala Pro Glu Ala Ser Arg Phe
                405                 410                 415

Pro Ala Phe Glu Leu Ser Ser Ser Gln Arg Asp Thr Lys Val Gln Lys
            420                 425                 430

Asp

<210> SEQ ID NO 9
<211> LENGTH: 399
<212> TYPE: PRT
<213> ORGANISM: Bos taurus

<400> SEQUENCE: 9

Met Ala Gln Arg Ala Phe Pro Asn Pro Tyr Ala Asp Tyr Asn Lys Ser
1               5                   10                  15

Leu Ala Glu Gly Tyr Phe Asp Ser Ala Gly Arg Leu Thr Pro Glu Phe
                20                  25                  30

Ser Gln Arg Leu Asn Asn Lys Ile Arg Glu Leu Leu Gln Gln Met Glu
            35                  40                  45

Arg Gly Leu Lys Ser Ala Asp Pro Arg Asp Ser Thr Val Tyr Thr Gly
        50                  55                  60

Trp Ala Gly Ile Ala Val Leu Tyr Leu His Leu Tyr Asp Val Phe Gly
65                  70                  75                  80

Asp Pro Asn Tyr Leu Gln Met Ala His Gly Tyr Val Lys Gln Ser Leu
                85                  90                  95

Asn Ser Leu Ser Lys His Ser Ile Thr Phe Leu Cys Gly Asp Gly Gly
            100                 105                 110
```

```
Pro Leu Ala Val Ala Val Val His His Lys Met Asn Asn Glu Lys
            115                 120                 125

Gln Ala Glu Glu Cys Ile Thr Arg Leu Ile His Leu Asn Lys Ile Asp
130                 135                 140

Arg His Ala Pro Ser Glu Met Leu Tyr Gly Arg Met Gly Tyr Ile Ser
145                 150                 155                 160

Ala Leu Leu Phe Val Asn Lys Asn Phe Gly Glu Lys Ile Pro Gln
                165                 170                 175

Ser His Ile Gln Gln Ile Cys Glu Thr Val Leu Thr Ser Gly Glu Asp
            180                 185                 190

Leu Ala Arg Lys Arg Arg Phe Thr Gly Glu Thr Pro Leu Met Tyr Glu
            195                 200                 205

Trp Tyr Gln Glu Tyr Tyr Val Gly Ala Ala His Gly Leu Ala Gly Ile
            210                 215                 220

Tyr Tyr Tyr Leu Met Gln Pro Ser Leu Gln Val Ser His Ala Lys Leu
225                 230                 235                 240

His Asn Leu Val Lys Pro Ser Val Asp Tyr Val Cys Gln Leu Lys Phe
                245                 250                 255

Pro Ser Gly Asn Tyr Pro Pro Cys Val Asp Asp Ser Arg Asp Leu Leu
            260                 265                 270

Ile His Trp Cys His Gly Ala Pro Gly Val Ile Tyr Met Leu Thr Gln
            275                 280                 285

Ala Tyr Lys Val Phe Lys Glu Glu Arg Tyr Leu Asn Asp Ala Tyr Gln
            290                 295                 300

Cys Ala Asp Val Ile Trp Gln Tyr Gly Leu Leu Lys Lys Gly Tyr Gly
305                 310                 315                 320

Leu Cys His Gly Thr Ala Gly Asn Ala Tyr Ala Phe Leu Ser Leu Tyr
            325                 330                 335

Ser Leu Thr Gln Asp Ala Lys Tyr Leu Tyr Arg Ala Cys Lys Phe Ala
            340                 345                 350

Glu Trp Cys Leu Asp Tyr Gly Glu His Gly Cys Arg Thr Pro Asp Thr
            355                 360                 365

Pro Phe Ser Leu Phe Glu Gly Met Ala Gly Thr Ile Tyr Phe Leu Ala
            370                 375                 380

Asp Leu Leu Val Pro Thr Lys Ala Arg Phe Pro Ala Phe Glu Leu
385                 390                 395

<210> SEQ ID NO 10
<211> LENGTH: 405
<212> TYPE: PRT
<213> ORGANISM: Danio rerio

<400> SEQUENCE: 10

Met Ser Glu Gln Arg Ala Leu Lys Asn Pro Tyr Pro Asp Tyr Thr Gly
1               5                   10                  15

Leu Gly Cys Ala Gln Asp Leu Phe Asp Met Gln Gly Asn Leu Thr Gln
            20                  25                  30

His Phe Ala Thr Ser Ile Ser Ser Lys Ile Ser Glu Leu Leu Ala Ile
            35                  40                  45

Leu Glu Asn Gly Leu Lys Asn Ala Asp Pro Arg Asp Cys Thr Gly Tyr
        50                  55                  60

Thr Gly Trp Ala Gly Ile Ala Leu Leu Tyr Leu His Leu His Ser Val
65                  70                  75                  80

Phe Gly Asp Pro Thr Phe Leu Gln Arg Ala Leu Asp Tyr Val Asn Arg
```

```
                    85                  90                  95
Ser Leu Arg Ser Leu Thr Gln Arg Trp Val Thr Phe Leu Cys Gly Asp
                100                 105                 110

Ala Gly Pro Leu Ala Ile Ala Ala Val Val Tyr His Arg Leu Gln Lys
            115                 120                 125

His Gln Glu Ser Asp Glu Cys Leu Asn Arg Leu Leu Gln Leu Gln Pro
        130                 135                 140

Ser Val Val Gln Gly Lys Gly Arg Leu Pro Asp Glu Leu Leu Tyr Gly
145                 150                 155                 160

Arg Thr Gly Tyr Leu Tyr Ser Leu Ile Phe Val Asn Gln Gln Phe Gln
                165                 170                 175

Gln Glu Lys Ile Pro Phe Gln Tyr Ile Gln Gln Ile Cys Asp Ala Ile
                180                 185                 190

Leu Glu Ser Gly Gln Ile Leu Ser Gln Arg Asn Lys Ile Gln Asp Gln
            195                 200                 205

Ser Pro Leu Met Tyr Glu Trp Tyr Gln Glu Glu Tyr Val Gly Ala Ala
            210                 215                 220

His Gly Leu Ser Gly Ile Tyr Tyr Tyr Leu Met Gln Pro Gly Leu Val
225                 230                 235                 240

Ala Gly Gln Asp Arg Val Phe Ser Leu Val Lys Pro Ser Val Asn Tyr
                245                 250                 255

Val Cys Gln Leu Lys Phe Pro Ser Gly Asn Tyr Ala Pro Cys Val Gly
            260                 265                 270

Asp Ala Arg Asp Leu Leu Val His Trp Cys His Gly Ser Pro Gly Val
            275                 280                 285

Ile Tyr Met Leu Ile Gln Ala Phe Lys Val Phe Gly Val Arg Gln Tyr
        290                 295                 300

Leu Glu Asp Ala Leu Gln Cys Gly Glu Val Ile Trp Gln Arg Gly Leu
305                 310                 315                 320

Leu Lys Lys Gly Tyr Gly Leu Cys His Gly Ala Ala Gly Asn Ala Tyr
                325                 330                 335

Gly Phe Leu Ala Leu Tyr Lys Ile Thr Gln Asp Pro Lys His Leu Tyr
            340                 345                 350

Arg Ala Cys Met Phe Ala Asp Trp Cys Met Asn Tyr Gly Arg His Gly
        355                 360                 365

Cys Arg Thr Pro Asp Thr Pro Phe Ser Leu Phe Glu Gly Met Ala Gly
        370                 375                 380

Thr Ile Tyr Phe Leu Ala Asp Leu Leu Gln Pro Ala Arg Ala Lys Phe
385                 390                 395                 400

Pro Cys Phe Glu Val
            405
```

LANTHIONINE SYNTHETASE COMPONENT C-LIKE PROTEINS AS MOLECULAR TARGETS FOR PREVENTING AND TREATING DISEASES AND DISORDERS

CROSS-REFERENCE TO RELATED APPLICATION

This application claims the priority or U.S. Provisional Patent Application No. 61/331,086, filed May 4, 2010, which is incorporated herein by reference.

STATEMENT REGARDING FEDERALLY SPONSORED RESEARCH OR DEVELOPMENT

This invention was made with U.S. Government support under Contract No. 1RO1.AT004308-01 awarded by the United States National Institutes of Health. The government has certain rights in the invention.

FIELD OF THE INVENTION

The present invention relates to the field of medical treatments for diseases and disorders. More specifically, the present invention relates to the use of the lanthionine synthetase component C-like (LANCL) proteins as therapeutic targets for novel classes of anti-inflammatory, immune regulatory and antidiabetic drugs.

BACKGROUND OF THE INVENTION

According to estimates from the Centers for Disease Control and Prevention (CDC), about 30% of the United States population is obese and 65% is overweight. One of the major consequences of these high rates is manifested by the increased prevalence of type 2 diabetes mellitus (T2D), a disorder that is characterized by high blood glucose in the context of insulin resistance that progresses towards pancreatic β-cell dysfunction leading to insulin deficiency [1]. There are an estimated 23.6 million people in the U.S. (7.8% of the population) with diabetes, 90% of whom are type 2 diabetics [2]. With prevalence rates doubling between 1990 and 2005, CDC has characterized this increase as an epidemic. In parallel with the obesity and diabetes pandemics, the rates of inflammatory diseases are also growing dramatically worldwide and current anti-inflammatory medications such as nonsteroidal anti-inflammatory drugs (NSAID) have adverse side effects. In light of the rapidly growing need for diabetes and anti-inflammatory products, the industry is now faced with the challenge of finding safe and effective compounds for managing blood glucose levels in diabetic patients and treating chronic inflammatory and infectious diseases.

Current antidiabetic drugs used in the management of T2D elicit important insulin-sensitizing and anti-inflammatory effects. However, side effects associated with using these medications are serious, any of which may limit their use [3]. For example, sulfonylureas, the first widely used oral hypoglycemic medications, cause hypoglycemia [4]; Biguanides are typically reserved for patients experiencing gastrointestinal side effects [5] and TZDs could lead to an increase in the incidence of liver damage and potential liver failure, fluid retention, weight gain and congestive heart failure [6]. Thus, it is critical to discover novel, naturally occurring drugs and nutraceuticals against T2D. A study linked the TZD drug Avandia (GlaxoSmithKline) to a 43 percent increased risk of heart attack. In September of 2010 the U.S. Food and Drug Administration (FDA) significantly restricted the use of Avandia. The European Medicines Agency pulled Avandia off the European market in 2010.

In similar action, current therapies against autoimmune and inflammatory diseases such as NSAID have significant side effects, including immune suppression, which can lead to increase risk of cancer and infections. Thus, there is an urgent need to develop novel therapeutic and prophylactic agents that are more efficacious and safer.

Our team has developed computational and experimental approaches to effectively screen and discover novel classes of compounds for the prevention and treatment diabetes, cardiovascular disease, gut inflammation and inflammation-driven cancer that activate nuclear receptors through a novel mechanism of action. Of note is the discovery of a peroxisome proliferator-activated receptor (PPAR) γ-activating and anti-inflammatory phytohormone, ABA, which is also a potent insulin-sensitizer. PPAR γ is one of three PPAR isoforms (α, δ, and γ) that is a component of an extensive group of transcription factors controlling adipogenesis and glucose homeostasis, and both of these processes directly affect obesity and T2D [7]. ABA is a phytochemical regulating fundamental physiological functions in plants but it can also be endogenously synthesized in mammalian cells, including granulocytes, pancreatic β-cells and monocytes [8].

PPAR γ is required for ABA to induce its full spectrum of effects [9], but our unpublished data indicate that ABA does not bind directly to the ligand-binding domain (LBD) of PPAR γ. Therefore, the complete mechanism of activation of PPAR γ by ABA is unknown. Recently, Sturla and his colleagues provided in vitro results suggesting that the lanthionine synthetase component C-like protein 2 (LANCL2) may mediate ABA signaling in human granulocytes [10]. LANCL2 is a member of the eukaryotic LANCL protein family, which is related to the bacterial lanthionine synthetase component C [11]. We posit that LANCL2 is a target for drugs and nutraceuticals that can be used in the prevention and treatment of diabetes and inflammatory diseases [12].

SUMMARY OF THE INVENTION

The present invention relates to the field of medical treatments for diseases and disorders. More specifically, the present invention relates to the use of the lanthionine synthetase component C-like (LANCL) proteins as therapeutic targets for novel classes of anti-inflammatory, immune regulatory and antidiabetic drugs. This includes but it is not limited to abscisic acid (ABA) (FIG. 1), ABA analogs, benzimidazophenyls, repurposed drugs or drug combinations, including thiazolidinediones (TZDs); naturally occurring compounds such as conjugated diene fatty acids, conjugated triene fatty acids, isoprenoids, and natural and synthetic agonists of peroxisome proliferator-activated receptors that activate this receptor through an alternative mechanism of action involving LANCL2 or other membrane proteins to treat or prevent the common inflammatory pathogenesis underlying type 2 diabetes, atherosclerosis, cancer, some inflammatory infectious diseases such as influenza and autoimmune diseases including but not limited to inflammatory bowel disease (Crohn's disease and Ulcerative colitis), rheumatoid arthritis, multiple sclerosis and type 1 diabetes and other chronic inflammatory conditions.

It is an object of the present invention to provide the three dimensional structure of LANCL2. Homology modeling of human LANCL2 is performed using the crystal structure of human lanthionine synthetase component C-like protein 1 (LANCL1) as a template [13].

It is a further object of the present invention to provide methods for elucidating the location of the potential LBD of LANCL2 for ABA.

It is a further object of the present invention to provide a novel and alternative mechanism by which PPAR γ agonists can elicit their biological effects.

It is a further object of the present invention to provide a novel therapeutic target applicable for virtual screening of novel compounds for the treatment of T2D, inflammatory and autoimmune diseases.

It is a further object of the present invention to provide novel classes of anti-inflammatory, immunoregulatory, anti-infective and anti-diabetic drugs that target LANCLs.

It is a further object of the present invention to provide an integrated platform for computational screening of compound databases and experimental validation in vitro and in vivo.

It is yet a further object of the present invention to provide methods for treating inflammation, diabetes, or obesity by targeting LANCL. The methods involve administering a compound effective for binding LANCL.

BRIEF DESCRIPTION OF THE DRAWINGS

The accompanying drawings, which are incorporated in and constitute a part of this specification, illustrate several embodiments of the invention and together with the written description, serve to explain certain principles and details of embodiments of the invention.

FIG. 2 illustrates the sequence alignment of LANCL2 (*Homo sapiens*) with LANCL1 (*Homo sapiens*) by BLASTp algorithm. The Query is the LANCL2 amino acid sequence, while the Sbjct is the LANCL1 sequence. Identical residues are showed in the line between Query and Sbjct. A plus (+) indicates a conserved substitution.

FIG. 16 illustrates the effect of NSC61610 on macroscopic gross lesion scores for inflammation. The control mice and NSC61610-treated mice were challenged with 2.5% dextran sodium sulfate (DSS) for 7 days. On day 7 mice were euthanized and the colon, spleen, and mesenteric lymph nodes (MLN) were macroscopically scored for inflammation. Data for the colon (A), MLN (B), and spleen (C) are represented as mean±standard error. Statistically significant differences ($P<0.05$) between treatments are indicated with different letter superscripts.

FIG. 17 illustrates the effect of NSC61610 on colon histopathology. The control mice and NSC61610-treated mice were challenged with 2.5% dextran sodium sulfate (DSS) for 7 days. Colonic specimens underwent blinded histological examination and were score (1-4) on epithelial erosion, mucosal wall thickening, and leukocyte infiltration. Data for epithelial erosion (A), mucosal wall thickening (B), and leukocyte infiltration (C) are represented as mean±standard error. Statistically significant differences (P<0.05) between treatments are indicated with different letter superscripts.

FIG. 24 illustrates the effect of tissue-specific PPAR γ deletion and NSC61610 on macroscopic lesions score for inflammation. The control mice and NSC61610-treated mice were challenged with 2.5% dextran sodium sulfate (DSS) for 7 days. On day 7 mice were euthanized and the colon, spleen, and mesenteric lymph nodes (MLN) were macroscopically scored for inflammation. Data for the colon (A), spleen (B), and MLN (C) are represented as mean±standard error. Statistically significant differences (P<0.05) between treatments are indicated with different letter superscripts.

FIG. 27 illustrates the effect of influenza virus infection and NSC61610 on histological lesion scores for lung (i.e., epithelial necrosis (A), perivascular cuffing (B), mucosal and submucosal infiltration (C), and airway infiltration (D)). Mice were infected with pandemic influenza virus H1N1 on day 1. The treated mice received 20 mg/kg NSC61610 by orogastric gavage daily. Data are represented as mean±standard error. Statistically significant differences (P<0.05) between treatments are indicated with different letter superscripts.

DETAILED DESCRIPTION OF THE INVENTION

Figure 1:
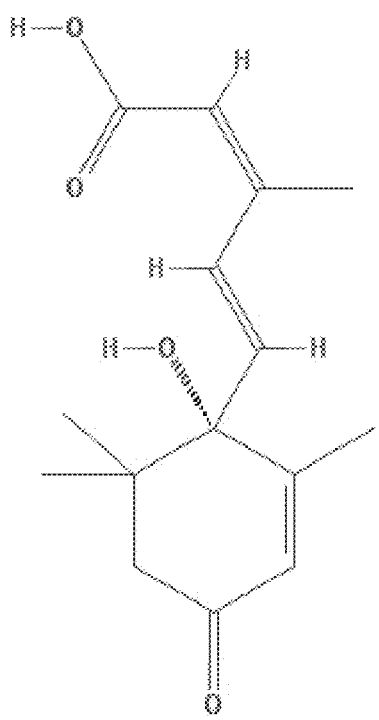
FIG. 1 shows chemical structure of abscisic acid (ABA).

The present inventors have discovered that molecules binding LANCL2, preferably to its extracellular domain, increase PPAR γ activity. That effect allows LANCL2 to be used as a target for the treatment of inflammation, diabetes, or obesity.

In an embodiment, the present invention also provides methods for screening for drug candidates for the treatment of inflammation, diabetes, or obesity. The method comprises contacting an agent with LANCL2. If the agent binds LANCL2, that agent is considered a candidate drug for the treatment of inflammation, diabetes, or obesity; and merits further study and evaluation for safety and effectiveness. The methods are especially useful in high throughput screening for identifying drug candidates, such as the microfluidic system disclosed in U.S. Pat. No. 7,285,411, which is incorporated herein by reference. Other assay formats, such as microarrays for high throughput screening, can also be used.

Binding between LANCL2 and the agent can be determined by methods known in the art, such as by enzyme label, fluorescent label, radioisotope label, etc. In an exemplary screening, LANCL2 is immobilized, for example on the wall of a microfluidic chamber as disclosed in U.S. Pat. No. 7,285,411), and the test agent is fluoresecently labeled. When the test agent is flowed into, then washed out of the microfluidic chamber, binding between the agent and LANCL2 results in a fluorescence in the chamber. If there is no binding, no fluorescence is detected in the chamber. Other methods for detecting receptor/lingand bindings are known in the art, and are disclosed, for example, in U.S. Pat. Nos. 7,482,425; 6,977,141; and 7,887,753, which are incorporated herein by reference.

Assay of the contact between LANCL2 and the test agent need not be performed in vitro. The present invention also contemplates binding determination in silico, which uses computer modeling and simulation to determine the binding between a test agent and LANCL2. Software, such as AutoDock from the Scripts Research Institute, is available to determine how or whether a molecule binds a receptor. An in silico method for determining biding of LANCL2 using AutoDock is demonstrated in the Example. Preferably, when performing in silico binding, agents having lowest binding energies less than about −4.5 kcal/mol are considered drug candidates and are recommended for further testing for safety and effectiveness.

The candidate drugs or agents of the present invention can be, but are not limited to, peptides, small molecules, vitamin derivatives, as well as carbohydrates. Dominant negative proteins, DNA encoding these proteins, antibodies to these proteins, peptide fragments of these proteins or mimics of these proteins may be introduced into the patient to affect function. "Mimic" as used herein refers to the modification of a region or several regions of a peptide molecule to provide a structure chemically different from the parent peptide but topographically and functionally similar to the parent peptide. A skilled artisan can readily recognize that there is no limit as to the structural nature of the candidate drugs or agents of the present invention.

In another embodiment, the present invention relates to methods for affecting the expression of PPAR γ in a cell. In general, the method comprises contacting a cell with an agent effective for binding LANCL2. For example, it can be exposing a cell for a sufficient amount of time for the agent to enter the cell and have an effect on PPAR γ expression or activity. The method can be practiced either in vitro or in vivo. Where practiced in vitro, the method can be used to study the expression of PPAR γ, to test other compounds for the ability to supplement or antagonize the effects of ABA on PPAR γ expression, or for any other reason of importance to a researcher. When practiced in vivo, the method can be used as a method of treating a subject for one or more diseases or disorders associated with PPAR γ expression. It also may be a method of treating a subject that has a predisposition or likelihood of developing a disease or disorder associated with PPAR γ expression. According to the method of this aspect of the invention, preferably, expression of PPAR γ is increased. The step of contacting a cell can be any action that causes the agent to physically contact one or more target cells. Thus, it can be by way of adding the agent directly to an in vitro culture of cells to be contacted, and allowing the agent sufficient time to diffuse through the media and contact at least one cell. Likewise, it can be through addition of the agent to cells in an aqueous environment. Alternatively, it can be by way of administering the agent to a subject via any acceptable administration route, and allowing the body of the subject to distribute the agent to the target cell through natural processes. Thus, the in vivo methods can be methods of localized or systemic delivery of the agent to a cell in animals, including all mammals and humans in particular. According to this aspect, ABA and its related compounds can be used to treat a subject therapeutically or prophylactically, and to prepare a composition for use in treating.

In yet another embodiment, the invention provides a method of treating a subject suffering from or at risk of suffering from a disease or disorder involving PPAR γ expression. In general, the method comprises administering an agent effective for binding LANCL2, in an amount sufficient to affect the amount or activity of PPAR γ in the subject. In certain aspects, the binding of the agent to LANCL2 affects the expression of the PPAR γ gene, resulting in a change in PPAR γ mRNA levels in a cell. In other aspects, the agent affects the amount of PPAR γ protein in a cell, preferably through increase in expression of the PPAR γ gene. In further aspects, the agent affects the activity of the PPAR γ protein in a cell. In preferred embodiments, PPAR γ mRNA expression, PPAR γ-responsive gene expression, such as CD36, AP2 (fatty acid binding protein 4) and adiponectin, protein levels, and/or protein activity is increased in a cell of the treated subject. In general, the method comprises administering a sufficient amount for a sufficient time to see a change in PPAR γ expression or activity. Often, the amount administered and the amount of time is adequate to see a change in one or more clinical symptoms of a disease or disorder, or to stop progression of a disease or disorder from reaching a stage where one or more clinical symptoms are seen. According to this aspect, agent can be used to treat a subject therapeutically or prophylactically, and to prepare a composition for use in treating.

In one embodiment, the present invention provides methods for treating, alleviating, or ameliorating inflammation, diabetes, or obesity. The terms "treating" or "alleviating" or "ameliorating" and similar terms used herein, include prophylaxis and full or partial treatment. The terms may also include reducing symptoms, ameliorating symptoms, reducing the severity of symptoms, reducing the incidence of the disease, or any other change in the condition of the patient, which improves the therapeutic outcome. The methods involve administering to a subject suffering from inflammation, diabetes, or obesity, or a subject in need of treatment for inflammation, diabetes, or obesity, an agent effective to bind LANCL2.

The methods can reduce inflammation systemically (i.e., throughout the subject's body) or locally (e.g., at the site of administration or the site of inflammatory cells, including but not limited to T cells and macrophages). In treating, alleviating, or ameliorating inflammation according to the methods of the present invention, one effect that may be seen is the decrease in the number of macrophages infiltrating the white adipose tissue and skeletal muscle tissue and a down-regulation of tumor necrosis factor-alpha expression.

Thus, according to the methods of the invention, the invention can also provide methods for treatment of diabetes. The methods of treatment can be prophylactic methods. In certain embodiments, the method is a method of treating type 2 diabetes (T2D). In other embodiments, the method is a method of preventing diabetes, such as type 2 diabetes. In embodiments, the method is a method of halting the progression of diabetes, such as type 2 diabetes. In yet other embodiments, the method is a method of improving the health status of a subject suffering from diabetes, such as type 2 diabetes. Accordingly, in embodiments, the invention provides a method of protecting the health, organs, and/or tissues of a subject suffering from diabetes or at risk for developing diabetes.

In one exemplary embodiment of the invention, the method of treating diabetes comprises treating diabetes without causing significant weight gain in the subject being treated. That is, it has been found that the method of treating according to the present invention, which provides the treatment effect, at least in part, by affecting the expression and/or activation of PPAR γ in some cells, provides the beneficial effect without causing a significant gain in weight, for example by fluid retention, in the subject being treated, as compared to other similar subjects not receiving the treatment. While not wishing to be bound by any particular theory as to why this effect is seen, it is likely that treatment with an agent effective to bind LANCL2 causes an increase in PPAR γ expression in certain cells.

In view of the above-mentioned molecular basis for at least part of the effect seen, the present invention provides a method of treating diabetes by the binding of the administered agent with LANCL2 (thereby increasing the expression of PPAR γ in at least a cell of the subject being treated). As with other methods of the invention, the method comprises administering an agent effective to bind LANCL2 to a subject suffering from diabetes, where the ABA is administered in an amount sufficient to bind LANCL2 and to increase the expression, activity, or amount of PPAR γ in at least one cell of the subject. In the method, the cell(s) in which PPAR γ expression, level, or activity is increased can be any cell, from any tissue or organ, in the subject treated. In preferred embodiments, the cell(s) are white adipocyte tissue (WAT) cells, pancreatic cells, or both. In certain treatment methods, the methods do not cause an equivalent increase in PPAR γ expression, level, or activity in liver cells, as compared to the increase seen in WAT and/or pancreatic cells. In embodiments, no detectable increase in PPAR γ mRNA or protein is seen in a liver cell of a subject being treated. One exemplary embodiment of this aspect of the invention is a method of treating diabetes in which expression of PPAR γ is increased in certain cells of the subject, but not other cells, and in which the level of expression is not so high as to cause serious (or, in embodiments, any) noticeable or detectable deleterious effects on the short-term or long-term health of the subject. For instance, uncontrolled over-activation of PPAR γ in the liver could lead to liver injury. In treating diabetes according to the methods of the present invention, one effect that may be seen is an increase in interscapular brown adipose tissue (BAT) mass, which is a positive effect in the context of treatment of diabetes.

In yet another aspect of the invention, a method of lowering glucose levels is provided. The method comprises administering an agent effective to bind LANCL2 to a subject suffering from diabetes or at risk of suffering from diabetes, or otherwise having acute or long-term high glucose levels in blood or tissues. The agent is administered in an amount sufficient to lower the glucose levels in the patient, and especially to lower levels of free glucose in the blood of the subject. Lowering can occur at any time under any physiological condition, but is preferentially seen with regard to the subject's fasting glucose level. In a related method of the invention, a method of increasing the glucose tolerance of a subject is provided. The method comprises the same steps as other methods of the invention, and is similarly based, at least in part, on the underlying mechanisms of action of the binding of the agent to LANCL2, and thus, increasing PPAR γ expression, level, or activity.

Another aspect of the invention provides for effects on cells. These effects can be seen in vitro and in vivo. Certain effects have been discussed above, such as the effects on WAT, pancreatic cells, and BAT. In summary, the effects are to increase the levels of expression of PPAR γ in WAT and pancreatic cells, and to increase the mass of BAT. Additional effects provided by the methods of the invention include reducing the size of certain adipocytes and therefore preventing adipocyte hypertrophy and dysregulation (i.e., insulin resistance). Effects on liver cells and the liver in general are also seen as a result of practicing the methods of the invention. For example, a reduction in lipid accumulation in hepatocytes can be seen as an effect of the treatment (either in vivo administering or in vitro contacting) of the methods of the invention. As an outcome of this effect, the methods also provide a means for reducing the size of the liver of a subject, such as one suffering from diabetes (e.g., type 2 diabetes) or at risk of suffering from diabetes.

The administration of the agent effective to bind LANCL2 can be through any known and acceptable route. Such routes include, but are not necessarily limited to, oral, via a mucosal membrane (e.g., nasally, via inhalation, rectally, intrauterinely or intravaginally, sublingually), intravenously (e.g., intravenous bolus injection, intravenous infusion), intraperitoneally, and subcutaneously. Administering can likewise be by direct injection to a site (e.g., organ, tissue) containing a target cell (i.e., a cell to be treated). Furthermore, administering can follow any number of regimens. It thus can comprise a single dose or dosing of the drug, or multiple doses or dosings over a period of time. Accordingly, treatment can involve repeating the administering step one or more times until a desired result is achieved. In embodiments, treating can continue for extended periods of time, such as weeks, months, or years. Those of skill in the art are fully capable of easily developing suitable dosing regimens for individuals based on known parameters in the art. The methods thus also contemplate controlling, but not necessarily eliminating, the disease or disorder. The preferred routes of administration in accordance with the present invention are oral and via a mucosal membrane.

The amount to be administered varies depending on the subject, stage of the disease, age of the subject, general health of the subject, and various other parameters known and routinely taken into consideration by those of skill in the medical arts. As a general matter, a sufficient amount of the agent will be administered in order to make a detectable change in the symptom of the subject. Suitable amounts are disclosed herein, and additional suitable amounts can be identified by those of skill in the art without undue or excessive experimentation.

The agent is administered in a form that is acceptable, tolerable, and effective for the subject. Numerous pharmaceutical forms and formulations for biologically active agents are known in the art, and any and all of these are contemplated by the present invention. Thus, for example, the agent can be formulated in oral solution, a caplet, a capsule, an injectable, an infusible, a suppository, a lozenge, a tablet, a cream or salve, an inhalant, and the like.

Those of ordinary skill in the art will readily optimize effective dosages and administration regimens as determined by good medical practice and the clinical condition of the individual subject.

The frequency of dosing will depend on the pharmacokinetic parameters of the compounds and the routes of administration. The optimal pharmaceutical formulation will be determined by one of skill in the art depending on the route of administration and the desired dosage. Such formulations may influence the physical state, stability, rate of in vivo release and rate of in vivo clearance of the administered agents. Depending on the route of administration, a suitable dose is calculated according to body weight, body surface areas or organ size. The availability of animal models is particularly useful in facilitating a determination of appropriate dosages of a given therapeutic. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Typically, appropriate dosages are ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions. Those studies, however, are routine and within the level of skilled persons in the art. For example, NSC61610 can be administered at doses ranging from 0.5-6,000 mg per kg of body weight; with dosage ranging from 10-100 mg per kg of body weight being the preferred dosages.

It will be appreciated that the agents, compositions and treatment methods of the invention are useful in fields of human medicine and veterinary medicine. Thus, the subject to be treated is a mammal, such as a human or other mammalian animal. For veterinary purposes, subjects include for example, farm animals including cows, sheep, pigs, horses and goats, companion animals such as dogs and cats, exotic and/or zoo animals, and laboratory animals including mice, rats, rabbits, guinea pigs and hamsters.

The agent effective to bind LANCL2 may be administered to a subject animal, preferably mammals, such as humans, in need thereof as a pharmaceutical or veterinary composition, such as tablets, capsules, solutions, or emulsions. The pharmaceuticals or veterinary compositions appropriate for the present invention can be, but are not limited to, 4-amino-3-[[4-[4-[(1-amino-4-sulfonatonaphthalen-2-yl)diazenyl]phenyl]phenyl]diazenyl]naphthalene-1-sulfonate, Carminomycin, Algestone Acetophenide, Acetyldigitoxins, Aclacur, Digitoxin, Estrone hydrogen sulfate, 4,4'-((2,4-Dihydroxy-5-(hydroxymethyl)-1,3-phenylene)bis(azo))bisnaphthalene-1-sulphonic acid, Idarubicin, Itraconazole, Cefamandole, Pyrvinium, Ketanserin, acetyldigitoxin, Novobiocin, Rolitetracycline, Flubendazole, Norethindrone analog, Convulsants, Cefprozil, Mirtazapine, Bromocriptine, Troglitazone, Mezlocillin, Chlortetracycline, Novobiocin, Rubidazone and 1-N,4-N-bis[3-(1H-benzimidazol-2-yl)phenyl]benzene-1,4-dicarboxamide.

The agent may also be may be present as a nutritional supplement, a nutraceutical, a functional food, or dietary aid, either as a stand-alone ingredient (such as would be seen with sugar, salt, pepper, etc.) or as an ingredient included in the food during processing or packaging. In such situations, the compositions would include at least one agent effective to bind LANCL2 at an appropriate amount for oral ingestion. It is envisioned that this amount would be considerable less, on a gram of product ingested basis, than the amount used for pharmaceutical use in treating inflammation, diabetes, or obesity or prophylactically treating those at risk for developing prediabetes, diabetes, impaired glucose tolerance, and insulin resistance. Agents included in a nutritional supplement, a nutraceutical, a functional food, or dietary aid, include, but are not limited to 3,7-bis(2-oxo-1H-indol-3-ylidene)-1,5-dihydropyrrolo[2,3-f]indole-2,6-dione; 1-amino-3-[(4-amino-9,10-dioxoanthracen-2-yl)amino]anthracene-9,10-dione; benzo[lmn]diquinazolino[2,1-b:2',3'-i][3,8]phenanthroline-5,9,11,19-tetrone; N-1,3-benzothiazol-2-yl-2-[(9-oxo-9H-benzo[c]indolo[3,2,1-ij][1,5]naphthyridin-5-yl)oxy]propanamide; 1-(2-dibenzofuran-3-ylhydrazinyl)-[1]benzofuro[3,2-e]indol-2-one; 2-(2-dibenzofuran-2-ylhydrazinyl)-[1]benzofuro[2,3-f]indol-1-one; 3',11'-Dihydroxy-3H-spiro[2-benzofuran-1,7'-dibenzo[c,h]xanthen]-3-one; [1,4]benzodioxino[2,3-b][1,4]benzodioxino[2',3':5,6]pyrazino[2,3-g]quinoxaline; 6-chloro-3-[(2E)-2-[1-(2-oxochromen-3-yl)ethylidene]hydrazinyl]indol-2-one; and (2Z)-2-(3-oxo-1H-indol-2-ylidene)naphtho[3,2-e][1]benzothiole-1,6,11-trione.

The agents effective for binding LANCL2 can be present in compositions containing other ingredients. Non-limiting examples of compositions appropriate for the present invention are pharmaceutical compositions, such as in the form of tablets, pills, capsules, caplets, multiparticulates (including granules, beads, pellets and micro-encapsulated particles); powders, elixirs, syrups, suspensions, and solutions. Pharmaceutical compositions will typically comprise a pharmaceutically acceptable diluent or carrier. Pharmaceutical compositions are preferably adapted for administration parenterally (e.g., orally). Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the agent on the subject.

Pharmaceutically acceptable carriers suitable for use in such compositions are well known in the art of pharmacy. The compositions of the invention may contain 0.01-99% by weight of the agent. The compositions of the invention are generally prepared in unit dosage form. The excipients used in the preparation of these compositions are well-known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like.

In general, the term carrier may be used throughout this application to represent a composition with which the agent may be mixed, be it a pharmaceutical carrier, foodstuff, nutritional supplement or dietary aid. The materials described above may be considered carriers of the agent for the purposes of the invention. In certain embodiments of the invention, the carrier has little to no biological activity on LANCL2 or PPAR γ.

Without further description, it is believed that one of ordinary skill in the art can, using the preceding description and the following illustrative example, make and utilize the compounds of the present invention and practice the claimed methods. The following example is given to illustrate the present invention. It should be understood that the invention is not to be limited to the specific conditions or details described in this example.

Example

The present invention provides a putative novel target for the discovery and development of drugs and nutraceuticals to treat type 2 diabetes, inflammatory, infectious and autoimmune diseases. In order to understand the function of LANCL2 through its structure and to investigate whether ABA activates LANCL2 via direct binding to its extracellular domain, we performed a western blot assay on RAW 264.7 macrophages without ABA treatment and with ABA treatment. Samples were incubated with rabbit anti-LANCL2 primary antibody and rat anti-ABA primary antibody respectively. Binding between ABA and LANCL2 was also tested in silico. Homology modeling of human LANCL2 was performed using the crystal structure of human LANCL1 as a template [13], assessed the model quality and refined the model through energy minimization procedures. We then used a blind docking approach to elucidate the location of the potential LBD of LANCL2 for ABA. Docking results were evaluated by investigating the interaction of multiple ABA conformations with LANCL2. We also tested whether other synthetic and naturally occurring agonists of PPAR γ could bind to LANCL2 by blind docking. Interestingly, we found that these PPAR γ agonists could bind to the binding region of LANCL2 we propose is occupied by ABA. Among the tested ligands, TZDs and ABA showed the most favorable binding energy, thereby indicating the highest probability of binding to LANCL2.

In order to further understand the function of LANCL2 through its structure and to discover new drugs and nutraceuticals against inflammatory disease and disorders by binding LANCL2, structure-based virtual screening (SBVS) was performed. Thousands of compounds from NCI Diversity Set II, ChemBridge, ZINC natural products, FDA-approved drugs databases and ABA analogs were docked into LANCL2 mode, respectively. All the predicted binding modes were ranked by the calculated affinity. In order to assess the anti-inflammatory efficacy of the top ranked compound in NCI Diversity Set II, the benzimidazophenyl NSC61610, we examined the ability of increasing concentrations of this compound to suppress inflammation and immune cell infiltration in a mouse model of dextran sodium sulfate (DSS)-induced colonic inflammation. Our findings show that compound NSC61610 significantly lowered inflammation in colons of DSS-challenged mice and inhibited adhesion molecule and inflammatory cytokine expression in the colon. These improvements occurred alongside increased numbers of CD4+ FoxP3+ regulatory T cells (Tregs) and CD4+ IL10+ T cells, two subsets of anti-inflammatory T cells, in colon, spleen, mesenteric lymph nodes (MLN), and blood. In addition, compound NSC61610 elevated PPAR γ expression in colon, which suggests that the LANCL2-based anti-inflammatory mechanism may be PPAR γ-mediated. Furthermore, the effect of NSC61610 on the expression of PPAR γ was tested using dual luciferase reporter activity assay. We demonstrated that NSC61610 activated PPAR γ reporter activity in 3T3-L1 pre-adipocytes. In order to explore the anti-inflammatory mechanism of NSC61610, the anti-inflammatory efficacy of NSC61610 was tested in different genotype mouse models of DSS-induced colonic inflammation. We proposed that the anti-inflammatory efficacy of NSC61610 depends on PPAR γ expressed in epithelial and immune cells. Also, we discovered NSC61610 as a potential anti-inflammatory therapy for respiratory virus infections. Thus, our data from pre-clinical efficacy studies and in vitro demonstrate that LANCL2 is a therapeutic target for inflammatory diseases and structure-based virtual screening represents an effective computer-aided drug design (CADD) method for discovering novel LANCL2 agonistic compounds. Furthermore, in order to discover additional efficacy of NSC61610, reverse docking was performed to predict other potential therapeutic targets for NSC61610. Of note this compound was predicted to bind to leukotriene A4 hydrolase and other proteins that may be additional therapeutics targets for NSC61610 and other LANCL2 agonists.

Materials and Methods

Binding Assay Between ABA and LANCL2

RAW 264.7 macrophages were cultured with DMEM (Mediatech, Manassas, Va.) containing 10% fetal bovine serum (FBS) in two flasks and grown until 60-70% confluence. RAW 264.7 macrophages in one flask were treated with abscisic acid (SIGMA-ALDRICH) for 20 minutes. RAW 264.7 macrophages in the other flask without ABA were used as control. Proteins were extracted from Raw 264.7 Macrophage using Radio-Immunoprecipitation Assay buffer (RIPA) (SIGMA-ALDRICH) with inhibitors. 10% SDS-PAGE was applied to analyze the proteins in Bio-Rad mini-gel box running condition. For Western blotting, proteins were electrotransferred to nitrocellulose by standard methods along with the Presicion Plus Kaleidoscope Standard (BIO-RAD). Filters were blocked by 5% BSA in TBS-Tween for 1 hour, followed by incubation with rabbit anti-LANCL2 primary antibody (SIGMA-ALDRICH) in TBS-Tween for 6 hours at room temperature. Goat anti-rabbit horseradish peroxidase-conjugated secondary antibodie (Santa Cruz Biotechnology) was used 1:2,000 in TBS-Tween, and protein bands were detected with Immun-Star™ chemiluminescent substrate (BIO-RAD). Re-probing western blot was applied by incubating nitrocellulose in stripping buffer (Thermo scientific) for 15 minutes. Filters were re-blocked by 5% BSA in TBS-Tween for 1 hour, followed by incubation with rat anti-ABA primary antibody (Abeam) in TBS-Tween for 6 hours at room temperature. Donkey anti-rat horseradish peroxidase-conjugated secondary antibodie (Santa Cruz Biotechnology) was used 1:2,000 in TBS-Tween, and protein bands were detected with Immun-Star™ chemiluminescent substrate (BIO-RAD).

Template Selection and Model Building

Template selection is a critical step in homology modeling. The amino acid sequence of LANCL2 (*Homo sapiens*) was obtained from the protein database at the National Center for Biotechnology Information (NCBI). LANCL2 includes 450 amino acid residues and its accession number is NP_061167. To determine if structural templates in addition to LANCL1 [13] were available, sequence searching was done. BLASTp (protein-protein BLAST) and the BLOSUM62 scoring matrix were applied to search for potential templates for LANCL2 in the non-redundant protein sequence database [14]. Gap existence was penalized 11 from an overall score and each gap extension was deducted 1. Based on this analysis, LANCL1 (*Homo sapiens*) was identified as the only template for modeling LANCL2 (*Homo sapiens*).

To further verify whether LANCL1 is an appropriate template, multiple sequence alignment (MSA) was used to analyze conserved residues and potential sequence motifs of LANCL2. Five target sequences (LANCL2) and five template sequences (LANCL1) from different organisms were selected from the protein database in NCBI. MSA was performed using the CLUSTALW package in Biology Workbench applying the default parameters to insure proper alignment between the template and target [15-16]. The high sequence identity (54%) and sequence similarity (71%) indicate the suitability of LANCL1 as a template for LANCL2 in homology modeling (FIG. 2).

The three-dimensional structure of LANCL2 was constructed by using the SWISS-MODEL Workspace [17]. The template used was the X-ray structure of LANCL1 (2.6 Å resolution. PDB entry code 3E6U) [18].

Model Assessment and Refinement

Model quality was assessed employing two types of assessment tools, ANOLEA [19] and PROCHECK [20]. Local quality model estimation (ANOLEA) describes the quality of different fragments of the same model. Energies of each residue were calculated based on an atomic empirical mean force potential. The stereochemical check (PROCHECK) was applied to determine if the $\phi$ and $\psi$ dihedral angles were in available zones of the Ramachandran plot.

After initial model assessment, an energy minimization (EM) procedure was carried out with the GROMACS 4.0.5 software suite using an all-atom force field (OPLS-AA) [21-22]. The purpose of an EM procedure is to reduce steric clashes in the input structure and to obtain lower potential energy in the system and therefore a more stable structure. The EM algorithm used was steepest descent minimization [23]. The maximum force to stop minimization, energy step size and maximum number of minimization steps to perform were set to 1000 KJ/mol/nm, 0.01 and 50000, respectively. The final LANCL2 model was superimposed on the crystal structure of LANCL1 to check the structural differences between the homology model and template by using RAPIDO program [24].

Ligand Structure

The three-dimensional structure of ABA was downloaded from PubChem, a database of chemical molecules maintained by the NCBI [25]. The compound ID of ABA is 5280896 and its molecular formula is $C_{15}H_{20}O_4$.

Molecular Docking

The docking of ABA into the LANCL2 model was performed with AutoDock (version 4.2) [26]. AutoDockTools, the graphical front-end for AutoDock and AutoGrid, was used to set up, run and analyze AutoDock dockings. The Lamarckian Genetic Algorithm (LGA) was used in AutoDock as the search method to perform automated molecular dockings [27]. Default parameters were applied, except for the number of GA runs, population size and maximum number of evaluations, which were set to 100, 250 and 25,000,000, respectively.

In order to identify potential binding sites of ABA on LANCL2, the docking procedure was performed in two steps. At first, the docking was applied to the whole protein target, with a grid covering the whole surface of the protein. AutoDock can be used when the location of the binding site is unknown. This is often referred to as "blind docking", when all that is known is the structure of the ligand and the macromolecule [28-33]. To search the entire surface of the protein of interest, very large grid maps were created using AutoGrid, with the maximum number of points in each dimension. The grid was a 126 Å cube with grid points separated by 0.59 Å and centered at the middle of the protein. This grid was big enough to cover the entire surface of LANCL2. Then the preliminary dockings with AutoDock were performed to search for particular regions of LANCL2 that were preferred by ABA. In the second round of docking, smaller grids were built around potential binding sites. The X, Y, Z dimensions of grid were set to 70 Å with grid points separated by 0.375 Å.

Analyzing Results of Docking

The search for the best ways to fit ABA into LANCL2 using AutoDock resulted in docking log files that contained detailed records of docking. These log files were read into ADT to analyze the results of docking. The similarity of docked structures was measured by computing the root-mean-square-deviation, RMSD, between the coordinates of the atoms and creating clustering of the conformations based on these RMSD values. In most cases the first cluster was also the largest cluster found. The lowest binding energy conformation in the first cluster was considered as the most favorable docking pose. Binding energies that are reported represent the sum of the total intermolecular energy, total internal energy and torsional free energy minus the energy of the unbound system.

Virtual Screening

The docking of compounds available in NCI Diversity Set II, ChemBridge, ZINC natural products and FDA-approved drugs databases into LANCL2 model was performed with AutoDock Vina (version 1.0) [34]. AutoDockTools, the graphical front-end for AutoDock and AutoGrid, was used to define the search space, including grid box center, spacing between grid points and numbers of points in x,y,z-dimensions [35]. A variety of stochastic global optimization approaches were used in AutoDock Vina, including genetic algorithms, particle swarm optimization, simulated annealing and others. Five bound conformations were generated by AutoDock Vina for each compound.

The docking was applied to the whole protein target, with a grid covering the whole surface of the protein. To search the entire surface of the protein of interest, very large grid maps were set, with the maximum spacing between grid points. The grid was a rectangular cuboid (70 Å×70 Å×60 Å) with grid points separated by 1.000 Å and centered at the middle of the protein. This grid was big enough to cover the entire surface of LANCL2.

Analyzing Results of Virtual Screening

The search for the best way to fit each compound into LANCL2 using AutoDock Vina resulted in docking log files that contained detailed records of docking. These log files include the binding energy of each predicted binding mode for all the compounds in kcal/mol. Binding energies that are reported represent the sum of the total intermolecular energy, total internal energy and torsional free energy minus the energy of the unbound system. For each compound, the root-mean-square-deviation (RMSD) between the coordinates of the atoms were calculated relative to the best mode and used only movable heavy atoms. Two variants of RMSD metrics were provided, RMSD/lb (RMSD lower bound) and RMSD/ub (RMSD upper bound), differing in how the atoms were matched in the distance calculation. RMSD/ub matches each atom in one conformation with itself in the other conformation, ignoring any symmetry. RMSD/lb matches each atom in one conformation with the closest atom of the same element type in the other conformation. All predicted binding models were placed into one multimodel PDBQT file specified by default, base on the ligand file name.

Animal Procedures

Six to eight week old C57BL/6J wild-type mice (n=38) were housed at the animal facilities at Virginia Tech. in a room maintained at 75° F., with a 12:12 h light-dark cycle starting from 6:00 AM. Mice were randomly divided into four groups: a control group including 8 mice and the other three NSC61610 treatment groups containing 10 mice each. The three treatment groups received 0.5, 10 or 20 mg/kg NSC61610 by orogastric gavage for 7 days. All the mice were challenged with drinking water containing 2.5% DSS, 36,000-44,000 molecular weight (ICN Biomedicals, Aurora, Ohio) for 7 days. Mice were weighed on a daily basis and examined for clinical signs of disease associated with colitis (i.e., perianal soiling, rectal bleeding, diarrhea, and piloerection). For the DSS challenge, the disease activity indices and rectal bleeding scores were calculated using a modification of a previously published compounded clinical score. Briefly, disease activity index consisted of a scoring for diarrhea and lethargy (0-3), whereas rectal bleeding consisted of a visual observation of blood in feces and the perianal area (0-4). Mice in the DSS study were euthanized on day 7 of the DSS challenge. On day 7, mice were euthanized by $CO_2$ narcosis followed by secondary thoracotomy and blood was withdrawn from the heart. Colon, spleen, and MLN were scored based on size and macroscopic inflammatory lesions (0-3), excised, and then crushed to produce single-cell suspensions for flow cytometry.

Histopathology

Colonic sections were fixed in 10% buffered neutral formalin, later embedded in paraffin, and then sectioned (5 mm) and stained with H&E stain for histological examination. Colons were blindly graded with a compounded histological score including the extent of (1) leukocyte infiltration, (2) mucosal thickening, and (3) epithelial cell erosion. The sections were graded with a score of 0-4 for each of the previous categories and data were analyzed as a normalized compounded score.

Quantitative Real-Time Reverse-Transcription-PCR

Total RNA was isolated from colons using the RNA isolation Minikit (Qiagen) according to the manufacturer's instructions. Total RNA (1 mg) was used to generate complementary DNA (cDNA) template using the iScript cDNA Synthesis Kit (Bio-Rad, Hercules, Calif.). The total reaction volume was 20 µL with the reaction incubated as follows in an MJ MiniCycler: 5 min at 25° C., 30 min at 52° C., 5 min at 85° C., and hold at 4° C. PCR was performed on the cDNA using Taq DNA polymerase (Invitrogen, Carlsbad, Calif.) and using previously described conditions. Each gene amplicon was purified with the MiniElute PCR Purification Kit (Qiagen) and quantitated on an agarose gel by using a DNA mass ladder (Promega). These purified amplicons were used to optimize real-time (RT)-PCR conditions and to generate standard curves. Primer concentrations and annealing temperatures were optimized for the iCycler iQ system (Bio-Rad) for each set of primers using the system's gradient protocol. PCR efficiencies were maintained between 92 and 105% and correlation coefficients above 0.98 for each primer set during optimization and also during the real-time PCR of sample DNA.

Complementary DNA (cDNA) concentrations for genes of interest were examined by real-time quantitative PCR using an iCycler IQ System and the iQ SYBR green supermix (Bio-Rad). A standard curve was generated for each gene using 10-fold dilutions of purified amplicons starting at 5 pg of cDNA and used later to calculate the starting amount of target cDNA in the unknown samples. SYBR green I is a general double-stranded DNA intercalating dye and may therefore detect non-specific products and primer/dimers in addition to the amplicon of interest. In order to determine the number of products synthesized during the real-time PCR, a melting curve analysis was performed on each product. Real-time PCR was used to measure the starting amount of nucleic acid of each unknown sample of cDNA on the same 96-well plate. Results are presented as starting quantity of target cDNA (picograms) per microgram of total RNA. Primer sequences and Genebank accession numbers are outlined in Table 1.

TABLE 1

Oligonucleotide sequences for quantitative real-time PCR.

| Primer | Sequence | Accession Number |
|---|---|---|
| β-actin Forward | 5' CCCAGGCATTGCTGACAGG3' | X03672 |
| β-actin Reverse | 5' TGGAAGGTGGACAGTGAGGC3' | X03672 |
| PPAR γ Forward | 5' AGAACCTGCATCTCCACCTT3' | NM_011146 |
| PPAR γ Reverse | 5' ACAGACTCGGCACTCAATGG3' | NM_011146 |
| IL-6 Forward | 5' TTTCCTCTGGTCTTCTGGAG3' | NM_031168 |
| IL-6 Reverse | 5' CTGAAGGACTCTGGCTTTGT3' | NM_031168 |
| MCP-1 Forward | 5' CTTTGAATGTGAAGTTGACCC3' | NM_011333 |
| MCP-1 Reverse | 5' AGGCATCACAGTCCGAGTC3' | NM_011333 |
| TNF-α Forward | 5' AGGCATCACAGTCCGAGTC3' | NM_013693 |
| TNF-α Reverse | 5' AGGCATCACAGTCCGAGTC3' | NM_013693 |

Immunophenoptying of Cells Derived from Colon, Blood, Spleen, and MLN

Colonic lamina proprial lymphocytes (LPL) were isolated from digested colons. Spleens and MLNs were excised and single cell suspensions were prepared. Splenocytes were freed of red blood cells with erythrocyte lysis buffer, and spleen and MLN were resuspended in PBS and enumerated with a Coulter Counter (Beckman Coulter, Fullerton, Calif.). LPL, spleen and MLN-derived cells ($2 \times 10^5$ cells/well) or whole blood (10 µL/well) were seeded onto 96-well plates, centrifuged at 4° C. at 3000 rpm for 4 min, and washed with PBS containing 5% serum and 0.09% sodium azide (FACS buffer). To assess differential monocyte/macrophage infiltration, the cells were then incubated in the dark at 4° C. for 20 min in FcBlock (20 µg/ml, BD Pharmingen) for macrophage assessment, and then for an additional 20 min with fluorochrome-conjugated primary antibodies anti-F4/80-PE-Cy5 (0.2 mg/mL, ebioscience) and anti-CD11b-Alexa Fluor 700 (0.2 mg/mL, BD Pharmingen). For lymphocyte subset assessment, cells were incubated with anti-CD45-APC-Cy7 (for LPL only) (0.2 mg/mL, BD Pharmingen), anti-CD4-PE-Cy7 (0.2 mg/mL, BD Pharmingen), anti-CD8-PerCp-Cy5.5 (0.2 mg/mL, eBioscience), anti-CD3-PE-Cy5 (0.2 mg/mL, ebioscience), anti-FoxP3-APC (0.2 mg/mL, eBioscience), and anti-IL10-FITC (0.5 mg/mL, BD Pharmingen). Flow results were computed with a BD LSR 11 flow cytometer and data analyses were performed with FACS Diva software (BD).

Combined Effect of ABA and Rosiglitazone on LANCL2 Expression

To obtain stromal vascular cells (SVCS), abdominal adipose tissue from db/db mice was excised, weighed, minced into small <10 mg pieces and placed into digestion media (1×HBSS (Mediatech, Herndon, Va.) supplemented with 2.5% HEPES (Mediatech) and 10% fetal bovine serum containing type II collagenase (0.2%, Sigma-Aldrich). Samples were incubated in a 37° C. incubator for 30 minutes, filtered through a 100 μm nylon cell strainer to remove undigested particles, and centrifuged at 4° C. at 1000×g for 10 minutes. The pellet, consisting of SVCS, was washed with 1×HBSS and centrifuged at 4° C. at 1000×g for 10 minutes. The supernatant was discarded and erythrocytes were lysed by incubating the SVCs in 2 mL erythrocyte lysis buffer for 2 minutes before stopping the reaction with 9 mL 1×PBS. Cells were then respun at 4° C. at 1000×g for 10 minutes, suspended in 1 ml of IX PBS, and counted with a Coulter Counter (Beckman Coulter, Fullerton, Calif.).

Isolated cells from the stromal vascular fraction (SVF) were seeded into 24-well plates at $2×10^6$ cells/well. Cells were then treated for 6 hrs at 3° C. with LPS (100 ng/mL) in addition to ABA (10 μM), Rosiglitazone (1 μM), ABA and Rosiglitazone, or vehicle alone (DMSO). After incubation cells were harvested with RLT lysis buffer and stored in −80° C. for RNA isolation and gene expression analyses.

PPAR γ Reporter Activity Assays on 3T3-L1 Pre-Adipocytes

3T3-L1 cells were plated into white, opaque 96-well plates (BD) 24 hours before transfection and grown in DMEM containing 10% fetal bovine serum (FBS) until 70% confluence. Cells were then co-transfected with 0.2 μg pCMX.P-PAR γ expression plasmid expression plasmid, 0.2 μg pTK.PPRE3x luciferase reporter plasmid driven by the PPRE-containing Acyl-CoA oxidase promoter and 0.2 μg pRL reporter control using the Lipofectamine 2000 transfection reagent (Invitrogen). After 48 hr incubation at 37° C., cells were then treated in replicates of 8 with NSC61610 2.5 μM or DMSO control and incubated for 24 hr at 37° C. After incubation, cells were harvested in reporter lysis reagent and luciferase activity was determined using the Dual Luciferase II reporter assay system (Promega, Madison, Wis.) in Modulus 96-well luminometer (Turner Biosystems, Sunnyvale, Calif.). All values were normalized to control wells to calculate relative luciferase activity.

Immunoregulatory Mechanisms of NSC61610 in Mice with Experimental IBD

PPAR γ fl/fl MMTV-Cre− (n=20), tissue-specific PPAR γ fl/fl CD4-Cre+ (hemopoietic and epithelial cell-deficient) PPAR γ null mice (n=20) and tissue-specific PPAR γ fl/fl Lsozyme M-Cre+ (macrophage-deficient) PPAR γ null mice (n=20) littermates in a C57BL/6J background were generated by using the Cre-lox recombination system as previously described. The mice were housed at the animal facilities at Virginia Tech. in a room maintained at 75° F., with a 12:12 h light-dark cycle starting from 6:00 AM. In each group, 20 mice were randomly divided into two groups: a control group including 10 mice and a NSC61610 treatment groups containing 10 mice respectively. The three treatment groups received 20 mg/kg NSC61610 by orogastric gavage for 6 days. All the mice (n=60) were challenged with drinking water containing 2.5% DSS, 36,000-44,000 molecular weight (ICN Biomedicals, Aurora, Ohio) for 6 days. Mice were weighed on a daily basis and examined for clinical signs of disease associated with colitis (i.e., perianal soiling, rectal bleeding, diarrhea, and piloerection). For the DSS challenge, the disease activity indices and rectal bleeding scores were calculated using a modification of a previously published compounded clinical score. Briefly, disease activity index consisted of a scoring for diarrhea and lethargy (0-3), whereas rectal bleeding consisted of a visual observation of blood in feces and the perianal area (0-4). Mice in the DSS study were euthanized on day 6 of the DSS challenge. On day 6, mice were euthanized by $CO_2$ narcosis followed by secondary thoracotomy and blood was withdrawn from the heart. Colon, spleen, and MLN were scored based on size and macroscopic inflammatory lesions (0-3), excised, and then crushed to produce single-cell suspensions for flow cytometry.

Anti-Inflammatory Efficacy of NSC61610 Against Respiratory Virus Infections

PPAR γ fl/fl MMTV-Cre− (n=31) and tissue-specific PPAR γ fl/fl MMTV-Cre+ (epithelial and immune cell-deficient) PPAR γ null mice (n=31) in a C57BL/6J background were generated by using the Cre-lox recombination system as previously described. The mice were housed at the animal facilities at Virginia Tech. in a room maintained at 75° F., with a 12:12 h light-dark cycle starting from 6:00 AM. All the mice were divided into eight groups: 1) PPAR γ fl/fl MMTV-Cre− control non-infected mice (n=3); 2) PPAR γ fl/fl MMTV-Cre− treated non-infected mice (n=3); 3) PPAR γ fl/fl MMTV-Cre+ control non-infected mice (n=3); 4) PPAR γ fl/fl MMTV-Cre+ treated non-infected mice (n=3); 5) PPAR γ fl/fl MMTV-Cre− control infected mice (n=12); 6) PPAR γ fl/fl MMTV-Cre− treated infected mice (n=13); 7) PPAR γ fl/fl MMTV-Cre+ control infected mice (n=12); 8) PPAR γ fl/fl MMTV-Cre+ treated infected mice (n=13). Mice were infected with pandemic 2009 H1N1 influenza A California/09 virus at a dose of $10^3$ TCID50 on day 1 of the study. All the treated mice received 20 mg/kg NSC61610 by orogastric gavage daily. Mice were weighed on a daily basis. On day 7, all the non-infected mice and most of infected mice were euthanized by $CO_2$ narcosis followed by secondary thoracotomy and blood was withdrawn from the heart. Lungs were scored based on the extent of lung congestion and hyperemia. In order to further assess the anti-inflammatory efficacy of NSC61610 as immunotherapy for pandemic swine-origin H1N1 influenza virus infection, lungs were blindly graded with a compounded histological score including the extent of 1) epithelial necrosis, 2) perivascular cuffing, 3) mucosa and submucosa infiltration, and 4) terminal airway infiltration. In each infected mice group, five mice were kept to continue monitoring the effect of NSC61610 treatment on influenza-related weight loss. Ex vivo antigen-recall responses to live Influenza A/California/09 virus were assessed in splenocytes at day 13 post-infection. Cells were cultured at $0.2×10^6$ cells were stimulated in U-bottom 96-well plates with cRPMI only, or cRPMI with live virus at 1, 0.5 or 0.1 multiplicity of infection (MOI). All treatments were set in triplicate. On day 4 of the assay, cells were pulsed with 0.5 μCi [$^3$H]-Thymidine and they were harvested at 20 h post-pulsing. Proliferation in the last 20 hours was estimated as a function of thymidine incorporation into cells, which was measured in a β-particle counter. Results are presented as counts per minute (c.p.m.).

Reverse Docking NSC61610 to Potential Drug Target Data

Potential drug target database (PDTD) is a dual function database that associates an informatics database to a structural database of known and potential drug targets. PDTD is a comprehensive, web-accessible database of drug targets, and focuses on those drug targets with known 3D-structures. The target proteins collected in PDTD were selected from the literature, and from several online databases, such as DrugBank and Therapeutic Targets Database (TTD). PDTD contains 1207 entries covering 841 known and potential drug targets with structures from the Protein Data Bank (PDB).

Drug targets of PDTD were categorized into 15 and 13 types according to two criteria: therapeutic areas and biochemical criteria [36].

Target Fishing Dock (TarFisDock) is a web-based tool for seeking potential binding proteins for a given ligand. It applies a ligand-protein reverse docking strategy to search out all possible binding proteins for a small molecule from the PDTD [37]. The reverse docking procedure is as follows: 1) The NSC61610 structure file was downloaded from PubChem (SID 109036). Chimera optimized the NSC61610 structure and saved it in standard mol2 format. 2) TarFisDock docked NSC61610 into the possible binding sites of proteins in the target list. The interaction energies between the small molecule and the proteins were calculated and recorded.

Statistics

Data were analyzed as a completely randomized design. To determine the statistical significance of the model, analysis of variance (ANOVA) was performed using the general linear model procedure of Statistical Analysis Software (SAS), and probability value (P) <0.05 was considered to be significant. When the model was significant, ANOVA was followed by multiple comparison method to identify pairwise treatments with significant difference.

Results and Discussion

Binding Assay Between ABA and LANCL2

Figure 3:
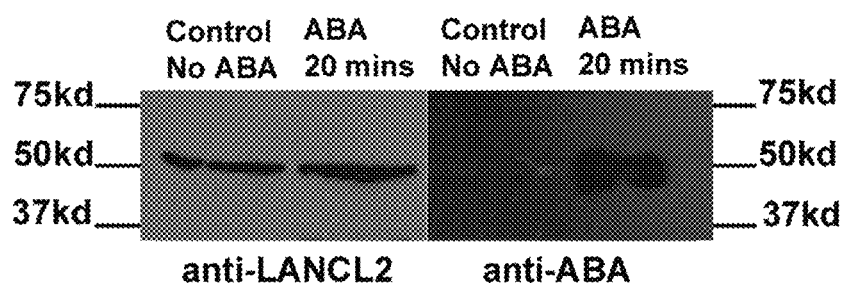
FIG. 3 illustrates the western blot results of RAW 264.7 macrophages without ABA treatment and with ABA treatment. 10% SDS-PAGE was applied to analyze the proteins. Nitrocellulose membrane was incubated with rabbit anti-LANCL2 primary antibody (SIGMA-ALDRICH) and rat anti-ABA primary antibody (Abcam) respectively. Protein bands were detected with Immun-Star™ chemiluminescent substrate (BIO-RAD).

To examine whether ABA binds to LANCL2 directly, two western blots were performed. Firstly, anti-LANCL2 antibody was used to locate the LANCL2 protein on nitrocellulose membrane. FIG. 3 shows that both control and ABA treated samples have one band around 50 kDa while it has been known that the molecular weight of LANCL2 is 50.7 kDa. In the re-probing western blot, the nitrocellulose membrane was incubated with rat anti-ABA primary antibody. The different results appeared between control and ABA treated samples. ABA treated sample showed a clear band in the same location on the nitrocellulose membrane, while the sample without ABA treatment showed no band on the membrane. This experiment provided the direct evidences to verify the binding between ABA and LANCL2 that verified our prediction from molecular docking (FIG. 3).

Template Search

Homology modeling relies on establishing an evolutionary relationship between the sequence of a protein of interest and other members of the protein family, whose structures have been solved experimentally by X-ray crystallography or NMR. For this reason, the major limitation of this technique is the availability of homologous templates. In most cases, two proteins with more than 35% sequence identity are likely to be homologous [35]. The crystal structure of human LANCL1 (3E6U), which shares 54% sequence identity with LANCL2, has been reported by Zhang and colleagues [13].

Figure 4:
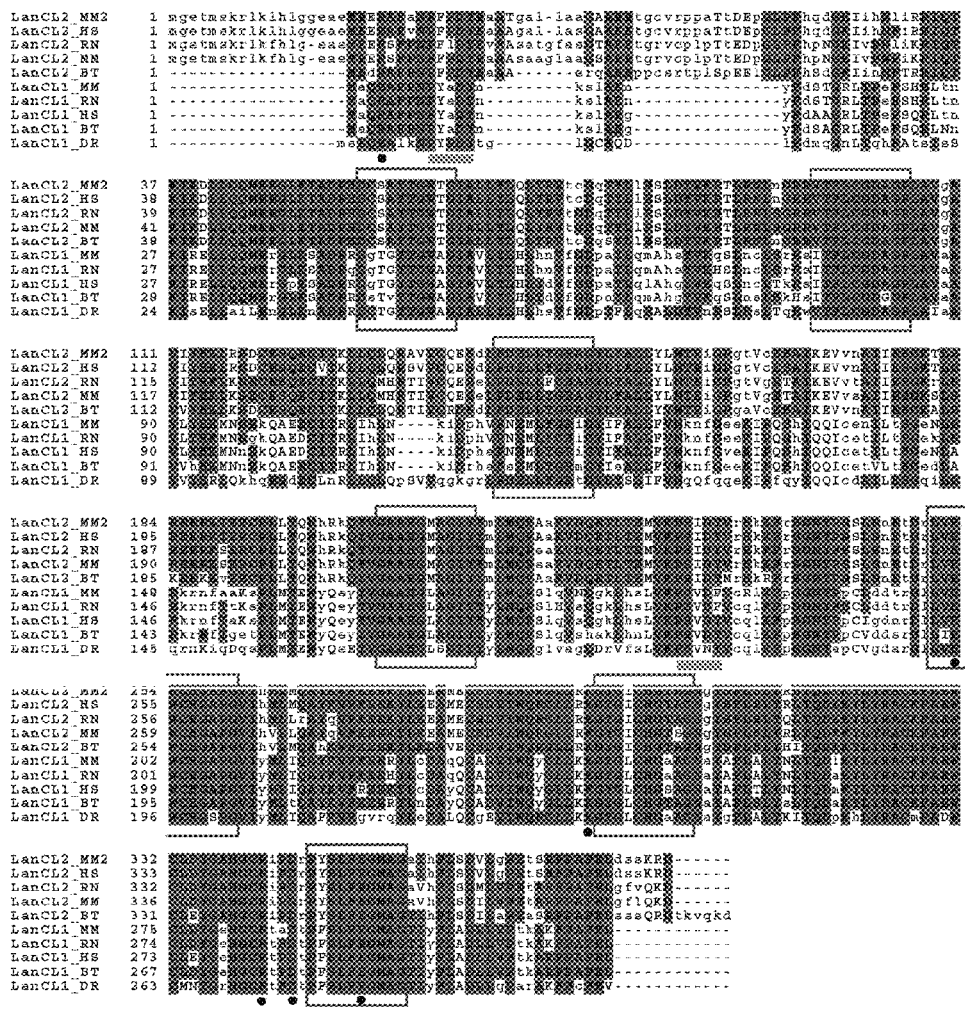
FIG. 4 illustrates multiple sequence alignment of selected LanC proteins. LANCL2_MM2: *Macaca mulatta*; LANCL2_HS: *Homo sapiens*; LANCL2_RN: *Rattus norvegicus*; LANCL2_MM: *Mus musculus*; LANCL2BT: *Bos taurus*; LANCL1_MM: *Mus musculus*; LANCL1_RN: *Rattus norvegicus*; LANCL1_HS: *Homo sapiens*; LANCL1_BT: *Bos taurus*; LANCL1_DR: *Danio rerio*. Completely conserved residues in the listed sequences are highlighted with a red background. Identical residues are highlighted with a magenta background. Different residues are shown in lowercase letters. Seven conserved GxxG motifs and corresponding loop bulges are outlined by blue boxes. Canonical SH3-binding motifs are underlined with green lines. Positions of GSH-binding residues in LANCL1 are denoted by black dots.

To further verify whether functionally important residues and motifs are conserved, multiple sequence alignment was performed between five LANCL1 and five LANCL2 sequences from different organisms (FIG. 4). The alignment showed all LANCL2 sequences also had seven conserved GxxG motifs similar to LANCL1. These seven conserved GxxG-containing motifs are considered to be a signature feature of the LANCL family of proteins because they are absent in other double helix barrel proteins [13]. Furthermore, canonical SH3-binding motifs and GSH-binding residues of LANCL1 also appeared to be highly conserved in the five LANCL2 sequences. All of these findings suggest that LANCL1 and LANCL2 are not only conserved in terms of sequence but are also functionally similar, thus homology modeling of LANCL2 using the LANCL1 structure as template is appropriate.

Model Building

Figure 5:
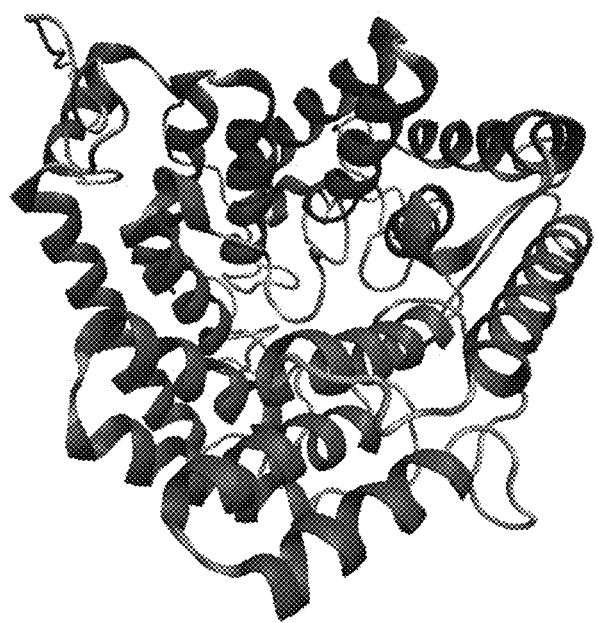
FIG. 5 illustrates the overall structure of LANCL2. The homology model of human LANCL2 is shown in New Cartoon representation with coloring according to secondary structure. Purple: alpha helix; Blue: other helix; Yellow: bridge_beta; Cyan: turn; Green: coil. The image was rendered in VMD.

SWISS-MODEL Workspace was used to generate the homology model of LANCL2 according to the crystal structure of LANCL1 [17]. As expected, the predicted structure of LANCL2 consists of two layers of α-helical barrels consisting of 14 α-helices. The outer barrel is formed by seven helices that are parallel to one another, while the inner barrel is formed by seven helices that are also parallel to one another. The orientation of the two layer barrel helices is opposite, but both inner and outer barrels have a left-handed twist. The seven conserved GxxG-containing bulges are at the N-termini of the inner helices. These bulged loops reduce the entry size of the central cavity formed by the inner helix barrel. Therefore, LANCL2 is unlikely to use the central cavity as a ligand binding site. The structure of LANCL2 is shown in FIG. 5.

Model Assessment and Refinement

Figure 6:
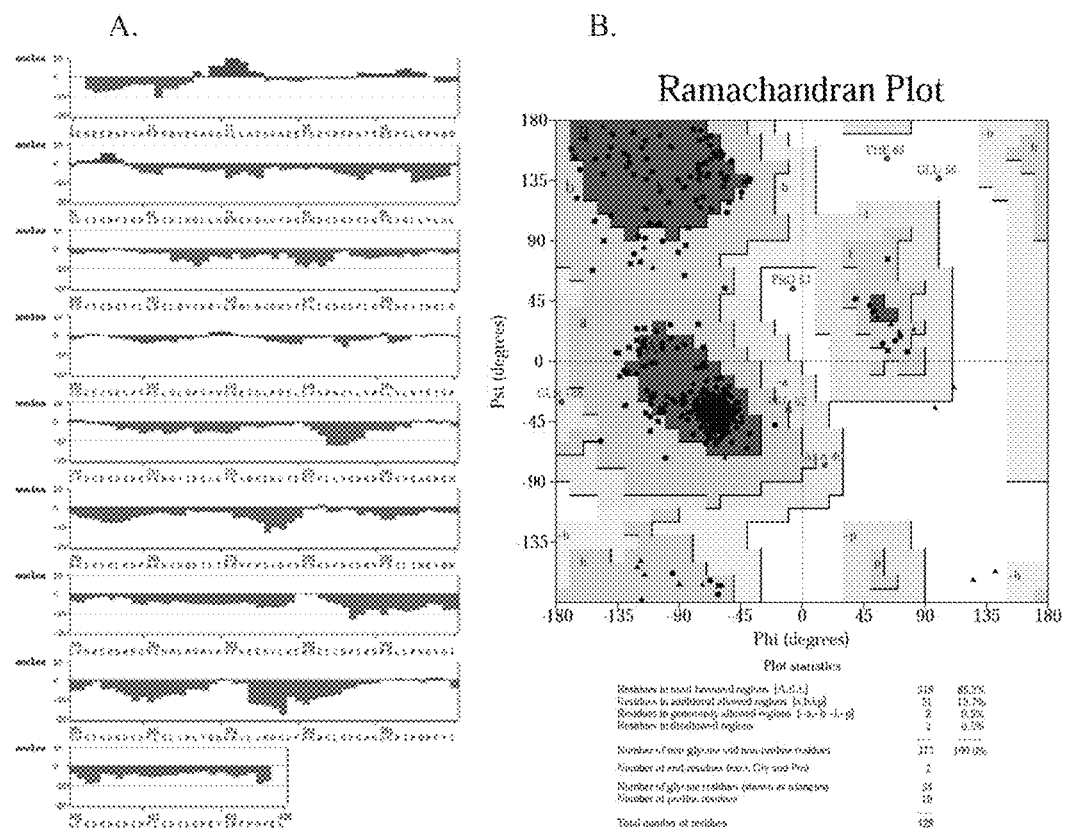
FIG. 6 illustrates the ANOLEA (A) and Ramachandran (B) plots of modeled LANCL2. In the ANOLEA plot, negative values indicate residues in a favorable environment and positive values indicate residues in an unfavorable environment. In the Ramachandran plot, the favored and most favored region is yellow and red respectively; pale yellow is the generously allowed and disallowed regions are white.

Two levels of assessment were performed to determine the quality of the model generated. The atomic empirical mean force potential ANOLEA was used to assess packing quality of the models [19]. ANOLEA performs energy calculations on a protein chain, evaluating the "Non-Local Environment" (NLE) of each heavy atom in the molecule. In the ANOLEA plot, the y-axis of the plot represents the energy for each amino acid of the protein chain. Negative energy values (in green) represent a favorable energy environment whereas positive values (in red), an unfavorable energy environment for a given amino acid. Most amino acid residues in the LANCL2 model appeared in a favorable environment (FIG. 6). The PROCHECK suite of programs assesses the stereochemical quality of a given protein structure [20]. The Ramachandran plot from PROCHECK also indicated the good quality of the model, with 85.3% of $\phi,\psi$ angles in the favored core region, 13.7% in allowed regions, and only 0.5% of residues in generously allowed regions and 0.5% in disallowed regions (FIG. 6).

Figure 7:
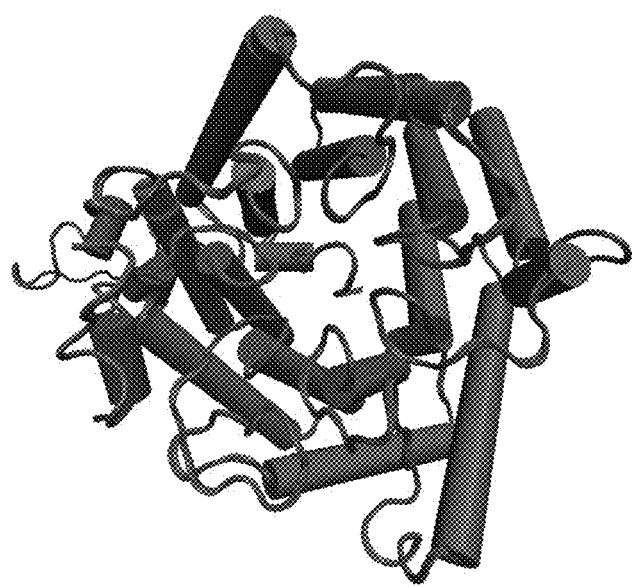
FIG. 7 illustrates a superposition of the LANCL2 model and the LANCL1 template structures. LANCL2 and LANCL1 are colored blue and red, respectively. Helices are depicted by cylinders, random coil by tube.

To improve and verify the stability of the initial structure, an energy minimization procedure was applied to the LANCL2 model [23]. The energy minimization procedure was set to stop when the maximum force reached 1000 KJ/mol/nm. The potential energy in the system decreased in the energy minimization procedure. At the same time, the RMSD of LANCL2 structure relative to the starting structures only increased 0.03 nm. These results show that after the energy minimization procedure, the LANCL2 structure became more stable. Finally, the homology model of LANCL2 improved by the EM procedure and the crystal structure of template (LANCL1) were compared using RAPIDO, a superposition webserver [24]. FIG. 7 shows the LANCL2 model is very similar to the LANCL1 structure, including two layers of α-helical barrels and seven GxxG-containing bulges. The RMSD between the LANCL2 model and LANCL1 structure is 0.47 Angstroms. On the basis of the above analysis, the homology model of LANCL2 improved by the EM procedure was employed for the following docking study.

Molecular Docking and Result Analysis

The AutoDock program is one of the most widely cited docking programs in the research community, owing its efficiency to the use of the Lamarckian genetic algorithm and a grid-based scoring function comprising several terms, including dispersion/repulsion energy, directional hydrogen bonding, screened Coulomb potential electrostatics, a volume-based solvation term, and a weighted sum of torsional degrees of freedom to estimate the entropic cost of binding [33]. Furthermore, it can identify potential binding sites of a ligand on a protein using blind docking, without the information about binding sites. In addition, full consideration of flexibility of ligands during the docking procedure makes AutoDock an appropriate tool for binding site identification. The docking of ABA with LANCL2 was performed in two steps.

Figure 8:
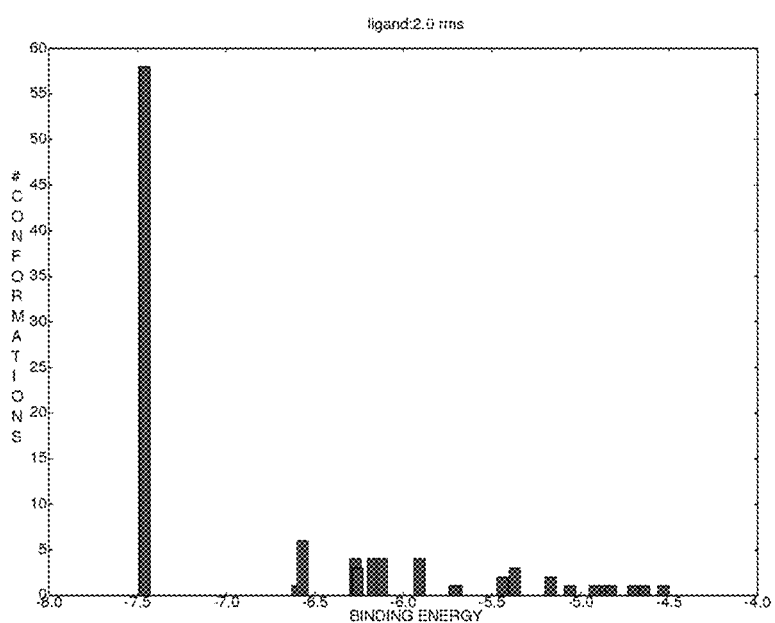
FIG. 8 shows the docked results by clustering histogram. The 100 resulting conformations of ligands were clustered with RMSD cluster tolerance of 2.0 Å. Abscissa represents the lowest binding energy in each cluster.
Figure 9:
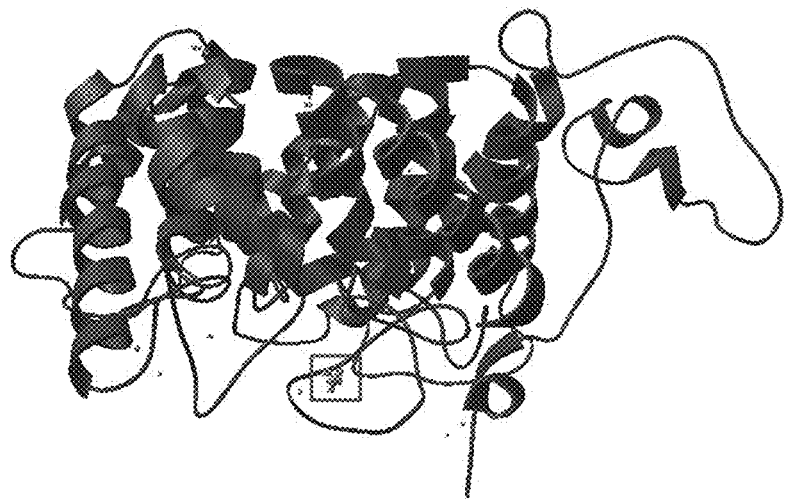
FIG. 9 illustrates the distribution of conformations. Each docked conformation is represented by a green sphere placed at the average position of the coordinates of all the atoms in that conformation. The binding site with the most poses of ABA is outlined by the red box.
Figure 10:
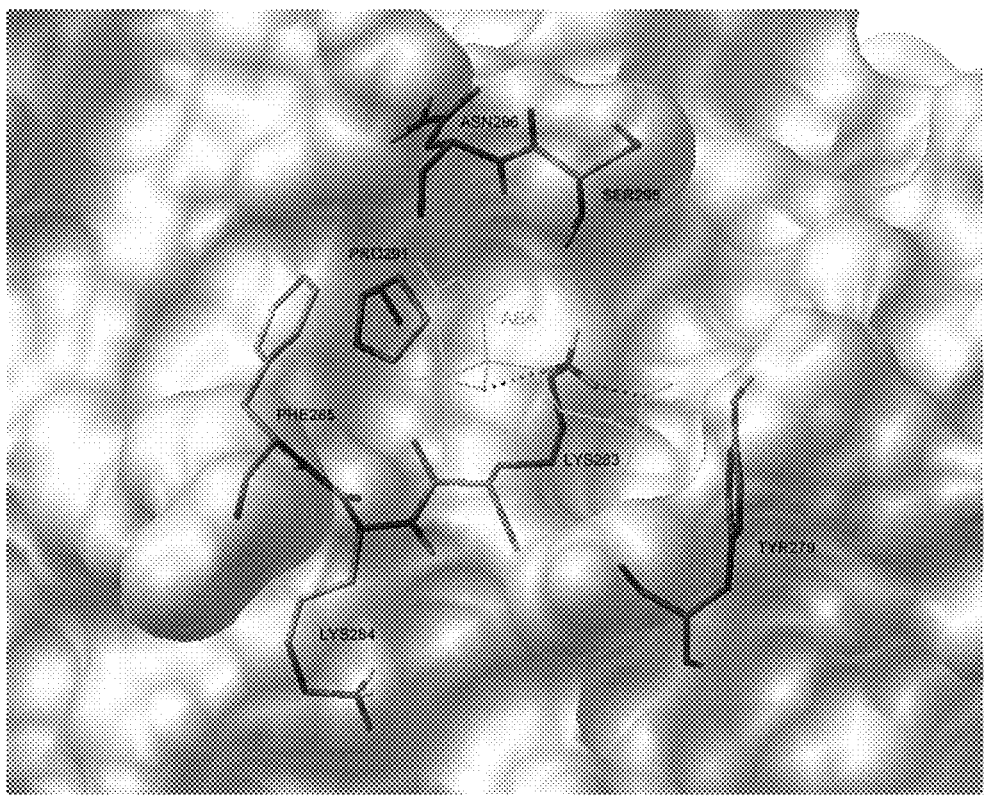
FIG. 10 depicts the binding modes of the most stable docked orientation of ABA with LANCL2. LANCL2 is shown in a molecular surface model. ABA is shown by a cyan stick model, and selected residues of LANCL2 are depicted by gray stick models. Hydrogen bonds are shown as dashed green lines. Amino acid residues surrounding ABA are labeled as single letters.

In the first step, the blind docking approach was used in order to identify the potential binding sites of LANCL2. The grid generated by AutoGrid was big enough to cover the entire surface of LANCL2. The 100 resulting conformations of ligands were clustered with an RMSD cluster tolerance of 2.0 Å. The clustering plot revealed that 58% of the poses of ABA are located in the first cluster with a mean binding energy of −6.70 kcal/mol (FIG. 8). Examination of the distribution of the binding site on the LANCL2 implies that ABA shows preferential binding to the loop regions of LANCL2, which is consistent with our prediction about the substrate-binding site of LANCL2 (FIG. 9). This region on the LANCL2 with the high population of clusters was considered as the potential binding site for ABA. FIG. 10 shows ABA bound inside a pocket in LANCL2. The binding pocket was surrounded by TYR179, LYS284, PHE285, PRO291, ASN296 and SER295. LYS 283 was located in the bottom of the pocket. Two hydrogen bonds formed between the nitrogen atom in the side chain of LYS283 and two hydroxyl groups of ABA that positioned ABA deep in the pocket and increased the affinity of ABA for LANCL2 (FIG. 10).

Figure 11:
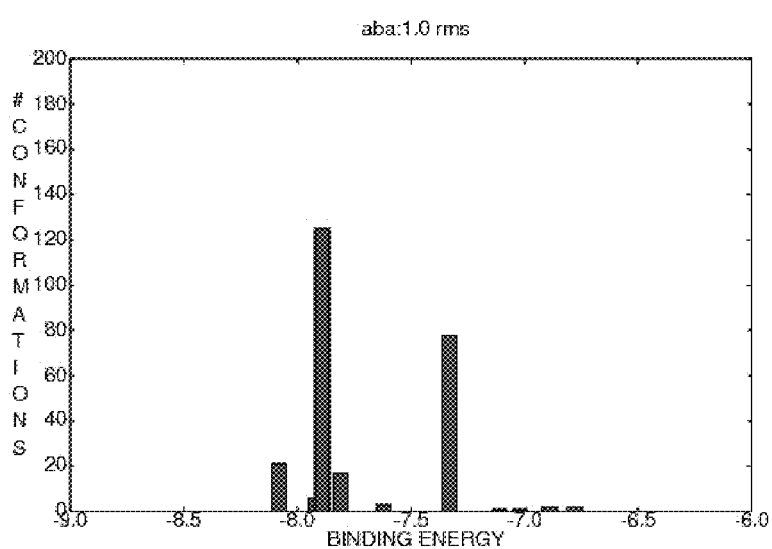
FIG. 11 illustrates a clustering histogram. The 256 resulting conformations of ligands were clustered with RMS cluster tolerance of 1.0 Å. Abscissa represents the lowest binding energy in each cluster.

In the second step (focused docking), ABA was docked into the binding site previously found. The use of an increased grid resolution focusing on the predicted binding site allows more focused searching and better evaluation of the protein-ligand interactions, and consequently lower binding energies are obtained with respect to the blind docking (FIG. 11). Comparisons of docking results were performed between blind docking and focused docking (Table 2).

TABLE 2

Comparison docking results between blind docking and focused docking.

| | Cluster number | Lowest binding energy | Mean binding energy in the first cluster |
|---|---|---|---|
| Blind docking | 20 | −7.46 kcal/mol | −6.70 kcal/mol |
| Focused docking | 10 | −8.08 kcal/mol | −7.92 kcal/mol |

Docking Test of Other PPAR γ Agonists on LANCL2

Figure 12:
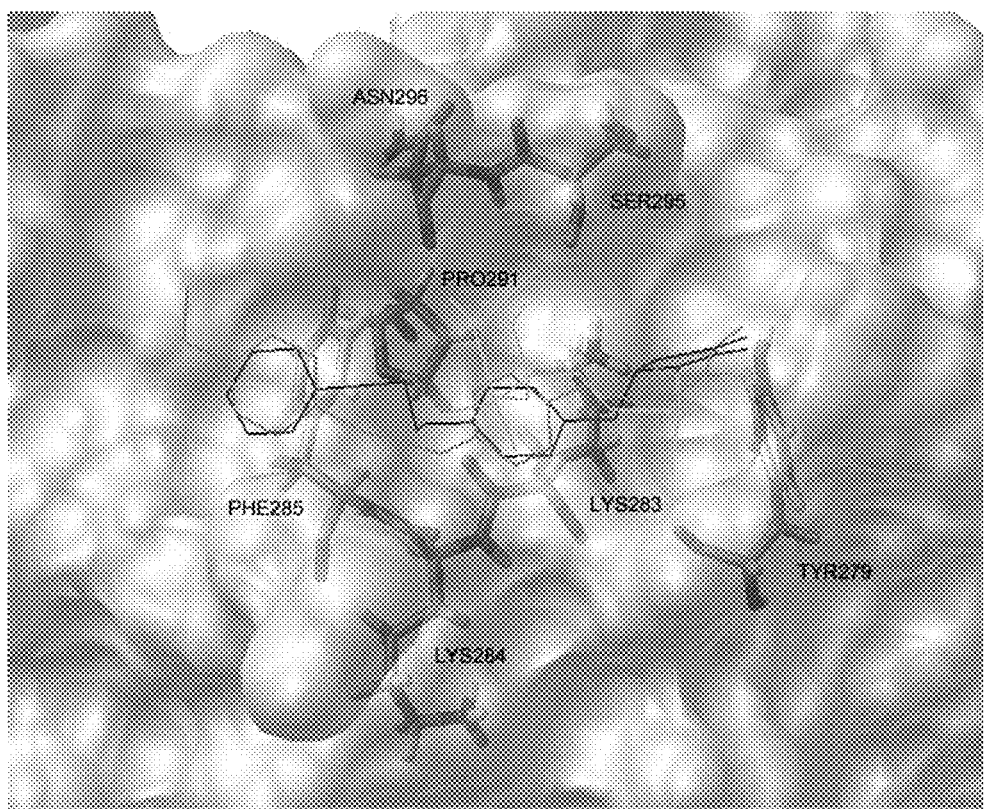
FIG. 12 illustrates the binding modes of ABA and thiazolidinediones (TZD) on LANCL2. ABA is colored in cyan, pioglitazone is colored in green and rosiglitazone is colored in blue. LANCL2 is shown in a molecular surface model. Selected residues of LANCL2 are depicted by stick-and-ball models and colored by atom types (Red: oxygen; Blue: nitrogen; White: hydrogen). This figure illustrates that ABA and TZDs may bind to the same site on LANCL2.

In order to determine whether other PPAR γ agonists may also bind to LANCL2, we docked several small naturally occurring molecules with PPAR agonistic effects, including rumenic acid, punicic acid, catalpic acid, eleostearic acid, calendic acid, jacaric acid, pioglitazone and rosiglitazone, to LANCL2 using the blind docking method. Docking results are displayed in Table 3 according to the lowest binding energy of these chemicals. Compared to the other molecules, pioglitazone and rosiglitazone showed better binding ability to LANCL2 with lower binding energy. These compounds belong to the TZD class of T2D drugs and, in contrast to ABA, are known to bind to the LBD of PPAR γ. Docking results showed that pioglitazone and rosiglitazone could bind to the same binding site as ABA on LANCL2 (FIG. 12). On the basis of this result, we propose that LANCL2 is not only necessary for transduction of the ABA signal into cell-specific functional responses, but it may also be one important membrane receptor for a series of antidiabetic drugs that act by activating PPAR γ. Thus, LANCL2 is upstream of PPAR γ signaling.

TABLE 3

Docking results of small molecules to LANCL2, ranked by the lowest binding energy.

| Common Name | Chemical Name | Chemical Structure | Lowest Binding Energy (kcal/mol) |
|---|---|---|---|
| abscisic acid | [S-(Z,E)]-5-(1-Hydroxy-2,6,6-trimethyl-4-oxo-2-cyclohexen-1-yl)-3-methyl-2,4-pentanedienoic acid | 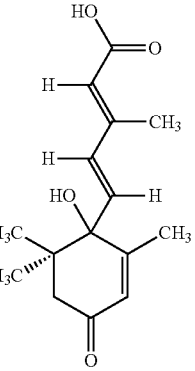 | −7.46 |

TABLE 3-continued

Docking results of small molecules to LANCL2, ranked by the lowest binding energy.

| Common Name | Chemical Name | Chemical Structure | Lowest Binding Energy (kcal/mol) |
|---|---|---|---|
| rosiglitazone | (RS)-5-[4-(2-[methyl(pyridin-2-yl)amino]ethoxy)benzyl]-thiazolidine-2,4-dione | 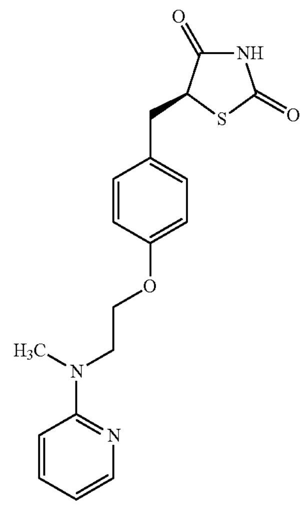 [SMILES: CN(CCOc1ccc(C[C@@H]2SC(=O)NC2=O)cc1)c1ccccn1] | −7.95 |
| pioglitazone | (RS)-5-(4-[2-(5-ethyl-pyridin-2-yl)ethoxy]-benzyl)thiazolidine-2,4-dione | 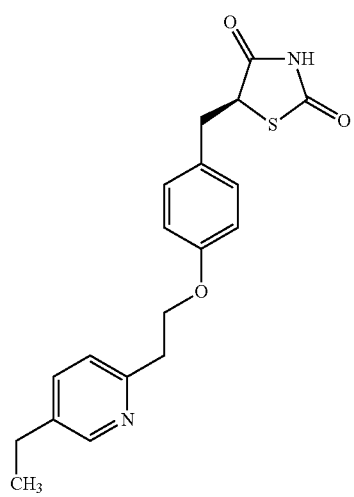 [SMILES: CCc1ccc(CCOc2ccc(C[C@@H]3SC(=O)NC3=O)cc2)nc1] | −7.08 |
| α-Calendic acid | (8E,10E,12Z)-octadeca-8,10,12-trienoic acid | 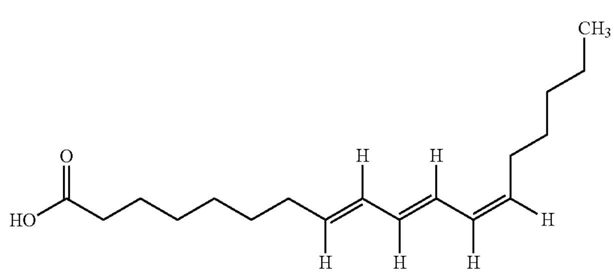 [SMILES: CCCCC\C=C/C=C/C=C/CCCCCCC(=O)O] | −5.79 |

TABLE 3-continued

Docking results of small molecules to LANCL2, ranked by the lowest binding energy.

| Common Name | Chemical Name | Chemical Structure | Lowest Binding Energy (kcal/mol) |
|---|---|---|---|
| catalpic acid | (9Z,11Z,13E)-octadeca-9,11,13-trienoic acid | 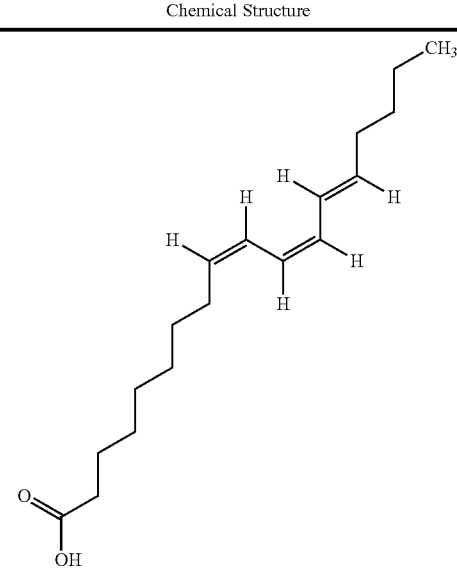 | −5.72 |
| β-Calendic acid | (8E,10E,12E)-octadeca-8,10,12-trienoic acid | 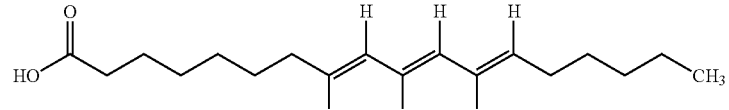 | −5.65 |
| t10, c12 conjugated linoleic acid | (10E,12Z)-octadeca-9,11-dienoic acid | 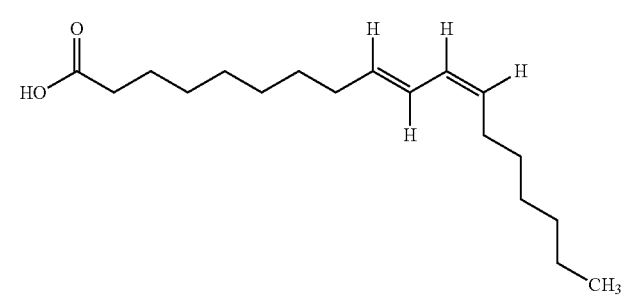 [SMILES: CCCCCC/C=C\C=C\CCCCCCCC(=O)O] | −5.40 |
| β-eleostearic acid | (9E,11E,13E)-octadeca-9,11,13-trienoic acid | 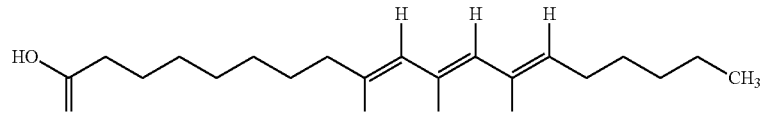 | −5.28 |
| α-eleostearic acid | (9Z,11E,13E)-octadeca-9,11,13-trienoic acid | 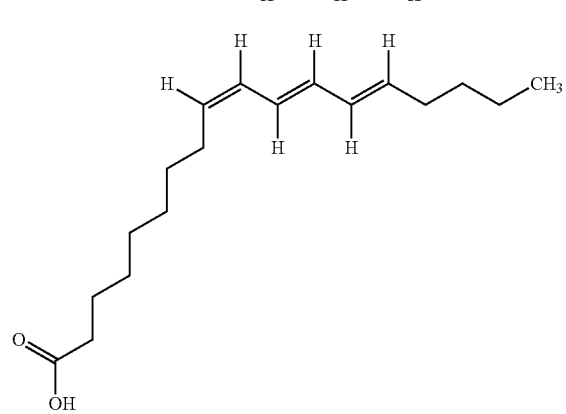 | −5.21 |

TABLE 3-continued

Docking results of small molecules to LANCL2, ranked by the lowest binding energy.

| Common Name | Chemical Name | Chemical Structure | Lowest Binding Energy (kcal/mol) |
|---|---|---|---|
| punicic acid | (9Z,11E,13Z)-octadeca-9,11,13-trienoic acid | 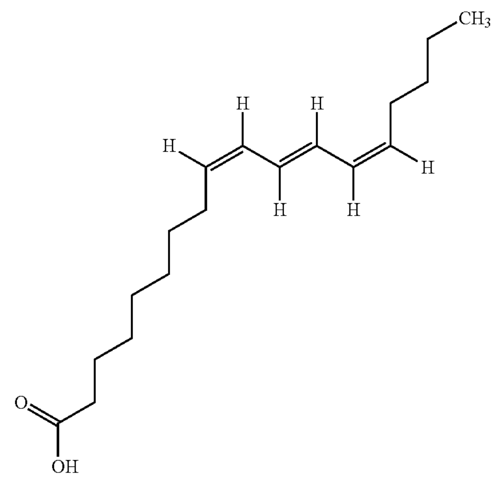 [SMILES: CCCC\C=C/C=C/C=C\CCCCCCCC(=O)O] | −5.18 |
| jacaric acid | (8E,10Z,12E)-octadeca-8,10,12-trienoic acid | 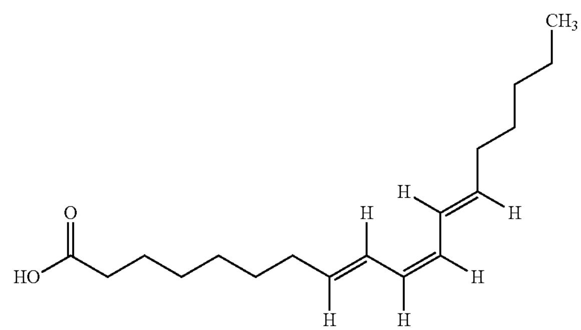 [SMILES: CCCCC/C=C/C=C\C=C\CCCCCCC(=O)O] | −5.09 |
| c9, t11 conjugated linoleic acid | (9Z,11E)-octadeca-9,11-dienoic acid | 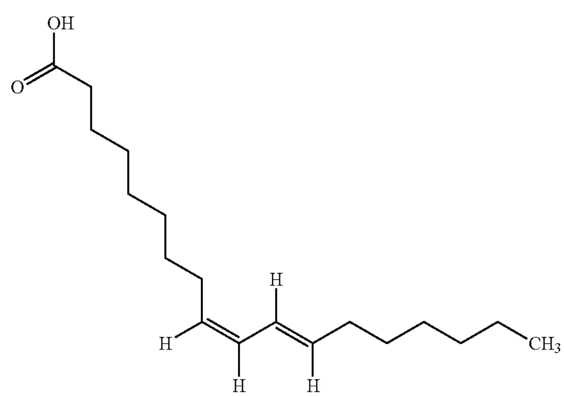 [SMILES: CCCCCC/C=C/C=C\CCCCCCCC(=O)O] | −4.98 |

Virtual Screening and Results Analysis

To discover novel naturally occurring compounds, new drugs and repurposed drugs that target the LANCL2/PPAR pathway and exert insulin-sensitizing and anti-inflammatory actions, virtual screening was applied to identify potential ligands of LANCL2. The compound databases used for screening contain NCI Diversity Set II, ChemBridge and ZINC natural product, existing drug databases, FDA-approved drugs databases, for designing repurposed drugs as well as ABA analogs.

Figure 13:
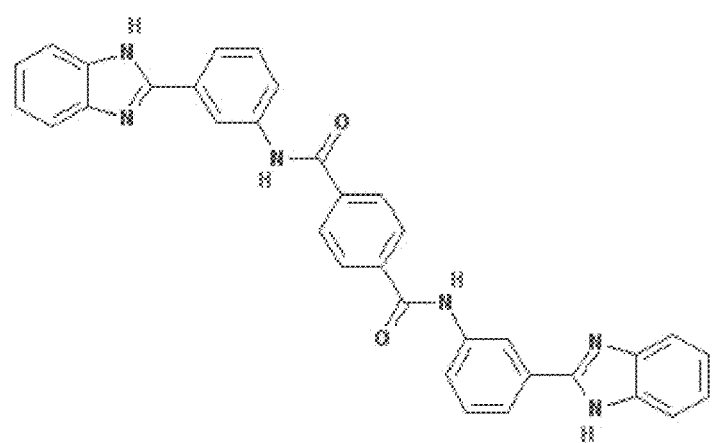
FIG. 13 shows chemical structure of 1-N,4-N-bis[3-(1H-benzimidazol-2-yl)phenyl]benzene-1,4-dicarboxamide (NSC61610), a new ligand of LANCL2 discovered by our group.
Figure 14:
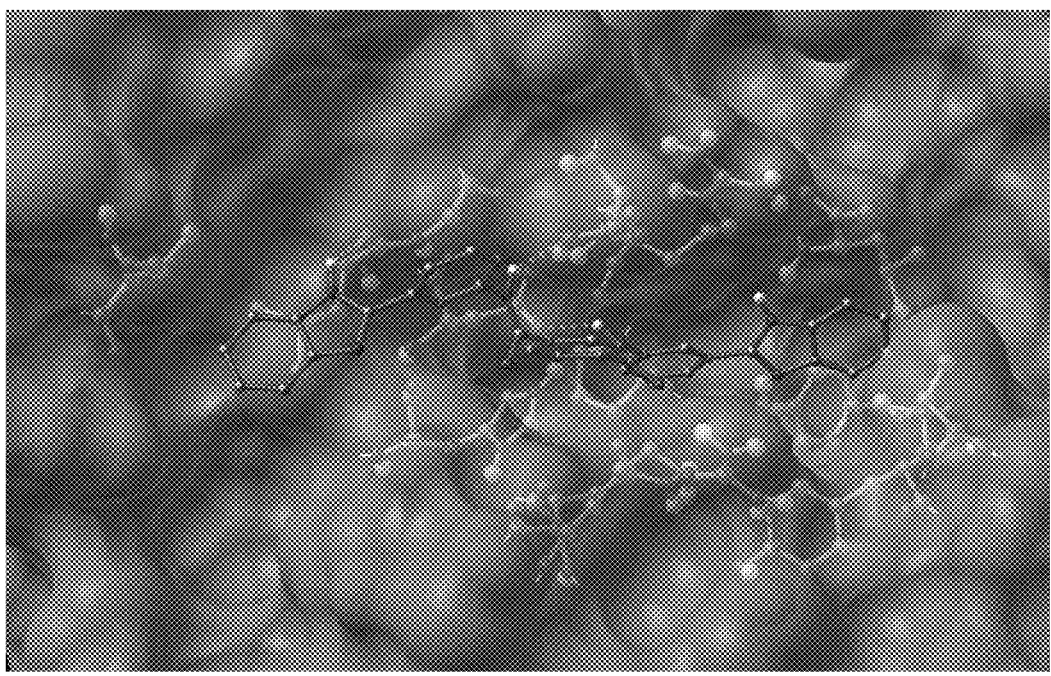
FIG. 14 illustrates the binding modes of the most stable docked orientation of NSC61610 with LANCL2. The LANCL2 model is shown in a molecular surface model. Selected residues of LANCL2 (cyan) and NSC61610 (magenta) are depicted by stick-and-ball models and colored by atom types (Red: oxygen; Blue: nitrogen; White: hydrogen). Hydrogen bonds are shown as dashed green lines.

The compounds resulting conformations of ligands were ranked according to their estimated free energy of binding. The best ten docking solutions based on the energy scores were selected for each database (Table 4-8). The lower binding free energy indicates more stable protein-ligand bound system and higher affinity between protein and ligand. Lead compounds in each category will be further validated by in vitro testing and pre-clinical studies using mouse models of diabetes, inflammation or infectious diseases. NSC61610 had the lowest free energy of binding −11.1 kcal/mol compared to other compounds in NCI Diversity Set II (FIG. 13). Thus, the region on the LANCL2 with the lowest free energy binding mode was considered as the potential binding site for NSC61610 (FIG. 14). The effect of NSC61610 has been tested by a series of pre-clinical efficacy studies using a mouse model of DSS-induced colitis, a mouse model of influenza and in vitro experiments.

TABLE 4

Docking results of compounds in NCI Diversity Set II to LANCL2, ranked by the lowest binding energy.

| ZINC Number | Name | Chemical Structure | Lowest Binding Energy (kcal/mol) |
|---|---|---|---|
| ZINC01690699 (NSC61610) | 1-N,4-N-bis[3-(1H-benzimidazol-2-yl)phenyl]benzene-1,4-dicarboxamide | 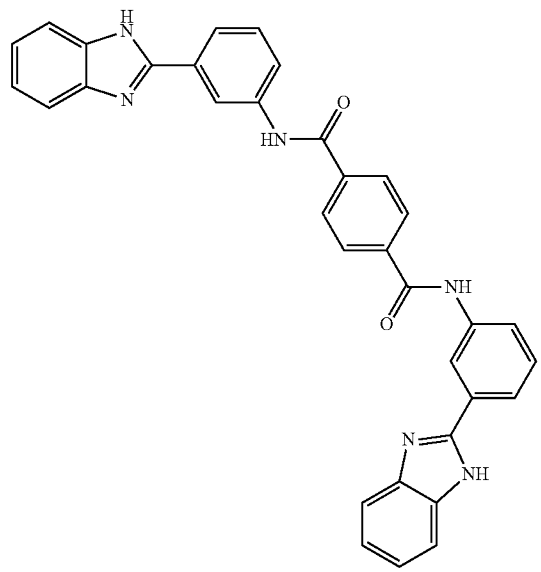 [SMILES: O=C(Nc1cccc(-c2nc3ccccc3[nH]2)c1)c1ccc(C(=O)Nc2cccc(-c3nc4ccccc4[nH]3)c2)cc1] | −11.1 |
| ZINC29589888 | 2-[2-[(6-oxo-5H-phenanthridin-3-yl)carbamoyl]phenyl]benzoic acid | 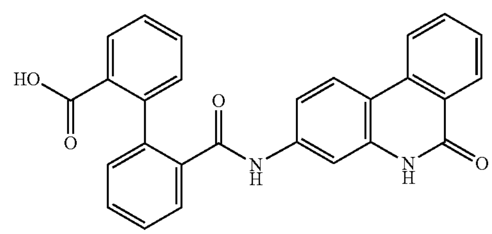 [SMILES: O=C(O)c1ccccc1-c1ccccc1C(=O)Nc1ccc2c(c1)[nH]c(=O)c1ccccc12] | −10.5 |
| ZINC13130018 | 6-(1,3-dihydrophananthro[9,10-d]imidazol-2-ylidene)cyclohexa-2,4-dien-1-one | 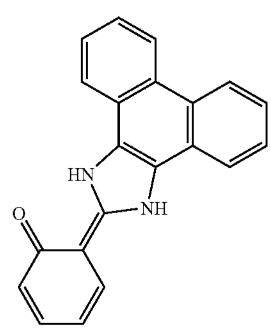 [SMILES: O=C1C=CC=CC1=C1Nc2c(c3ccccc3c3ccccc23)N1] | −10.3 |

TABLE 4-continued

Docking results of compounds in NCI Diversity Set II to LANCL2, ranked by the lowest binding energy.

| ZINC Number | Name | Chemical Structure | Lowest Binding Energy (kcal/mol) |
|---|---|---|---|
| ZINC01726776 | 3-(4-chloro-6-phenoxy-1,3,5-triazin-2-yl)-1-phenylindole | 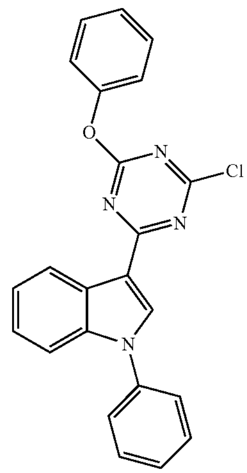 [SMILES: Clc1nc(Oc2ccccc2)nc(-c2cn(-c3ccccc3)c3ccccc23)n1] | −10.2 |
| ZINC01736228 | (2R)-5-phenyl-2-[(2R)-5-phenyl-2,3-dihydro-1,3-benzoxazol-2-yl]-2,3-dihydro-1,3-benzoxazole | 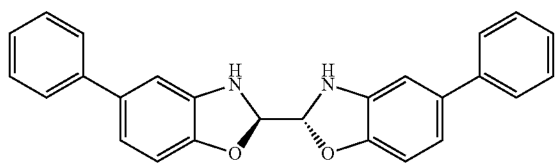 [SMILES: c1ccc(-c2ccc3c(c2)N[C@@H]([C@@H]2Nc4cc(-c5ccccc5)ccc4O2)O3)cc1] | −10.2 |
| ZINC04783229 | 1-N,4-N-bis(3-phenylphenyl)piperazine-1,4-dicarboxamide | 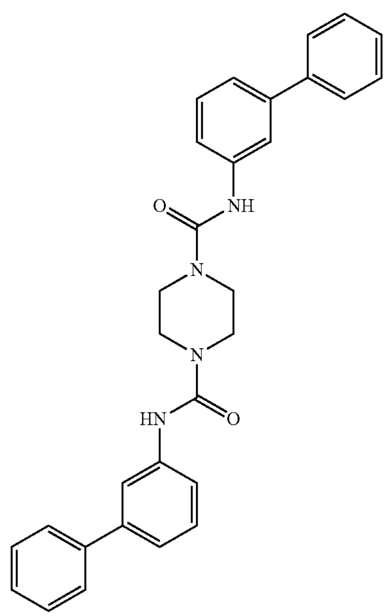 [SMILES: O=C(Nc1cccc(-c2ccccc2)c1)N1CCN(C(=O)Nc2cccc(-c3ccccc3)c2)CC1] | −10.1 |
| ZINC00990239 | 3-(4,5-dimethylbenzo[h][1,6]naphthyridin-1-ium-2-yl)-2-methylquinolin-4-amine | 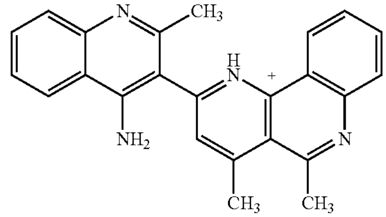 | −10 |

TABLE 4-continued
Docking results of compounds in NCI Diversity Set II to LANCL2, ranked by the lowest binding energy.
| ZINC Number | Name | Chemical Structure | Lowest Binding Energy (kcal/mol) |
|---|---|---|---|
| ZINC18057104 | 4-[(1-methyl-6-nitroquinolin-1-ium-4-yl)amino]-N-[4-[(1-methylpyridin-1-ium-4-yl)amino]phenyl]benzamide | 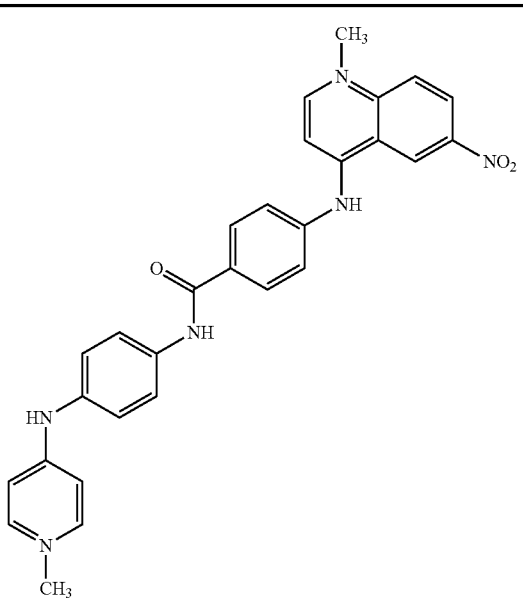 | −10 |
| ZINC04214344 | Genostrychnine | 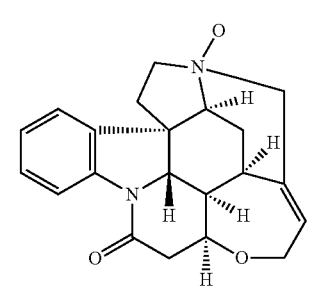 | −9.7 |
| ZINC04720972 | 2-hydroxy-N-(4-methoxyphenyl)-11H-benzo[a]carbazole-3-carboxamide | 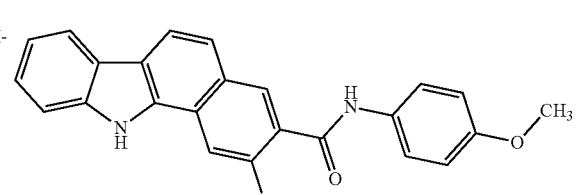 | −9.6 |

TABLE 5

Docking results of compounds in ChemBridge to LANCL2, ranked by the lowest binding energy.

| ZINC Number | Name | Chemical Structure | Lowest Binding Energy (kcal/mol) |
|---|---|---|---|
| ZINC22146248 | 3-[4-(5,5-dioxidodibenzo[b,d]thien-2-yl)-5-phenyl-1H-imidazol-2-yl]-3a,7a-dihydro-1H-indole | 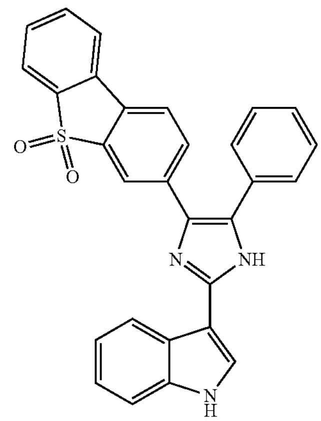 [SMILES: O=S1(=O)c2ccccc2-c2ccc(-c3nc(-c4c[nH]c5ccccc45)[nH]c3-c3ccccc3)cc21] | −10.9 |
| ZINC02848490 | N-(6-chloro-1,3-dioxo-1H-benzo[de]isoquinolin-2(3H)-yl)-9-hydroxy-9H-fluorene-9-carboxamide | 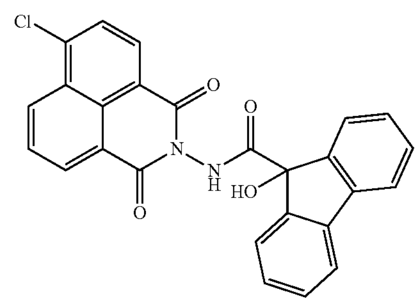 [SMILES: O=C1c2cccc3c(Cl)ccc(c23)C(=O)N1NC(=O)C1(O)c2ccccc2-c2ccccc21] | −10.8 |
| ZINC13081141 | 2-[2-(4-hydroxyphenyl)-5-phenyl-1H-imidazol-4-yl]-7-nitro-9H-fluoren-9-one | 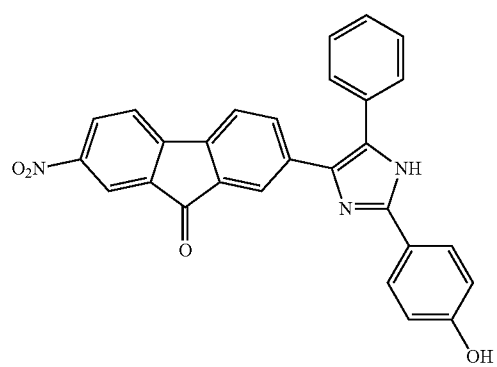 [SMILES: O=C1c2cc(-c3nc(-c4ccc(O)cc4)[nH]c3-c3ccccc3)ccc2-c2ccc([N+](=O)[O-])cc21] | −10.8 |
| ZINC05799242 | 2-(1,3-benzodioxol-5-yl)-4,4-dimethyl-6-phenyl-1,4,5,6-tetrahydroimidazo[4,5-e]indazole | 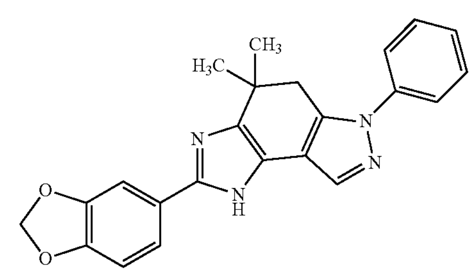 [SMILES: CC1(C)Cc2c(cnn2-c2ccccc2)-c2[nH]c(-c3ccc4c(c3)OCO4)nc21] | −10.5 |

TABLE 5-continued

Docking results of compounds in ChemBridge to LANCL2, ranked by the lowest binding energy.

| ZINC Number | Name | Chemical Structure | Lowest Binding Energy (kcal/mol) |
|---|---|---|---|
| ZINC04602469 | 2-[4-amino-6-(dimethylamino)-1,3,5-triazin-2-yl]-3-dibenzo[b,d]furan-2-ylacrylonitrile | 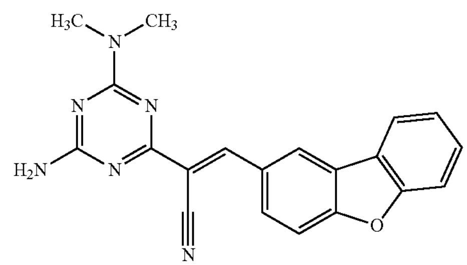 [SMILES: CN(C)c1nc(N)nc(/C(C#N)=C/c2ccc3oc4ccccc4c3c2)n1] | −10.3 |
| ZINC02909739 | 1-phenyl-5-{[(5-phenyl-1,3,4-thiadiazol-2-yl)amino]methylene}-2,4,6(1H,3H,5H)-pyrimidinetrione | 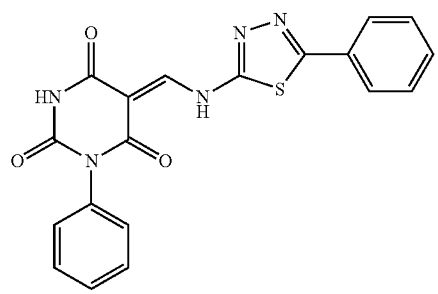 [SMILES: O=C1NC(=O)N(c2ccccc2)C(=O)/C1=C\Nc1nnc(-c2ccccc2)s1] | −10.2 |
| ZINC14740873 | 7-[(6-chloro-2H-chromen-3-yl)methyl]-3-(3,4-dihydro-2H-chromen-3-yl)-1-methyl-5,6,7,8-tetrahydroimidazo[1,5-a]pyrazine | 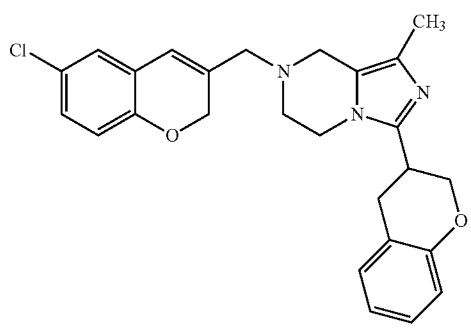 [SMILES: Cc1nc(C2COc3ccccc3C2)n2c1CN(CC1=Cc3cc(Cl)ccc3OC1)CC2] | −10.2 |
| ZINC05338533 | 1-phenyl-4,11-dihydroimidazo[4,5-e]naphtho[2,3-b][1,4]diazepin-2(1H)-one | 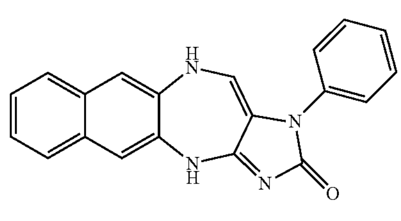 [SMILES: O=C1N=C2Nc3cc4ccccc4cc3NC=C2N1c1ccccc1] | −10.2 |
| ZINC08387449 | 1-phenyl-4,11-dihydroimidazo[4,5-e]naphtho[2,3-b][1,4]diazepin-2(1H)-one | 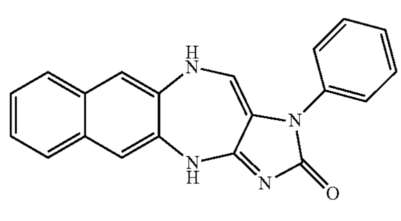 [SMILES: O=C1N=C2Nc3cc4ccccc4cc3NC=C2N1c1ccccc1] | −10.2 |

TABLE 5-continued

Docking results of compounds in ChemBridge to LANCL2, ranked by the lowest binding energy.

| ZINC Number | Name | Chemical Structure | Lowest Binding Energy (kcal/mol) |
|---|---|---|---|
| ZINC05564677 | ethyl 4-[5-(4-fluorophenyl)-2-furyl]-2-oxo-6-phenyl-1,2-dihydro-5-pyrimidinecarboxylate | 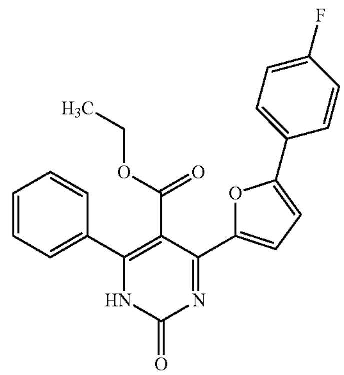 [SMILES: CCOC(=O)c1c(-c2ccc(-c3ccc(F)cc3)o2)nc(=O)[nH]c1-c1ccccc1] | −10.1 |

TABLE 6

Docking results of compounds in ZINC Natural Products database to LANCL2, ranked by the lowest binding energy.

| ZINC Number | Name | Chemical Structure | Lowest Binding Energy (kcal/mol) |
|---|---|---|---|
| ZINC03845566 | 3,7-bis(2-oxo-1H-indole-3-ylidene)-1,5-dihydropyrrolo[2,3-f]indole-2,6-dione | 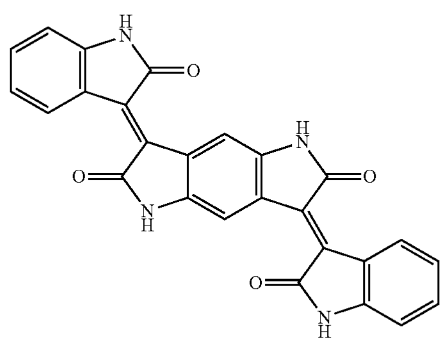 [SMILES: O=C1Nc2ccccc2/C1=C1\C(=O)Nc2cc3c(cc21)NC(=O)/C3=C1/C(=O)Nc2ccccc21] | −12.8 |
| ZINC03848528 | 1-amino-3-[(4-amino-9,10-dioxoanthracen-2-yl)amino]anthracene-9,10-dione | 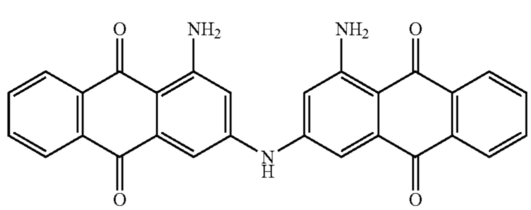 [SMILES: Nc1cc(Nc2cc(N)c3c(c2)C(=O)c2ccccc2C3=O)cc2c1C(=O)c1ccccc1C2=O] | −12.0 |

TABLE 6-continued

Docking results of compounds in ZINC Natural Products database to LANCL2, ranked by the lowest binding energy.

| ZINC Number | Name | Chemical Structure | Lowest Binding Energy (kcal/mol) |
|---|---|---|---|
| ZINC05220992 | benzo[lmn]diquinazolino[2,1-b:2',3'-i][3,8]phenanthroline-5,9,11,19-tetrone | 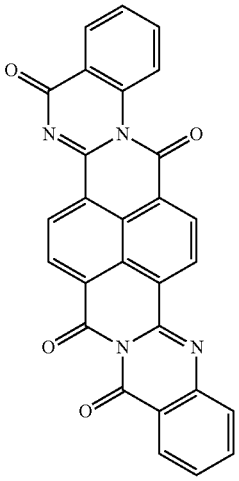 [SMILES: O=c1nc2c3ccc4c(=O)n5c(=O)c6ccccc6nc5c5ccc(c(=O)n2c2ccccc12)c3c45] | −11.7 |
| ZINC08792261 | N-1,3-benzothiazol-2-yl-2-[(9-oxo-9H-benzo[c]indolo[3,2,1-ij][1,5]naphthyridin-5-yl)oxy]propanamide | 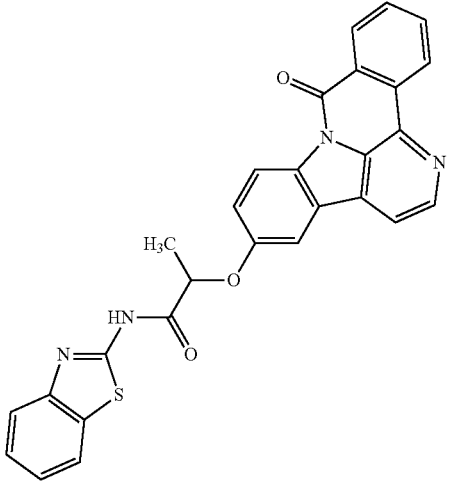 [SMILES: CC(Oc1ccc2c(c1)c1ccnc3c4ccccc4c(=O)n2c13)C(=O)Nc1nc2ccccc2s1] | −11.5 |
| ZINC09033168 | 1-(2-dibenzofuran-3-ylhydrazinyl)-[1]benzofuro[3,2-e]indol-2-one | 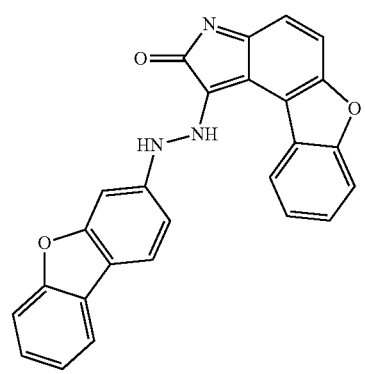 [SMILES: O=C1N=c2ccc3oc4ccccc4c3c2=C1NNc1ccc2c(c1)oc1ccccc12] | −11.4 |

TABLE 6-continued

Docking results of compounds in ZINC Natural Products database to LANCL2, ranked by the lowest binding energy.

| ZINC Number | Name | Chemical Structure | Lowest Binding Energy (kcal/mol) |
|---|---|---|---|
| ZINC02121309 | 2-(2-dibenzofuran-2-ylhydrazinyl)-[1]benzofuro[3,2-f]indol-1-one | 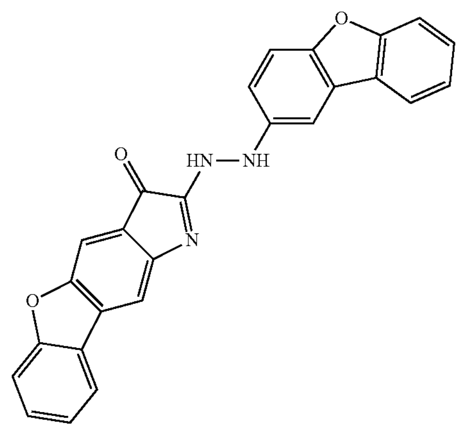 [SMILES: O=C1C(NNc2ccc3oc4ccccc4c3c2)=Nc2cc3c(cc21)oc1ccccc13] | −10.8 |
| ZINC12654409 | 3',11'-Dihydroxy-3H-spiro[2-benzofuran-1,7'-dibenzo[c,h]xanthen]-3-one | 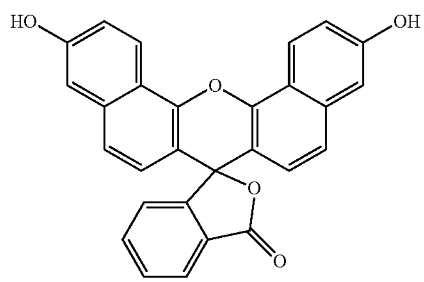 [SMILES: O=C1OC2(c3ccccc31)c1ccc3cc(O)ccc3c1Oc1c2ccc2cc(O)ccc12] | −10.7 |
| ZINC03843486 | [1,4]benzodioxino[2,3-b][1,4]benzodioxino[2',3':5,6]pyrazino[2,3-g]quinoxazline | 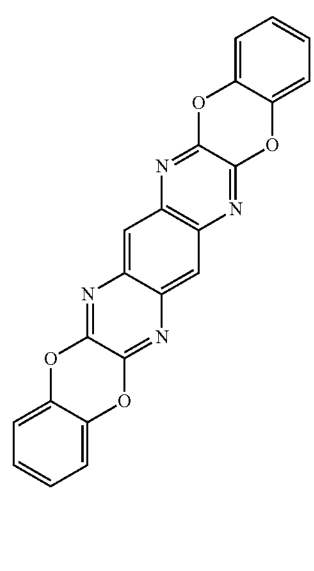 [SMILES: c1ccc2oc3nc4cc5nc6oc7ccccc7oc6nc5cc4nc3oc2c1] | −10.6 |

TABLE 6-continued

Docking results of compounds in ZINC Natural Products database to LANCL2, ranked by the lowest binding energy.

| ZINC Number | Name | Chemical Structure | Lowest Binding Energy (kcal/mol) |
|---|---|---|---|
| ZINC04701574 | 6-chloro-3-[(2E)-2-[1-(2-oxochromen-3-yl)ethylidene]hydrazinyl]indol-2-one | 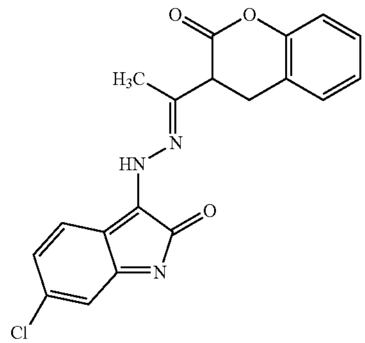 [SMILES: C/C(=N\NC1=c2ccc(Cl)cc2=NC1=O)C1Cc2ccccc2OC1=O] | −10.6 |
| ZINC04266071 | (2Z)-2-(3-oxo-1H-indol-2-ylidene)naphtho[3,2-e][1]benzothiole-1,6,11-trione | 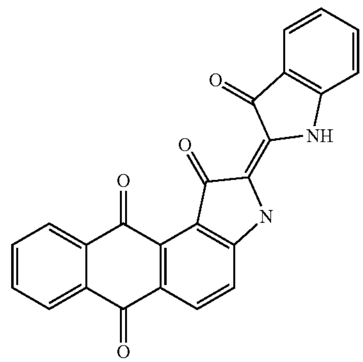 [SMILES: O=C1/C(=C2/Nc3ccc4c(c3C2=O)C(=O)c2ccccc2C4=O)Nc2ccccc21] | −10.4 |

TABLE 7

Docking results of compounds in FDA-approved drugs database to LANCL2, ranked by the lowest binding energy.

| ZINC Number | Name | Chemical Structure | Function | Lowest Binding Energy (kcal/mol) |
|---|---|---|---|---|
| ZINC 03830554 | 4-amino-3-[[4-[4-[(1-amino-4-sulfonatonaphthalen-2-yl)diazenyl]phenyl]phenyl]diazenyl]naphthalene-1-sulfonate | 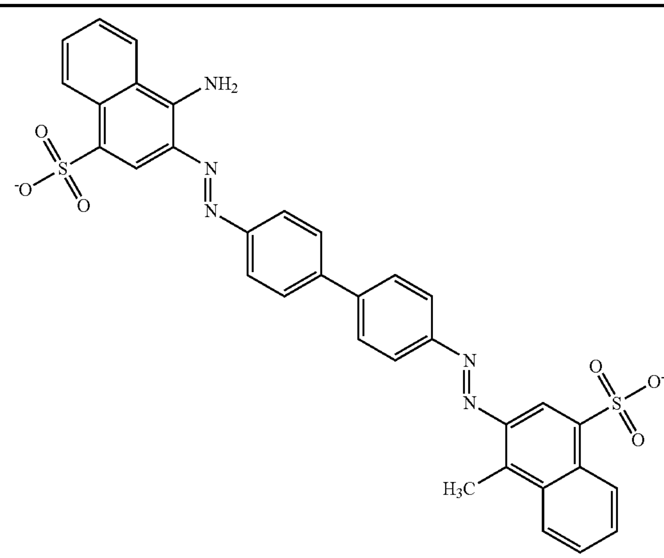 | inhibit amyloid polymerization | −10.5 |

TABLE 7-continued

Docking results of compounds in FDA-approved drugs database to LANCL2, ranked by the lowest binding energy.

| ZINC Number | Name | Chemical Structure | Function | Lowest Binding Energy (kcal/mol) |
|---|---|---|---|---|
| ZINC 11678081 | Carminomycin | 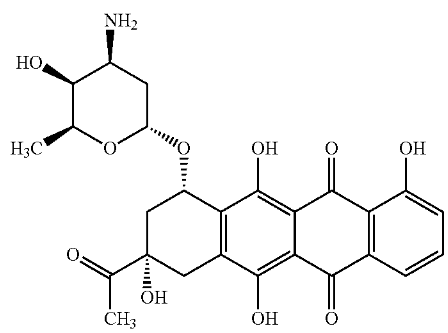 [SMILES: CC(=O)[C@]1(O)Cc2c(O)c3c(c(O)c2[C@@H](O[C@H]2C[C@H](N)[C@H](O)[C@H](C)O2)C1)C(=O)c1c(O)cccc1C3=O] | antibiotics, antineoplastic | −9.9 |
| ZINC 08552616 | Algestone Acetophenide | 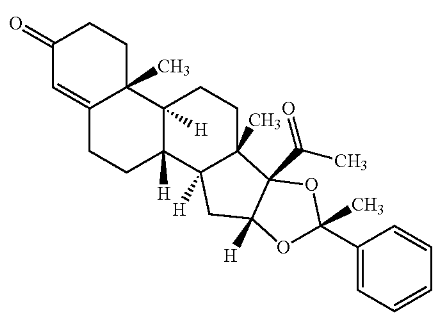 | progestins, contraceptives, anti-inflammatory agents | −9.7 |
| ZINC 08101049 | Acetyldigitoxins | 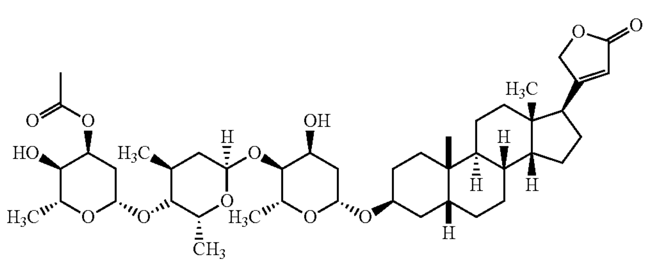 | anti-arrythmia, cardiotonic agents | −9.5 |

TABLE 7-continued

Docking results of compounds in FDA-approved drugs database to LANCL2, ranked by the lowest binding energy.

| ZINC Number | Name | Chemical Structure | Function | Lowest Binding Energy (kcal/mol) |
|---|---|---|---|---|
| ZINC 08101053 | Aclacur | 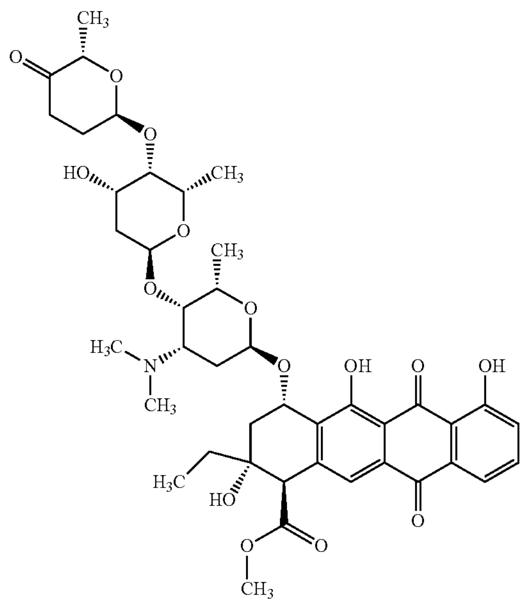 [SMILES: CC[C@@]1(O)C[C@H](O[C@H]2C[C@H](N(C)C)[C@H](O[C@H]3C[C@H](O)[C@H](O[C@H]4CCC(=O)[C@H](C)O4)[C@H](C)O3)[C@H](C)O2)c2c(cc3c(c2O)C(=O)c2c(O)cccc2C3=O)[C@H]1C(=O)OC] | antibiotics, antineoplastic | −9.4 |
| ZINC 08101078 | Digitoxin | 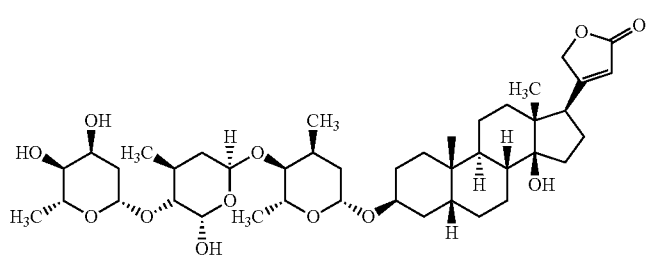 | anti-arrythmia, cardiotonic agents | −9.4 |
| ZINC 01529463 | Estrone hydrogen sulfate | 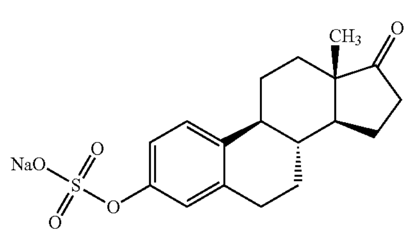 | female hormone | −9.4 |

TABLE 7-continued

Docking results of compounds in FDA-approved drugs database to LANCL2, ranked by the lowest binding energy.

| ZINC Number | Name | Chemical Structure | Function | Lowest Binding Energy (kcal/mol) |
|---|---|---|---|---|
| ZINC 03830332 | 4,4'-((2,4-Dihydroxy-5-(hydroxymethyl)-1,3-phenylene)bis(azo))bis-naphthalene-1-sulphonic acid | 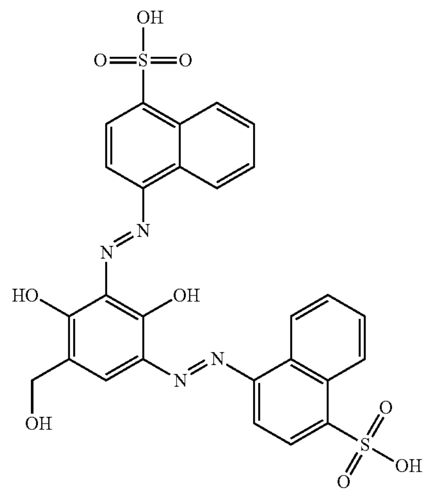 [SMILES: O=S(=O)(O)c1ccc(/N=N/c2cc(CO)c(O)c(/N=N/c3ccc(S(=O)(=O)O)c4ccccc34)c2O)c2ccccc12] | | −9.4 |
| ZINC 11592963 | Idarubicin | 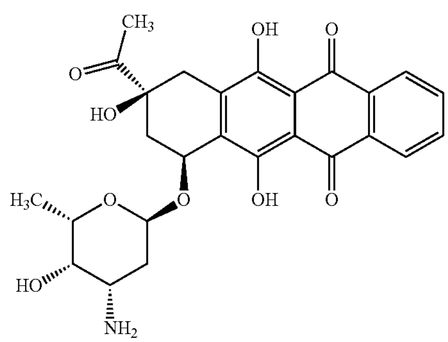 [SMILES: CC(=O)[C@]1(O)Cc2c(O)c3c(c(O)c2[C@@H](O[C@H]2C[C@H](N)[C@H](O)[C@H](C)O2)C1)C(=O)c1ccccc1C3=O] | antibiotics, antineoplastic | −9.4 |
| ZINC 03830975 | Itraconazole | 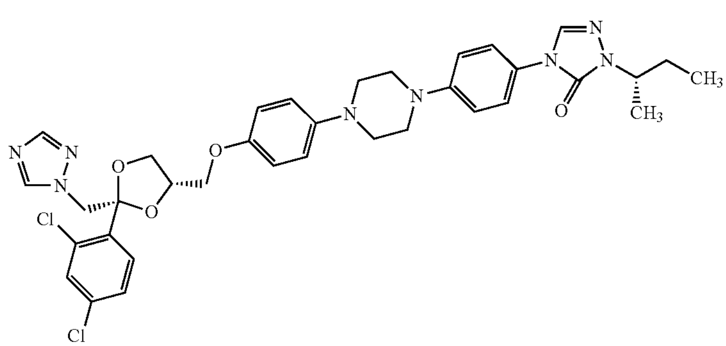 [SMILES: CC[C@H](C)n1ncn(-c2ccc(N3CCN(c4ccc(OC[C@H]5CO[C@](Cn6cncn6)(c6ccc(Cl)cc6Cl)O5)cc4)CC3)cc2)c1=O] | antifungal agents | −9.3 |

TABLE 8

Docking results of ABA analogs to LANCL2, ranked by the lowest binding energy.

| CID | Name | Chemical Structure | Lowest Binding Energy (kcal/mol) |
|---|---|---|---|
| 5771635 | (2E,4Z)-5-[(1R)-1-hydroxy-2,6,6-trimethyl-4-oxocyclohex-2-en-1-yl]-3-methylpenta-2,4-dienoic acid | 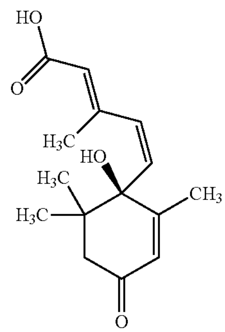 [SMILES: CC1=CC(=O)CC(C)(C)[C@]1(O)/C=C\C(C)=C\C(=O)O] | −7.6 |
| 10313782 | (2Z,4E)-5-[(1R,6S)-1-hydroxy-2,6-dimethyl-4-oxo-6-(trifluoromethyl)cyclohex-2-en-1-yl]-3-methylpenta-2,4-dienoic acid | 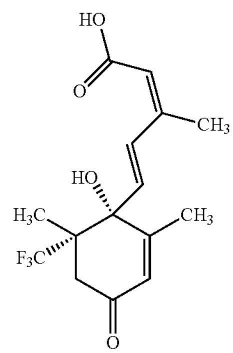 [SMILES: CC1=CC(=O)C[C@](C)(C(F)(F)F)[C@@]1(O)/C=C/C(C)=C\C(=O)O] | −7.3 |
| 44326919 | (2Z,4E)-5-[1-hydroxy-2,6-dimethyl-4-oxo-6-(trifluoromethyl)cyclohex-2-en-1-yl]-3-methylpenta-2,4-dienoic acid | 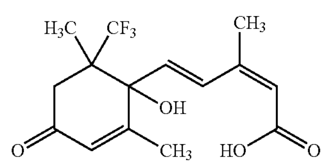 [SMILES: CC1=CC(=O)CC(C)(C(F)(F)F)C1(O)/C=C/C(C)=C\C(=O)O] | −7.2 |
| 10612878 | (2Z,4E)-5-[(1R,6R)-6-(fluoromethyl)-1-hydroxy-2,6-dimethyl-4-oxocyclohex-2-en-1-yl]-3-methylpenta-2,4-dienoic acid | 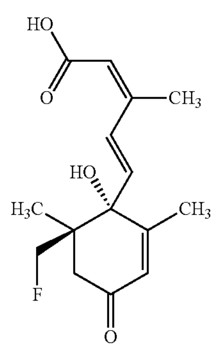 [SMILES: CC1=CC(=O)C[C@@](C)(CF)[C@@]1(O)/C=C/C(C)=C\C(=O)O] | −7.2 |

TABLE 8-continued

Docking results of ABA analogs to LANCL2, ranked by the lowest binding energy.

| CID | Name | Chemical Structure | Lowest Binding Energy (kcal/mol) |
|---|---|---|---|
| 10086154 | (2Z,4E)-5-[(1S,6S)-6-(difluoromethyl)-1-hydroxy-2,6-dimethyl-4-oxocyclohex-2-en-1-yl]-3-methylpenta-2,4-dienoic acid | 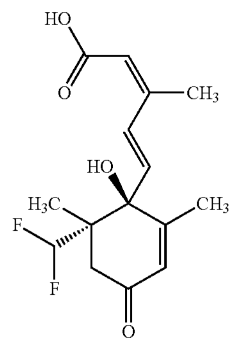 [SMILES: CC1=CC(=O)C[C@](C)(C(F)F)[C@]1(O)/C=C/C(C)=C\C(=O)O] | −7.1 |
| 10336005 | (2Z,4E)-5-[(1S,6R)-1-hydroxy-2,6-dimethyl-4-oxo-6-(trifluoromethyl)cyclohex-2-en-1-yl]-3-methylpenta-2,4-dienoic acid | 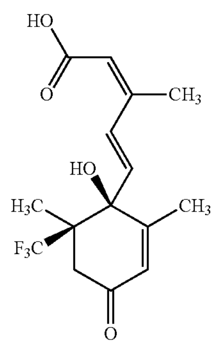 | −7.1 |
| 19882034 | (2E,4E)-2-fluoro-5-(1-hydroxy-2,6,6-trimethyl-4-oxocyclohex-2-en-1-yl)-3-methylpenta-2,4-dienoic acid | 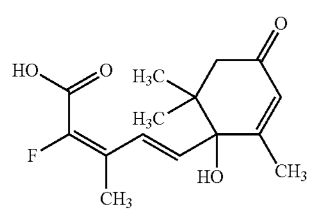 [SMILES: CC1=CC(=O)CC(C)(C)C1(O)/C=C/C(C)=C(/F)C(=O)O] | −7 |
| 6444312 | 4,4'-((2,4-Dihydroxy-5-(hydroxymethyl)-1,3-phenylene)bis(azo))bisnaphthalene-1-sulphonic acid | 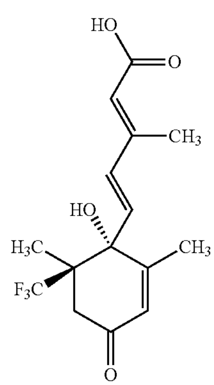 | −6.9 |

TABLE 8-continued

Docking results of ABA analogs to LANCL2, ranked by the lowest binding energy.

| CID | Name | Chemical Structure | Lowest Binding Energy (kcal/mol) |
|---|---|---|---|
| 10336004 | (2Z,4E)-5-[(1R,6R)-1-hydroxy-2,6-dimethyl-4-oxo-6-(trifluoromethyl)cyclohex-2-en-1-yl]-3-methylpenta-2,4-dienoic acid | 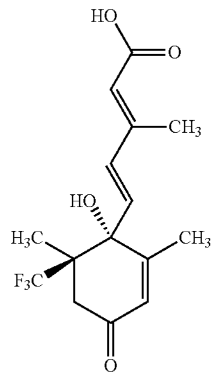 | −6.8 |
| 21639410 | (2E,4E)-5-(1-hydroxy-2,6,6-trimethyl-4-oxocyclohex-2-en-1-yl)-3-methylpenta-2,4-dienoate | 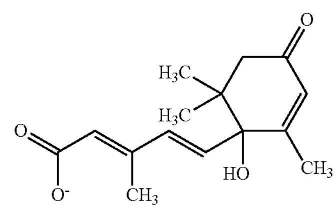 [SMILES: CC1=CC(=O)CC(C)(C)C1(O)/C=C/C(C)=C/C(=O)[O-]] | −6.8 |

Figure 15:
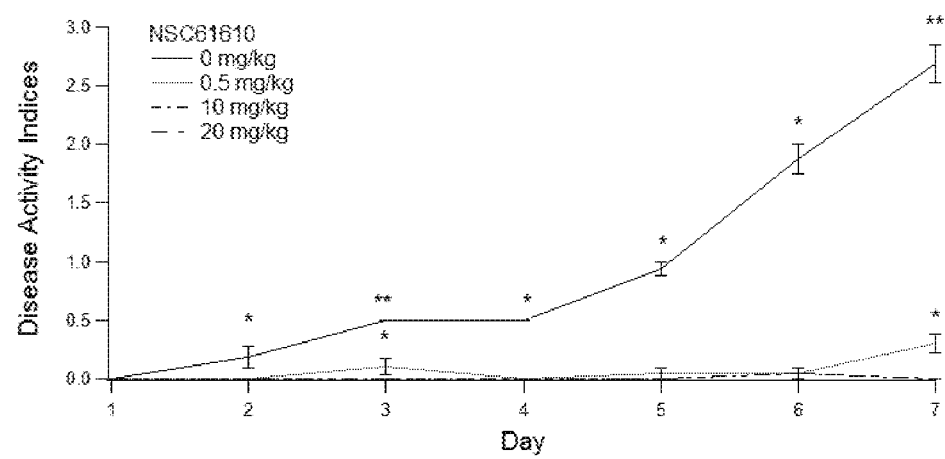
FIG. 15 illustrates the effect of NSC61610 on disease severity during experimental inflammatory bowel disease (IBD). The control mice and NSC61610-treated mice were challenged with 2.5% dextran sodium sulfate (DSS) for 7 days. Disease activity index (DAI), a composite score reflecting clinical signs of the disease (i.e. perianal soiling, rectal bleeding, diarrhea and piloerection), was assessed daily. Data are represented as mean±standard error. Points with an asterisk are significantly different ($P<0.05$).

NSC61610 Reduces Disease Activity and Inflammatory Lesions During Experiment IBD in Mice To determine the effect of NSC61610 on colonic inflammation, mice received placebo or were treated with increasing concentrations of NSC61610 (0.5, 10 and 20 mg/kg BW) for 7 days during the DSS challenge. After 7 days, mice treated with NSC61610 had a significantly reduced disease activity index (DAI) compared to untreated control mice (FIG. 15). Based on the gross pathological observation from FIG. 16, NSC61610 significantly reduced inflammation caused by DSS in colon, spleen and MLN. To more closely examine the effect of NSC61610, colonic specimens were examined histologically for the presence of inflammatory lesions. Our data indicates that NSC61610 significantly reduced epithelial erosion, mucosal thickening and leukocyte infiltration in mice with DSS colitis (FIG. 17).

NSC61610 Modulates Colonic Gene Expression

Figure 18:
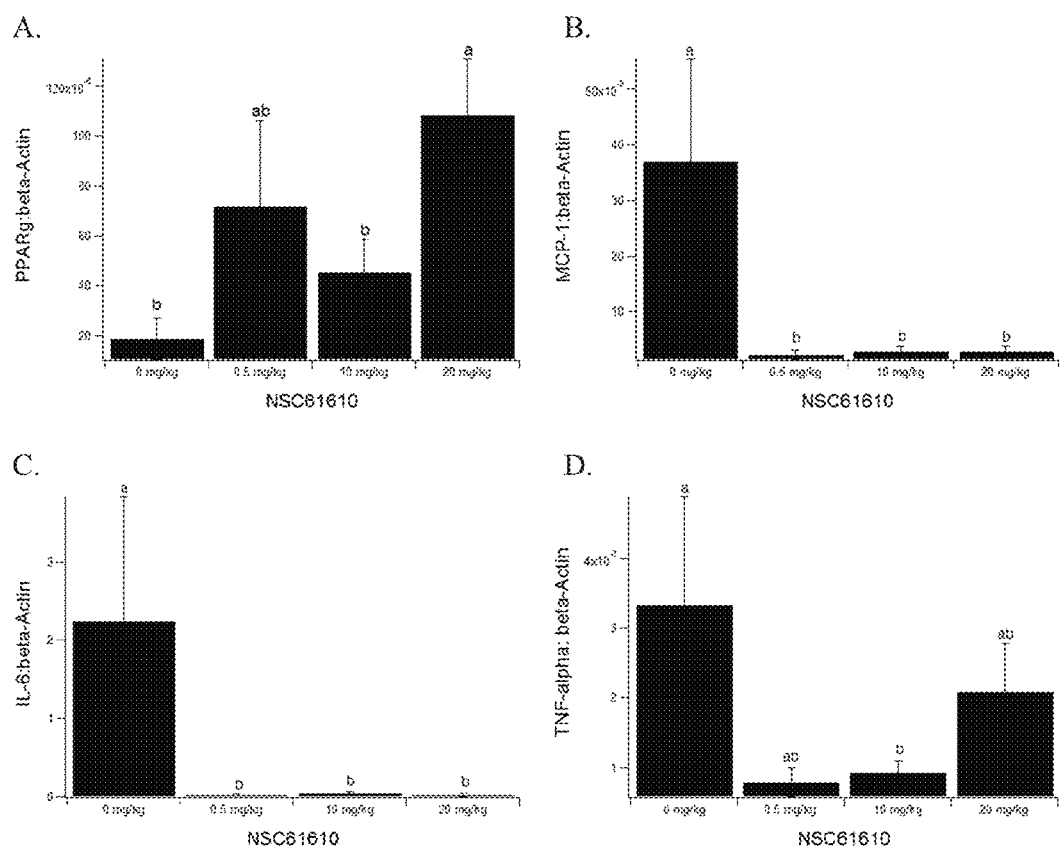
FIG. 18 illustrates the effect of NSC61610 on colonic gene expression. The control mice and NSC61610-treated mice were challenged with 2.5% dextran sodium sulfate (DSS) for 7 days. Expressions of peroxisome proliferator-activated receptor γ (PPARγ), monocyte chemoattractant protein-1 (MCP-1), pro-inflammatory protein interleukin-6 (IL-6), and tumor necrosis factor-alpha (TNF-α) were assessed by real-time quantitative PCR. Data for PPARγ (A), MCP-1 (B), IL-6 (C), and TNF-α (D) are represented as mean±standard error. Statistically significant differences (P<0.05) between treatments are indicated with different letter superscripts.

Our previous research showed that ABA activates PPAR γ, and PPAR γ agonists have been successfully used in the treatment of IBD [9]. Thus, we sought to determine whether NSC61610 modulates gene expression in a manner that resembled established agonists of PPAR γ such as rosiglitazone or conjugated linoleic acid. Here, we found evidence of PPAR γ-mediated effect in colons of NSC61610-treated mice. NSC61610 increased the PPAR γ gene expression in colon compared with control mice (FIG. 18). The maximum dose (20 mg/kg) of NSC61610 enhanced PPAR γ gene expression significantly.

In addition, NSC61610 significantly lowered expression of inflammatory mediators including monocyte chemoattractant protein-1 (MCP-1), pro-inflammatory cytokines interleukin-6 (IL-6) and tumor necrosis factor-alpha (TNF-α) (FIG. 18).

Results of previous studies had shown MCP-1 plays an important role in the pathogenesis of colitis in relation to the recruitment of immune cells, and the absence of this chemokine is associated with a significant reduction in inflammation [39]. IL-6 is protein secreted mainly by M1 activated macrophages. CD4+ T cells at the site of inflammation are critically dependent on antiapoptotic IL-6 signaling. This vicious circle of T-cell accumulation, mediated by apoptosis resistance, finally leading to chronic inflammation, can be blocked by anti-IL-6 receptor antibodies [40]. TNF-α is a cytokine involved in systemic inflammation. Large amounts of TNF-α are quickly released by stimulated mast cells. All the cells involved in inflammation have receptors for TNF-α and are activated by it to synthesize more on their own. This positive feedback quickly amplifies the response. Biologic agents directed against TNF-α have been applied as an effective therapeutic strategy for patients with IBD [41].

NSC61610 Influences the Phenotype of Immune Cells in Mice with IBD

Figure 19:
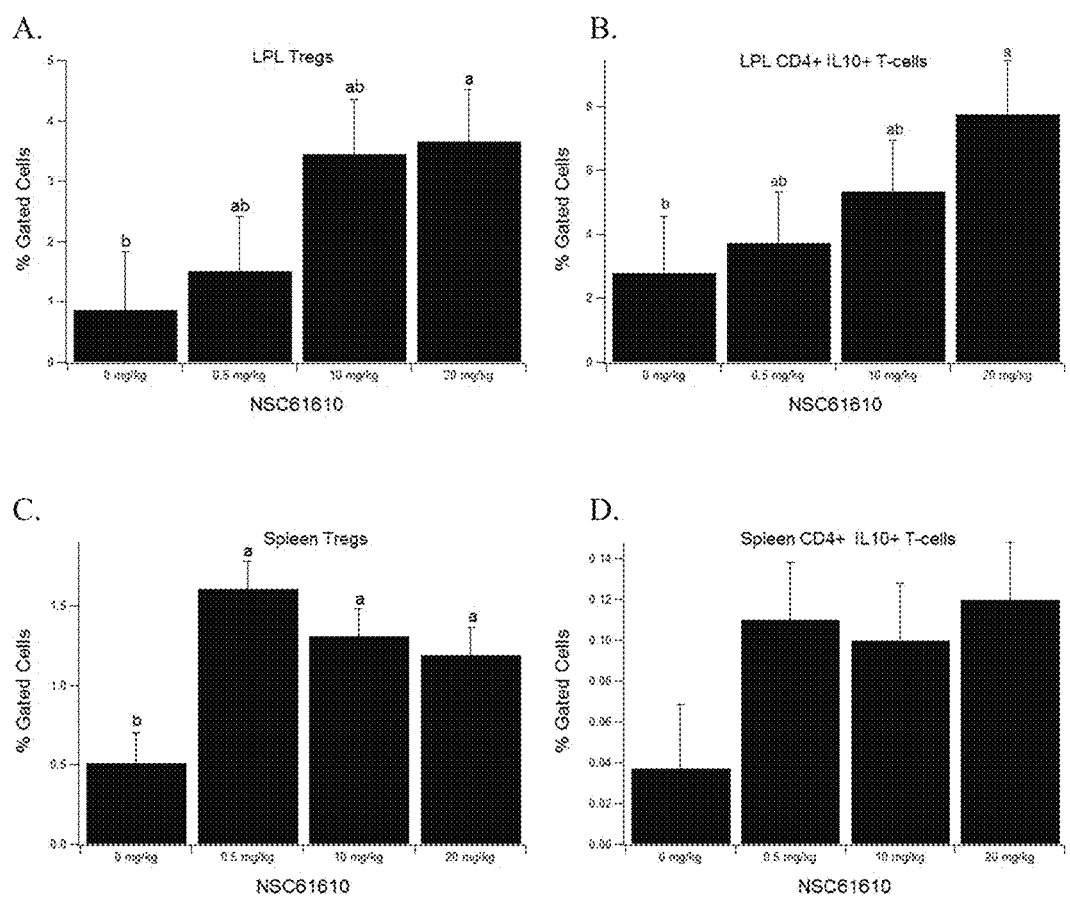
FIG. 19 illustrates the effect of NSC61610 on immune cell subsets in colon, spleen, mesenteric lymph nodes (MLN) and blood. Cells were immunophenotyped to identify immune cell subsets through flow cytometry with FACS diva software. (A) NSC61610 increases the numbers of regulatory T cells (Treg), a subset of anti-inflammatory immune cells, in the colonic lamina propria; (B) NSC61610 increases the numbers of CD4+IL-10+ T cells in the colonic lamina propria (IL-10 is an anti-inflammatory cytokine); (C) NSC61610 increases the numbers of Treg cells in spleen; (D) NSC61610 increases the numbers of CD4+IL-10+ T cells in spleen (E) No effect of NSC61610 on numbers of mesenteric lymph node (MLN) Treg; (F) NSC61610 increases the numbers of CD4+IL-10+ T cells in MLN; (G) NSC61610 increases the numbers of Treg cells in blood; (H) NSC61610 increases the numbers of CD4+ IL-10+ T cells in blood. Data are represented as mean±standard error. Statistically significant differences (P<0.05) between treatments are indicated with different letter superscripts.

To determine the effect of NSC61610 on immune cell subsets, we performed flow cytometric analysis on cells isolated from the colon, spleen, MLN, and blood. Our analysis indicated that NSC61610 significantly increased the percentages of Treg cells in colon, spleen, and blood (FIG. 19). Tregs are important for the maintenance of intestinal self-tolerance. Therapies that increase Treg numbers and function are under intense investigation and may prove to be promising treatments for patients with IBD [42-43].

The highest concentration NSC61610 also significantly increased the percentages of CD4+ IL10+ T cells in colon, spleen, MLN, and blood (FIG. 19). Interleukin-10 (IL-10) is a regulatory cytokine which inhibits both antigen presentation and subsequent pro-inflammatory cytokine release, and it is proposed as a potent anti-inflammatory biological therapy in chronic IBD. Many methods of IL-10 as a treatment for IBD have been published [44-45].

Figure 20:
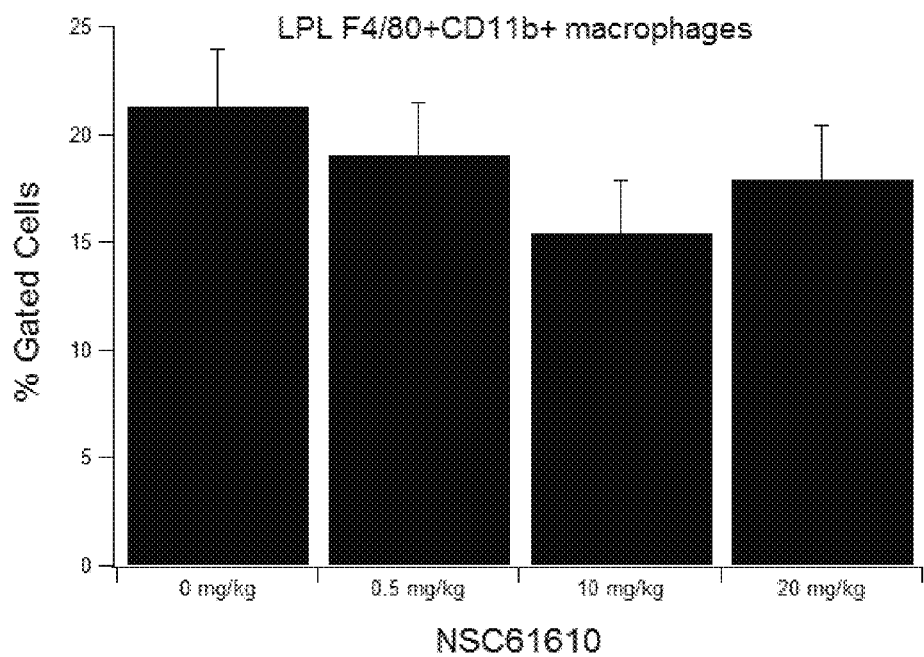
FIG. 20 illustrates the effect of NSC61610 on macrophages in the colonic lamina propria. Cells were immunophenotyped to identify macrophage subsets infiltrating the colonic mucosa through flow cytometry with FACS diva software. Data are represented as mean±standard error.

In addition, NSC61610 reduced the percentage of F4/80+ CD11 b+ macrophages in the colonic lamina propria (FIG. 20). Our previous research indicated that ABA ameliorates experimental IBD by suppressing immune cell infiltration [46]. Since NSC61610 also suppressed immune cell infiltration, we propose NSC61610 and ABA share the similar anti-inflammatory mechanism, thus indicating similar signal pathways and modes of action.

Combinations of ABA and Rosiglitazone Enhance LANCL2 Expression

Figure 21:
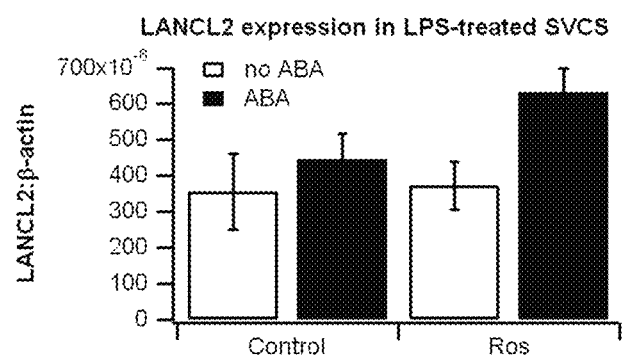
FIG. 21 illustrates expression of LANCL2 in stromal vascular cells (SVCs) treated with abscisic acid (ABA) and rosiglitazone (Ros). SVCs were isolated from white adipose tissue of obese db/db mice and treated with Ros (1 μM) or DMSO with or without ABA (10 μM) Cells were incubated with treatments for 6 hrs and were harvested in RLT/β-ME for RNA purification. RT-PCR for LANCL2 gene was performed from cDNA prepared from purified RNA (1 μg). Data for each sample were normalized to the housekeeping gene β-actin and are presented as mean±standard error.

We examined the combined effect of ABA and Rosiglitazone on white adipose tissue-derived stromal vascular cells (SVCs) in vitro. Isolated cells from obese db/db mice were treated with rosiglitazone (Ros, 1 µM) or DMSO with and without ABA (10 µM) prior to a 6 hr incubation with lipopolysaccharide (LPS, 100 ng/mL), and the expression of LANCL2 was measured with RT-PCR. We find that the combination of ABA and Rosiglitazone enhances LANCL2 expression greater than either compound individually in SVCs (FIG. 21).

NSC61610 Increases PPAR γ Expression 3T3-L1 Pre-Adipocytes

Figure 22:
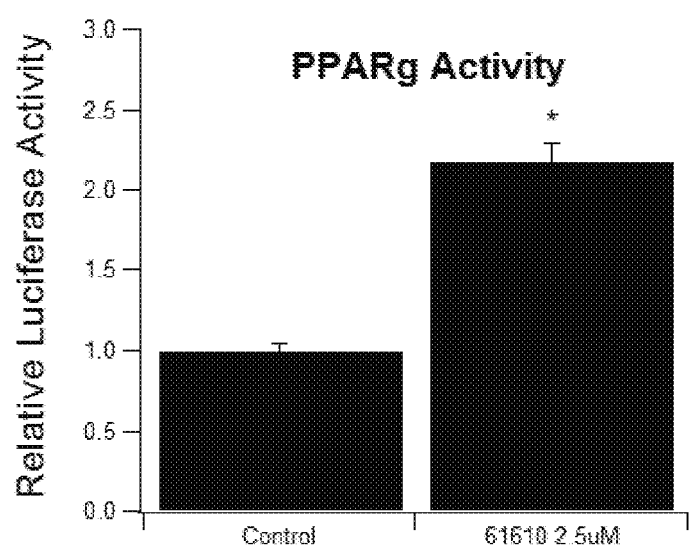
FIG. 22 illustrates the effect of NSC61610 treatment, a compound discovered based on its binding affinity with LANCL2, on PPAR γ expression. NSC61610 significantly elevated PPAR γ expression compared with untreated cells. Data were presented as mean±standard error. Data points with an asterisk are significantly different from control (P<0.05).

To check the effect of NSC61610 on PPAR γ activation, 3T3-L1 Pre-adipocytes were transfected with PPAR γ expression and dual luciferase plasmids and treated with 2.5 µM NSC61610 for 24 hours. Finally, the PPAR γ activity was analyzed by measuring the expression of two reporter luciferase genes. FIG. 22 illustrates that NSC61610 significantly elevated PPAR γ expression compared with untreated cells.

The Deficiency of PPAR γ in Macrophages Worsens Colitis Severity

Figure 23:
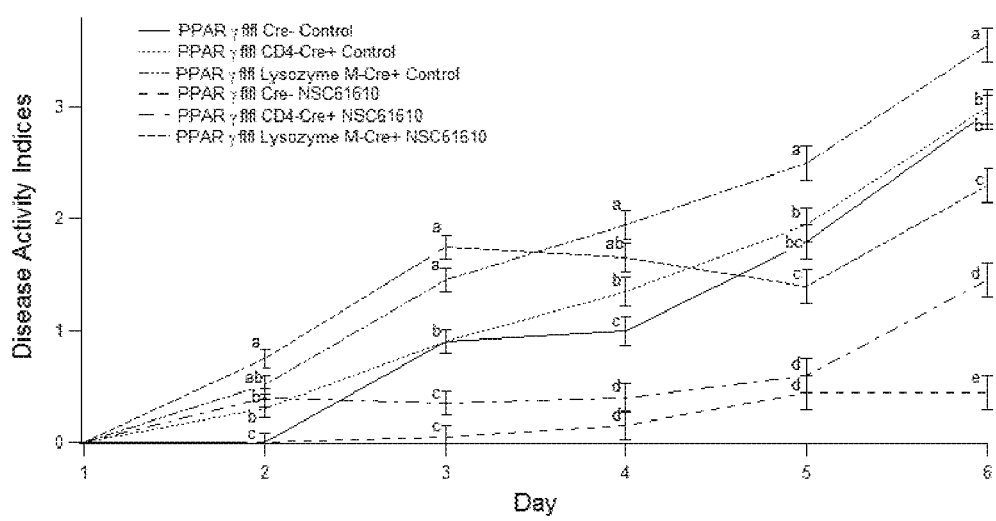
FIG. 23 illustrates the effect of tissue-specific PPAR γ deletion and NSC61610 on disease severity. The control mice and NSC61610-treated mice were challenged with 2.5% dextran sodium sulfate (DSS) for 6 days. Disease activity index (DAI), a composite score reflecting clinical signs of the disease (i.e. perianal soiling, rectal bleeding, diarrhea and piloerection), was assessed daily. Data are represented as mean±standard error. Points with an asterisk are significantly different (P<0.05).

To investigate the effect of NSC61610 and immune cell-specific PPAR γ deficiency on the severity of experimental IBD, wild-type (PPAR γ fl/fl, Cre−) mice and macrophage-specific PPAR γ null mice (PPAR γ fl/fl; lysozyme M-Cre+) and T cell-specific PPAR γ null mice (PPAR γ fl/fl; CD4-Cre+) were treated with 2.5% DSS in the drinking water for 6 days, and disease activity was monitored daily. Macrophage-specific PPAR γ null mice had worserned disease activity throughout the 6-day challenge. From day 4, macrophage-specific PPAR γ null mice had the significantly higher disease activity compared with PPAR γ fl/fl Cre− and PPAR γ fl/fl; CD4-Cre+ mice in both control and treatment groups (FIG. 23). On day 6, colons, spleens, and MLNs from mice in each group were scored based on gross pathological inflammatory lesions. In line with the disease activity index scores, both the colons and spleen were significantly more inflamed in PPAR γ fl/fl; Lysozyme M-Cre+ mice than Cre− and CD4-Cre+ mice (FIG. 24).

NSC61610 Reduces Disease Activity and Inflammatory Lesions Via a PPAR γ-Dependent Mechanism To determine the effect of NSC61610 on colonic inflammation, mice were treated with 20 mg/kg BW NSC61610 for 6 days during the DSS challenge. After 6 days, mice treated with NSC61610 had a significantly reduced disease activity index compared to untreated control mice (FIG. 23). To more closely examine the effect of NSC61610, colons, spleens and MLNs were examined macroscopically for the presence of inflammatory lesions. Our data indicates that NSC61610 significantly reduced macroscopic inflammatory lesions in PPAR γ-expressing and T cell-specific PPAR γ null mice with DSS colitis. However, the effect of NSC61610 on IBD was abrogated in MLNs and spleens of macrophage-specific PPAR γ null mice (FIG. 24). Thus, we posit that the anti-inflammatory efficacy of NSC61610 is dependent on PPAR γ expression in macrophages.

Anti-Inflammatory Efficacy of NSC61610 Against Respiratory Virus Infections

Figure 25:
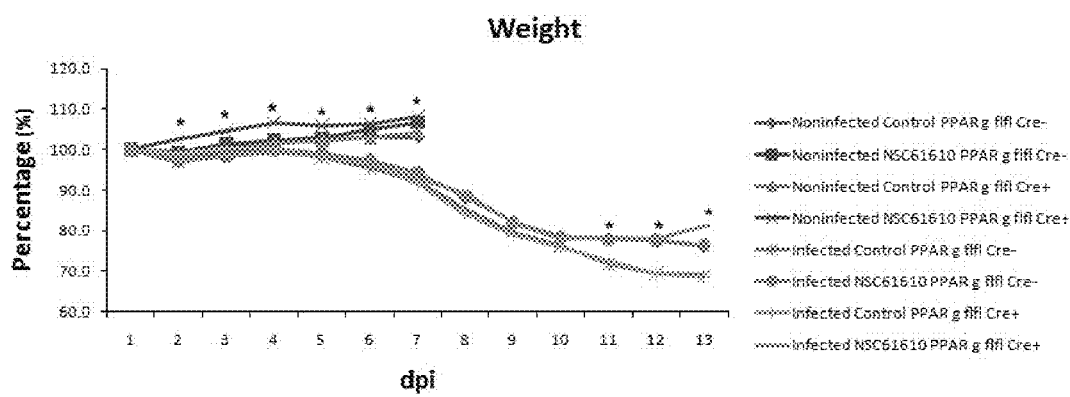
FIG. 25 illustrates the effect of influenza virus infection and NSC61610 on mice body weight. Host morbidity presented as mean of percentage original body weight. The infected mice were infected with pandemic influenza virus H1N1 on day 1 and influenza-related weight loss was monitored throughout the study. The treated mice received 20 mg/kg BW of NSC61610 by orogastric gavage daily. Mice were weighed on a daily basis. Asterisks indicate significant differences (P<0.05) exist between non-infected and infected mice from day 2 to day 7 and between control and treated mice from day 11 to day 13.
Figure 26:
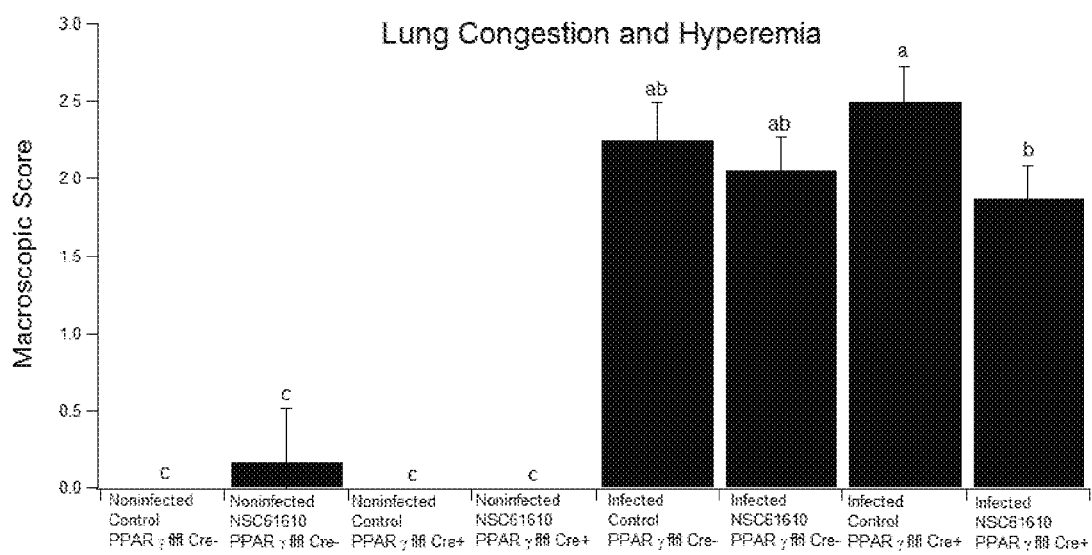
FIG. 26 illustrates the effect of influenza virus infection and NSC61610 on macroscopic score for lung congestion and hyperemia. Mice were infected with pandemic influenza virus H1N1 on day 1. The treated mice received 20 mg/kg NSC61610 by orogastric gavage daily. Data are represented as mean±standard error. Statistically significant differences (P<0.05) between treatments are indicated with different letter superscripts.
Figure 28:
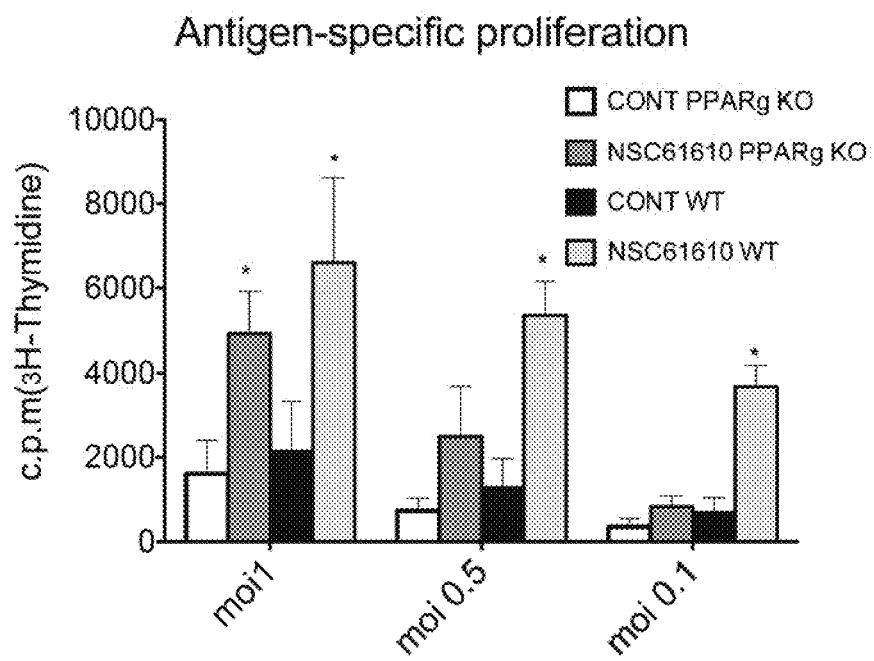
FIG. 28 illustrates the effect of influenza virus infection and NSC61610 on antigen-specific lymphoproliferative recall responses of mouse splenocytes. Mice were infected with pandemic influenza virus H1N1 on day 1. The treated mice received 20 mg/kg NSC61610 by orogastric gavage daily. Data are represented as mean±standard error. Statistically significant differences (P<0.05) between treatments are indicated with different letter superscripts.

The potential use of PPAR γ agonists to downregulate the inflammatory response to respiratory virus-related pulmonary inflammation was identified by us recently [47]. Previous research indicated that NSC61610 significantly elevated PPAR γ, thus we performed a study to test the anti-inflammatory efficacy of NSC61610 against pandemic H1N1 infection and pulmonary inflammation. Mice infected with influenza virus began losing weight soon after infection and by day 7 had lost about 10% of their pre-infection body weight, while noninfected mice kept a trend of gaining weight. Macroscopic scores illustrate that infected mice had higher disease activity scores. Infected mice treated with NSC61610 lost had lower weight loss than untreated infected mice. By day 13 infected mice treated with NSC61610 began to gain weight, indicating recovery from influenza virus infection (FIG. 25). Recovery was associated with higher antigen-specific proliferation of splenocytes stimulated ex vivo with live virus in mice that were treated with NSC61610 irrespective of the genotype. At the highest dose of virus (i.e., 1 MOI) the effect of NSC61610 was PPAR γ-independent as no differences were observed between the two mouse genotypes. However, at lower doses of virus (i.e. 0.5 and 0.1 MOI) the effect of NSC61610 was dependent on PPAR γ expression in immune and epithelial cells. These data indicate that the mice that received NSC61610 had enhanced T cell responses to the virus (FIG. 28). In line with weight data, macroscopic and histological score both showed that NSC61610 reduced the extent of lung congestion and hyperemia of infected mice (FIG. 26, 27). Therefore, we propose that NSC61610 as a potential anti-inflammatory therapy for respiratory virus infections that can enhance antigen-specific antiviral responses.

Reverse Docking-Based Identification of Other Potential Therapeutic Targets of NSC61610

TarFisDock analyzed the reverse docking results of NSC61610. TarFisDock output the top 10% of the ranking list of potential targets. Putative targets are selected by ranking the values of the interaction energy, which consists of van der Waals and electrostatic interaction terms. The top 10 reverse docking results of NSC61610 are show in Table 9. Of note, we show novel data indicating that a possible alternative mechanism by which NSC61610 may decrease inflammation is by targeting the leukotriene A4 hydrolase, an enzyme linked to the production of inflammatory lipid mediators such as leukotrienes.

TABLE 9

Potential therapeutic targets of NSC61610 and other LANCL2 ligands.

| PDB_ID | Energy Score | Target Name | Processes and Diseases |
| --- | --- | --- | --- |
| 1Q0N | −63.44 | 6-Hydroxymethyl-7,8-dihydropterin pyrophosphokinase (HPPK) | Infections; Microbial infections |
| 1HS6 | −61.89 | Leukotriene A4 hydrolase | Inflammation; leukotriene synthesis; Esophageal cancer |
| 1K6W | −61.24 | Cytosine deaminase | Epigenetic events; Cancer |
| 1HDT | −59.59 | Serine Proteinase alpha-thrombin | Haemostatic Disorders |
| 1FNO | −58.78 | Peptidase | |
| 1LGR | −57.52 | Glutamine Synthetase | Alzheimer's Disease, Huntington Disease |
| 1HDT | −57.5 | Serine Proteinase alpha-thrombin | Haemostatic Disorders |

TABLE 9-continued

Potential therapeutic targets of NSC61610 and other LANCL2 ligands.

| PDB_ID | Energy Score | Target Name | Processes and Diseases |
|---|---|---|---|
| 1XID | −57.47 | D-Xylose Isomerase | Carbohydrate metabolism |
| 1ED5 | −56.78 | Nitric Oxide Synthase | Vasodilation; Inflammation |
| 1GPN | −55.86 | Acetylcholinesterase | Alzheimer's Disease, Cognitive Deficits, Hypoxic-ischemic Encephalopathy, Motor Neurone Disease, Parkinson's Disease |

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

REFERENCES

1. Kumar, V., et al., *Robbins and Cotran pathologic basis of disease*. 7th ed. 2005, Philadelphia: Elsevier Saunders. xv, 1525 p.
2. Inzucchi, S. and R. Sherwin, *The Prevention of Type 2 Diabetes Mellitus*. Endocrinol Metab Clin N Am, 2005. 34: p. 199-219.
3. DeFronzo, R. A., *Pharmacologic therapy for type 2 diabetes mellitus*. Ann Intern Med, 1999. 131(4): p. 281-303.
4. DeFronzo, R., et al., *Effects of exenatide (exendin-4) on glycemic control and weight over 30 weeks in metformin-treated patients with type 2 diabetes*. Diabetes care, 2005. 28: p. 1092-100.
5. Rang, H., et al., *Pharmacology*. 5 ed. 2003.
6. Nesto, R. W., et al., *Thiazolidinedione use, fluid retention, and congestive heart failure: a consensus statement from the American Heart Association and American Diabetes Association*. Oct. 7, 2003. Circulation, 2003. 108: p. 2941-8.
7. Lewis, S. N., J. Bassaganya-Riera, and D. R. Bevan, *Virtual Screening as a Technique for PPAR Modulator Discovery*. PPAR Res, 2010. 2010: p. 861238.
8. Bassaganya-Riera, J., et al., *Mechanisms of Action and Medicinal Applications of Abscisic Acid*. Current medicinal chemistry, 2010.
9. Guri, A. J., et al., *Loss of PPAR gamma in immune cells impairs the ability of abscisic acid to improve insulin sensitivity by suppressing monocyte chemoattractant protein-1 expression and macrophage infiltration into white adipose tissue*. J Nutr Biochem, 2008. 19(4): p. 216-28.
10. Sturla, L., et al., *LANCL2 is necessary for abscisic acid binding and signaling in human granulocytes and in rat insulinoma cells*. The Journal of biological chemistry, 2009. 284: p. 28045-57.
11. Landlinger, C., U. Salzer, and R. Prohaska, *Myrisloylation of human LanC-like protein 2 (LANCL2) is essential for the interaction with the plasma membrane and the increase in cellular sensitivity to adriamycin*. Biochimica et biophysica acta, 2006. 1758: p. 1759-67.
12. Lu, P., et al., *Molecular modeling of lanthionine synthetase component C-like protein 2: a potential target for the discovery of novel type 2 diabetes prophylactics and therapeutics*. J Mol Model, 2011. 17(3): p. 543-53.
13. Zhang, W., et al., *Structure of human lanthionine synthetase C-like protein 1 and its interaction with Eps8 and glutathione*. Genes & development, 2009. 23: p. 1387-92.
14. Altschul, S. F., et al., *Basic local alignment search tool*. Journal of molecular biology, 1990. 215: p. 403-410.
15. Thompson, J. D., D. G. Higgins, and T. J. Gibson, *CLUSTAL W: improving the sensitivity of progressive multiple sequence alignment through sequence weighting, position-specific gap penalties and weight matrix choice*. Nucleic Acids Research, 1994. 22: p. 4673-80.
16. Subramaniam, S., *The Biology Workbench—a seamless database and analysis environment for the biologist*. Proteins, 1998. 32: p. 1-2.
17. Arnold, K., et al., *The SWISS-MODEL workspace: a web-based environment for protein structure homology modelling*. Bioinformatics (Oxford, England), 2006. 22: p. 195-201.
18. Berman, H. M., J. Westbrook, and Z. Feng, *The protein data bank*. Nucleic Acids Research, 2000. 28: p. 235-242.
19. Melo, F. and E. Feytmans, *Assessing protein structures with a non-local atomic interaction energy*. J. Mol. Biol, 1998. 277: p. 1141-1152.
20. Laskowski, R., et al., *PROCHECK: a program to check the stereochemical quality of protein structures*. Journal of Applied Crystallography, 1993. 26: p. 283-291.
21. Hess, B., et al., *GROMACS 4: Algorithms for Highly Efficient, Load-Balanced, and Scalable Molecular Simulation*. Journal of Chemical Theory and Computation, 2008. 4: p. 435-447.
22. Jorgensen, W. L. and J. Tirado-rives, *The OPLS Force Field for Proteins. Energy Minimizations for Crystals of Cyclic Peptides and Crambin*. J. Am. Chem. Soc., 1988. 110: p. 1657-1666.
23. Wiberg, K. B., *A Scheme for Strain Energy Minimization*. Journal of the American Chemical Society, 1965. 87: p. 1070-1078.
24. Mosca, R. and T. R. Schneider, *RAPIDO: a web server for the alignment of protein structures in the presence of conformational changes*. Nucleic Acids Research, 2008. 36: p. W42-6.
25. Wang, Y., et al., *PubChem: a public information system for analyzing bioactivities of small molecules*. Nucleic Acids Research, 2009. 37: p. W623-33.
26. Morris, G. M., et al., *Software News and Updates AutoDock4 and AutoDockTools4: Automated Docking with Selective Receptor Flexibility*. J. Comput. Chem., 2009. 30: p. 2785-2791.
27. Morris, G. M., et al., *Automated docking using a Lamarckian genetic algorithm and an empirical binding free energy function*. Journal of Computational Chemistry, 1998. 19: p. 1639-1662.
28. Hetenyi, C. and D. van Der Spoel, *Efficient docking of peptides to proteins without prior knowledge of the binding site*. Protein Science: A Publication of the Protein Society, 2002. 11: p. 1729.
29. Hetényi, C. and D. van der Spoel, *Blind docking of drug-sized compounds to proteins with up to a thousand residues*. FEBS letters, 2006. 580: p. 1447-50.
30. Bikádi, Z., et al., *Molecular modeling of non-covalent binding of homochiral (3S,3'S)-astaxanthin to matrix metalloproteinase-13 (MMP-13)*. Bioorganic & medicinal chemistry, 2006. 14: p. 5451-8.

31. Iorga, B., et al., *Acetylcholine nicotinic receptors: finding the putative binding site of allosteric modulators using the "blind docking" approach.* Journal of molecular modeling, 2006. 12: p. 366-72.
32. Hazai, E., et al., *Molecular modeling of the non-covalent binding of the dietary tomato carotenoids lycopene and lycophyll, and selected oxidative metabolites with 5-lipoxygenase.* Bioorganic & medicinal chemistry, 2006. 14: p. 6859-67.
33. Kovács, M., et al., *Mechanism of blebbistatin inhibition of myosin II.* The Journal of biological chemistry, 2004. 279: p. 35557-63.
34. Trott, O. and A. J. Olson, *AutoDock Vina: improving the speed and accuracy of docking with a new scoring function, efficient optimization, and multithreading.* J Comput Chem, 2010. 31(2): p. 455-61.
35. Rost, B., *Twilight zone of protein sequence alignments.* Protein Eng., 1999. 12: p. 85-94.
36. Gao, Z., et al., *PDTD: a web-accessible protein database for drug target identification.* BMC Bioinformatics, 2008. 9: p. 104.
37. Li, H., et al., *TarFisDock: a web server for identifying drug targets with docking approach.* Nucleic Acids Res, 2006. 34(Web Server issue): p. W219-24.
38. Humphrey, W., Dalke, A, Schulten, K, *VMD: visual molecular dynamics.* Journal of molecular graphics, 1996. 14(1): p. 33-38.
39. Khan, W. I., et al., *Critical role of MCP-1 in the pathogenesis of experimental colitis in the context of immune and enterochromaffin cells.* Am J Physiol Gastrointest Liver Physiol, 2006. 291(5): p. G803-11.
40. Mudter, J. and M. F. Neurath, *Il-6 signaling in inflammatory bowel disease: pathophysiological role and clinical relevance.* Inflamm Bowel Dis, 2007. 13(8): p. 1016-23.
41. van Heel, D. A., et al., *Inflammatory bowel disease is associated with a TNF polymorphism that affects an interaction between the OCT1 and NF(-kappa)B transcription factors.* Hum Mol Genet, 2002. 11(11): p. 1281-9.
42. Groux, H. and F. Powrie, *Regulatory T cells and inflammatory bowel disease.* Immunol Today, 1999. 20(10): p. 442-5.
43. Boden, E. K. and S. B. Snapper, *Regulatory T cells in inflammatory bowel disease.* Curr Opin Gastroenterol, 2008. 24(6): p. 733-41.
44. Leach, M. W., et al., *The role of IL-10 in inflammatory bowel disease: "of mice and men".* Toxicol Pathol, 1999. 27(1): p. 123-33.
45. Li, M. C. and S. H. He, *IL-10 and its related cytokines for treatment of inflammatory bowel disease.* World J Gastroenterol, 2004. 10(5): p. 620-5.
46. Guri, A. J., et al., *Abscisic acid ameliorates atherosclerosis by suppressing macrophage and CD4+ T cell recruitment into the aortic wall.* J Nutr Biochem, 2010. 21(12): p. 1178-85.
47. Bassaganya-Riera, J., et al., *PPAR-gamma activation as an anti-inflammatory therapy for respiratory virus infections.* Viral Immunol, 2010. 23(4): p. 343-52.

What is claimed is:

1. A method for activating PPARγ in a cell comprising the step of contacting the cell with a compound effective to bind LANCL2, wherein the compound is NSC61610.

2. The method of claim 1, wherein the compound increases the expression or activity of PPARγ.

3. The method of claim 1, wherein the compound is part of a nutritional supplement, a nutraceutical, a functional food, or dietary aid.

4. The method of claim 1, wherein the compound is also effective to suppress expression of an inflammatory molecule in cells or to suppress inflammatory cells.

5. The method of claim 4, wherein the inflammatory molecule is tumor necrosis factor alpha or monocyte chemoattractant protein-1.

6. The method of claim 4, wherein the inflammatory cells are inflammatory or M1 classically activated macrophage or other inflammatory phagocytes.

7. A method for treating inflammation, diabetes, or obesity comprising the steps of administering to an individual in need thereof a compound effective to bind LANCL2 and to activate PPARγ, wherein the compound is NSC61610 and wherein the inflammation is gastrointestinal tract inflammation, lung inflammation, or inflammation caused by influenza A or B virus, respiratory syncytial virus, Streptoeoecuspneumoniae, parainfluenza, rhinoviruses, *Staphylococcus aureus, Francisella tularensis, Yersinia pestis, Bacillus anthraces, Mycobacterium tuberculosis*.

8. The method of claim 7, wherein the compound is part of a nutritional supplement, a nutraceutical, a functional food, or dietary aid.

9. The method of claim 7, wherein the inflammation causes epithelial necrosis, airway infiltration with immune cells, mucosal and submucosal infiltration with immune cells and perivascular cuffing.

10. The method of claim 7, wherein amount of the compound that is sufficient to alter the expression or activity of PPAR $\gamma$ in a cell of the mammal is between about 0.5 mg/day and about 6,000 mg/day.

* * * * *